(12) United States Patent
Charest et al.

(10) Patent No.: US 8,044,209 B2
(45) Date of Patent: Oct. 25, 2011

(54) PYRROLYDINE DERIVATIVES AS IAP INHIBITORS

(75) Inventors: Mark G. Charest, Cambridge, MA (US); Christine Hiu-Tung Chen, Waltham, MA (US); Ming Chen, Jupiter, FL (US); Zhuoliang Chen, Belmont, MA (US); Miao Dai, Dover, MA (US); Feng He, Arlington, MA (US); Huangshu Lei, Durham, NC (US); Christopher Sean Straub, Stow, MA (US); Run-Ming David Wang, Cambridge, MA (US); Leigh Zawel, Hingham, MA (US)

(73) Assignee: Novartis AG, Basel (CH)

( * ) Notice: Subject to any disclaimer, the term of this patent is extended or adjusted under 35 U.S.C. 154(b) by 1 day.

(21) Appl. No.: 12/445,435

(22) PCT Filed: Oct. 10, 2007
(Under 37 CFR 1.47)

(86) PCT No.: PCT/US2007/080875
§ 371 (c)(1),
(2), (4) Date: Jul. 12, 2010

(87) PCT Pub. No.: WO2008/045905
PCT Pub. Date: Apr. 17, 2008

(65) Prior Publication Data
US 2011/0015232 A1    Jan. 20, 2011

Related U.S. Application Data

(60) Provisional application No. 60/829,234, filed on Oct. 12, 2006.

(51) Int. Cl.
*A61K 31/4439* (2006.01)
*C07D 405/14* (2006.01)
*C07D 401/14* (2006.01)

(52) U.S. Cl. ............... 546/279.1; 546/277.4; 546/273.4; 435/375

(58) Field of Classification Search .................. None
See application file for complete search history.

(56) References Cited

U.S. PATENT DOCUMENTS

2006/0167066 A1    7/2006   Cohen et al.

FOREIGN PATENT DOCUMENTS

| WO | WO 01/90070 A2 | 5/2001 |
|----|----|----|
| WO | WO 2004/005248 A1 | 1/2004 |
| WO | WO 2004/007529 A2 | 1/2004 |
| WO | WO 2005/097791 A1 | 10/2005 |
| WO | WO 2006/014361 A1 | 2/2006 |
| WO | WO 2006/069063 A1 | 6/2006 |
| WO | WO 2007/106192 A2 | 9/2007 |

OTHER PUBLICATIONS

Arnt et al., "Synthetic Smac/DIABLO Peptides Enhance the Effects of Chemotherapeutic Agents by Binding XIAP and cIAP1 in Situ", Journal of Bilogical Chemistry, 2002 vol. 277 No. 46 pp. 44236-44243.
Deal et al., "Conformationally Constrained Tachykinin Analogues: Potent and Highly Selective Neurokinin NK-2 Receptor Agonists", Journal of Medicinal Chemistry, 1992 vol. 35 pp. 4195-4204.
Kipp et al., "Molecular Targeting of Inhibitor of Apoptosis Proteins Based on Small Molecule Mimics of Natural Binding Partners", Biochemistry, 2002 vol. 41 pp. 7344-7349.
Stables et al., "GR138676, A Novel Peptidic Tachykinin Antagonist Which is Potent at NK3 Receptors", Neuropeptides, 1994 vol. 27 pp. 333-341.
Wu et al., "Structural Analysis of a Functional DIAP1 Fragment Bound to Grim and Hid Peptides", Molecular Cell, 2001 vol. 8 No. 1 pp. 95-104.

*Primary Examiner* — Brandon Fetterolf
*Assistant Examiner* — Anna Pagonakis

(57) ABSTRACT

The present invention relates to novel IAP inhibitor compounds of: Formula (I).

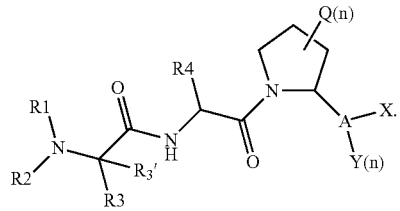

Formula I

10 Claims, No Drawings

PYRROLYDINE DERIVATIVES AS IAP INHIBITORS

This application is a U.S. National Phase filing of International Application Serial No. PCT/US2007/080875 filed 10 Oct. 2007 and claims priority to U.S. Provisional Application Ser. No. 60/829,234 filed 12 Oct. 2006, the contents of which are incorporated herein by reference in their entirety.

The present invention relates generally to novel compounds that inhibit the binding of the Smac protein to Inhibitor of Apoptosis Proteins (IAPs). More specifically, the present invention includes novel compounds, novel compositions, methods of their use and methods of their manufacture, where such compounds are generally pharmacologically useful as agents in therapies whose mechanism of action rely on the inhibition of the Smac/IAP interaction, and more particularly useful in therapies for the treatment of proliferative diseases, including cancer.

BACKGROUND

Programmed cell death plays a critical role in regulating cell number and in eliminating stressed or damaged cells from normal tissues. Indeed, the network of apoptotic signaling mechanisms inherent in most cell types provides a major barrier to the development and progression of human cancer. Since most commonly used radiation and chemo-therapies rely on activation of apoptotic pathways to kill cancer cells, tumor cells which are capable of evading programmed cell death often become resistant to treatment.

Apoptosis signaling networks are classified as either intrinsic when mediated by death receptor-ligand interactions or extrinsic when mediated by cellular stress and mitochondrial permeabilization. Both pathways ultimately converge on individual Caspases. Once activated, Caspases cleave a number of cell death-related substrates, effecting destruction of the cell.

Tumor cells have devised a number of strategies to circumvent apoptosis. One recently reported molecular mechanism involves the overexpression of members of the IAP (Inhibitor of Apoptosis) protein family. IAPs sabotage apoptosis by directly interacting with and neutralizing Caspases. The prototype IAPs, XIAP and cIAP have three functional domains referred to as BIR 1, 2 & 3 domains. BIR3 domain interacts directly with Caspase 9 and inhibits its ability to bind and cleave its natural substrate, Procaspase 3.

It has been reported that a proapoptotic mitochondrial protein, Smac (also known as DIABLO), is capable of neutralizing XIAP and/or cIAP by binding to a peptide binding pocket (Smac binding site) on the surface of BIR3 thereby precluding interaction between XIAP and/or cIAP and Caspase 9. Binding of peptides derived from Smac has also been reported to trigger autocatalytic polyubiquitination and subsequent proteosome-mediated degradation of CIAP1. The present invention relates to therapeutic molecules that bind to the Smac binding pocket thereby promoting apoptosis in rapidly dividing cells. Such therapeutic molecules are useful for the treatment of proliferative diseases, including cancer.

SUMMARY OF THE INVENTION

The present invention relates to novel compounds of formula I:

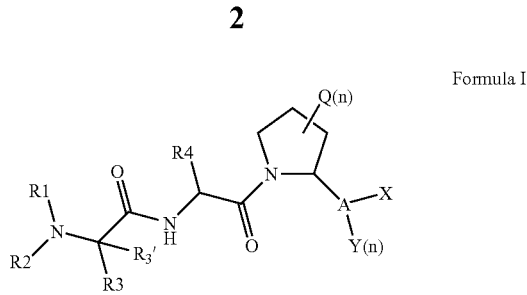

Formula I and pharmaceutically acceptable salts thereof, wherein
$R_1$ is H, $C_1$-$C_4$ alkyl, $C_2$-$C_4$ alkenyl, $C_2$-$C_4$ alkynyl or $C_3$-$C_{10}$ cycloalkyl, which $R_1$ may be unsubstituted or substituted;
$R_2$ is H, $C_1$-$C_4$ alkyl, $C_2$-$C_4$ alkenyl, $C_2$-$C_4$ alkynyl, $C_3$-$C_{10}$ cycloalkyl which $R_2$ may be unsubstituted or substituted;
$R_1$ and $R_2$ may be taken together to form a ring or het;
$R_3$ and $R_3'$ are independently H, $CF_3$, $C_2F_5$, $C_1$-$C_4$ alkyl, $C_2$-$C_4$ alkenyl, $C_2$-$C_4$ alkynyl, $CH_2$—Z or $R_2$ and $R_3$ taken together with the nitrogen atom to which they are attached form het, wherein alkyl, alkenyl, alkynyl or het ring may be unsubstituted or substituted;
Z is H, OH, F, Cl, $CH_3$, $CH_2Cl$, $CH_2F$ or $CH_2OH$;
$R_4$ is $C_{0-10}$ alkyl, $C_{0-10}$ alkyl-$C_{3-10}$ cycloalkyl, $C_{0-10}$alkyl-$C_{6-10}$aryl, $C_{0-10}$alkyl-het, wherein any carbon may be replaced with a heteroatom or group from the list N, O, $S(O)_r$ and any atom may be unsubstituted or substituted;
A is a 6 membered heteroaryl ring or an 8-12 membered fused ring system that may include one 5-7 membered heterocyclic ring containing 1, 2, or 3 hetero ring atoms selected from N, O and S, which any position of the rings is unsubstituted or substituted with one or more Q's;
r is 0, 1, or 2;
Q and Y are independently H, F, Cl, Br, I, $C_1$-$C_{10}$ alkyl, $C_1$-$C_{10}$ alkoxy, aryl $C_1$-$C_{10}$ alkoxy, OH, O—$C_1$-$C_{10}$-alkyl, $(CH_2)_{0-6}$—$C_3$-$C_7$ cycloalkyl, aryl, aryl $C_1$-$C_{10}$ alkyl, O—$(CH_2)_{0-6}$ aryl, $(CH_2)_{1-6}$het, het, O—$(CH_2)_{1-6}$het, —$OR_{11}$, $C(O)R_{11}$, —$C(O)N(R_{11})(R_{12})$, $N(R_{11})(R_{12})$, $SR_{11}$, $S(O)R_{11}$, $S(O)_2R_{11}$, $S(O)_2$—$N(R_{11})(R_{12})$, or $NR_{11}$—$S(O)_2$—$(R_{12})$, wherein alkyl, cycloalkyl and aryl are unsubstituted or substituted, independent Q's may be joined to form a 5-10 membered ring;
X is aryl, $C_3$-$C_{10}$ cycloalkyl, or het, substituted or unsubstituted, in which substituents on aryl, $C_3$-$C_{10}$ cycloalkyl and het are alkyl, halo, lower alkoxy, $NR_5R_6$, CN, $NO_2$ or $SR_5$;
$R_5$ and $R_6$ are independently H, F, Cl, Br, I, $C_1$-$C_{10}$ alkyl, $C_1$-$C_{10}$ alkoxy, aryl $C_1$-$C_{10}$ alkoxy, OH, O—$C_1$-$C_{10}$-alkyl, $(CH_2)_{0-6}$—$C_3$-$C_7$ cycloalkyl, aryl, aryl $C_1$-$C_{10}$ alkyl, O—$(CH_2)_{0-6}$ aryl, $(CH_2)_{1-6}$het, het, O—$(CH_2)_{1-6}$het, —$OR_{11}$, $C(O)R_{11}$, —$C(O)N(R_{11})(R_{12})$, $N(R_{11})(R_{12})$, $SR_{11}$, $S(O)R_{11}$, $S(O)_2R_{11}$, $S(O)_2$—$N(R_{11})(R_{12})$, or $NR_{11}$—$S(O)_2$—$(R_{12})$;
each n is independently 0, 1, 2, 3, 4, 5, 6 or 7;
het is a 5-7 membered monocyclic heterocyclic ring containing 1-4 hetero ring atoms selected from N, O and S or an 8-12 membered fused ring system that includes one 5-7 membered heterocyclic ring containing 1, 2, or 3 hetero ring atoms selected from N, O and S, which het is unsubstituted or substituted;
$R_{11}$ and $R_{12}$ are independently H, $C_1$-$C_{10}$ alkyl, $(CH_2)_{0-6}$—$C_3$-$C_7$cycloalkyl, $(CH_2)_{0-6}$—$(CH)_{0-1}$(aryl)$_{1-2}$, $C(O)$—$C_1$-$C_{10}$alkyl, —$C(O)$—$(CH_2)_{0-6}$—$C_3$-$C_7$cycloalkyl, —$C(O)$—O—$(CH_2)_{0-6}$-aryl, —$C(O)$—$(CH_2)_{0-6}$—O— fluorenyl, C(O)—NH—(CH$_2$)$_{0-6}$-aryl, C(O)—(CH$_2$)$_{0-6}$-aryl, C(O)—(CH$_2$)$_{0-6}$-het, —C(S)—C$_1$-C$_{10}$alkyl, —C(S)—(CH$_2$)$_{0-6}$—C$_3$-C$_7$cycloalkyl, —C(S)—O—(CH$_2$)$_{0-6}$-aryl, —C(S)—(CH$_2$)$_{0-6}$—O-fluorenyl, C(S)—NH—(CH$_2$)$_{0-6}$-aryl, —C(S)—(CH$_2$)$_{0-6}$-aryl or C(S)—(CH$_2$)$_{0-6}$-het, C(O)R$_{11}$, C(O)NR$_{11}$R$_{12}$, C(O)OR$_{11}$, S(O)nR$_{11}$, S(O)$_m$NR$_{11}$R$_{12}$, m=1 or 2, C(S)R$_{11}$, C(S)NR$_{11}$R$_{12}$, C(S)OR$_{11}$, wherein alkyl, cycloalkyl and aryl are unsubstituted or substituted; or R$_{11}$ and R$_{12}$ together with the nitrogen atom form het; wherein the alkyl substituents of R$_{11}$ and R$_{12}$ may be unsubstituted or substituted by one or more substituents selected from C$_1$-C$_{10}$alkyl, halogen, OH, O—C$_1$-C$_6$alkyl, —S—C$_1$-C$_6$alkyl, CF$_3$ or NR$_{11}$R$_{12}$;

substituted cycloalkyl substituents of R$_{11}$ and R$_{12}$ are substituted by one or more substituents selected from a O$_2$—C$_{10}$ alkene; O$_1$—C$_6$alkyl; halogen; OH; O—C$_1$-C$_6$alkyl; S—C$_1$-C$_6$alkyl, CF$_3$; or NR$_{11}$R$_{12}$ and substituted het or substituted aryl of R$_{11}$ and R$_{12}$ are substituted by one or more substituents selected from halogen, hydroxy, C$_1$-C$_4$ alkyl, C$_1$-C$_4$ alkoxy, nitro, CNO—C(O)—C$_1$-C$_4$alkyl and C(O)—O—C$_1$-C$_4$-alkyl;

wherein the substituents on R$_1$, R$_2$, R$_3$, R$_4$, Q, and A and X groups are independently halo, hydroxy, lower alkyl, lower alkenyl, lower alkynyl, lower alkanoyl, lower alkoxy, aryl, aryl lower alkyl, amino, amino lower alkyl, diloweralkylamino, lower alkanoyl, amino lower alkoxy, nitro, cyano, cyano lower alkyl, carboxy, lower carbalkoxy, lower alkanoyl, aryloyl, lower arylalkanoyl, carbamoyl, N-mono- or N,N-dilower alkyl carbamoyl, lower alkyl carbamic acid ester, amidino, guanidine, ureido, mercapto, sulfo, lower alkylthio, sulfoamino, sulfonamide, benzosulfonamide, sulfonate, sulfanyl lower alkyl, aryl sulfonamide, halogen substituted aryl sulfonate, lower alkylsulfinyl, arylsulfinyl; aryl-lower alkylsulfinyl, lower alkylarylsulfinyl, lower alkylsulfonyl, arylsulfonyl, aryl-lower alkylsulfonyl, lower aryl alkyl lower alkylarylsulfohyl, halogen-lower alkylmercapto, halogen-lower alkylsulfonyl, phosphono (—P(=O)(OH)$_2$), hydroxy-lower alkoxy phosphoryl or di-lower alkoxyphosphoryl, (R$_9$)NC(O)—NR$_{10}$R$_{13}$, lower alkyl carbamic acid ester or carbamates or —NR$_8$R$_{14}$, wherein R$_8$ and R$_{14}$ can be the same or different and are independently H or lower alkyl, or R$_8$ and R$_{14}$ together with the N atom form a 3- to 8-membered heterocyclic ring containing a nitrogen heteroring atoms and may optionally contain one or two additional heteroring atoms selected from nitrogen, oxygen and sulfur, which heterocyclic ring may be unsubstituted or substituted with lower alkyl, halo, lower alkenyl, lower alkynyl, hydroxy, lower alkoxy, nitro, amino, lower alkyl, amino, diloweralkyl amino, cyano, carboxy, lower carbalkoxy, formyl, lower alkanoyl, oxo, carbarmoyl, N-lower or N,N-dilower alkyl carbamoyl, mercapto, or lower alkylthio, and R$_9$, R$_{10}$, and R$_{13}$ are independently hydrogen, lower alkyl, halogen substituted lower alkyl, aryl, aryl lower alkyl, halogen substituted aryl, halogen substituted aryl lower alkyl.

The present invention also relates to pharmaceutical compositions comprising therapeutically effective amounts of compounds of Formula I, as defined hereinabove, or a pharmaceutically acceptable salt thereof, and a pharmaceutical carrier therefor. In another embodiment, the present invention is directed to a method of treating a mammal, especially human, afflicted with a proliferative disease, especially those dependent on the binding of the smac protein to Inhibitor of Apoptosis Proteins (IAPs), such as cancer, which method comprises administering to said mammal in need of treatment an anti-proloferative effective amount of a compound of Formula I or a pharmaceutically acceptable salt thereof. The present invention is also directed to the manufacture of compounds of Formula I for use in the treatment of said diseases.

DETAILED DESCRIPTION OF THE PRESENT INVENTION

As used herein, the term "Aryl" is defined as an aromatic radical having 6 to 14 ring carbon atoms, and no ring heteroatoms. The aryl group may be monocyclic or fused bicyclic or tricyclic. It may be unsubstituted or substituted by one or more, preferably one or two, substituents, wherein the substituents are as described herein. As defined herein, the aryl moiety may be completely aromatic regardless of whether it is monocyclic or bicyclic. However, if it contains more than one ring, as defined herein, the term aryl includes moieties wherein at least one ring is completely aromatic while the other ring(s) may be partially unsaturated or saturated or completely aromatic. Preferred "aryl" is phenyl or naphthyl. The most preferred aryl is phenyl.

"Het" as used herein, refers to heteroaryl and heterocyclic compounds containing at least one S, O or N ring heteroatom. More specifically, "Het" is a 5-7 membered heterocyclic ring containing 1-4 heteroatoms selected from N, O and S, or an 8-12 membered fused ring system including at least one 5-7 membered heterocyclic ring containing 1, 2 or 3 heteroatoms selected from N, O, and S. Examples of het, as used herein, include unsubstituted and substituted pyrrolidyl, tetrahydrofuryl, tetrahydrothiofuryl, piperidyl, piperazyl, purinyl, tetrahydropyranyl, morpholino, 1,3-diazapanyl, 1,4-diazapanyl, 1,4-oxazepanyl, 1,4-oxathiapanyl, furyl, thienyl, pyrryl, pyrrolyl, pyrazolyl, triazolyl, tetrazolyl, indazolyl, oxadiazolyl, imidazolyl, pyrrolidyl, pyrrolidinyl, thiazolyl, oxazolyl, pyridyl, pyrazolyl, pyrazinyl, pyrimidinyl, isoxazolyl, pyrazinyl, quinolyl, isoquinolyl, pyridopyrazinyl, pyrrolopyridyl, furopyridyl, indolyl, benzofuryl, benzothiofuryl, benzoindolyl, benzothienyl, pyrazolyl, piperidyl, piperazinyl, indolinyl, morpholinyl, benzoxazolyl, pyrroloquinolyl, pyrrolo[2,3-b]pyridinyl, benzotriazolyl, oxobenzo-oxazolyl, benco[1,3]dioxolyl, benxzoimidazolyl, quinolinyl, indanyl and the like. Heteroaryls are within the scope of the definition of het. Examples of heteroaryls are pyridyl, pyrimidinyl, quinolyl, thiazolyl and benzothiazolyl. The most preferred het are pyridyl, pyrimidinyl and thiazolyl. The het may be unsubstituted or substituted as described herein. It is preferred that it is unsubstituted or if substituted it is substituted on a carbon atom by halogen, especially fluorine or chlorine, hydroxy, C$_1$-C$_4$ alkyl, such as methyl and ethyl, C$_1$-C$_4$ alkoxy, especially methoxy and ethoxy, nitro, —O—C(O)—C$_1$-C$_4$alkyl or —C(O)—O—C$_1$-C$_4$alkyl, SCN or nitro or on a nitrogen atom by C$_1$-C$_4$ alkyl, especially methyl or ethyl, —O—C(O)—C$_1$-C$_4$alkyl or —C(O)—O—C$_1$-C$_4$alkyl, such as carbomethoxy or carboethoxy.

When two substituents together with a commonly bound nitrogen are het, it is understood that the resulting heterocyclic ring is a nitrogen-containing ring, such as aziridine, azetidine, azole, piperidine, piperazine, morpholine, pyrrole, pyrazole, thiazole, oxazole, pyridine, pyrimidine, isoxazole, and the like, wherein such het may be unsubstituted or substituted as defined hereinabove.

Halogen is fluorine, chlorine, bromine or iodine, especially fluorine and chlorine.

Unless otherwise specified "alkyl", either above or in combination, includes straight or branched chain alkyl, such as methyl, ethyl, n-propyl, isopropyl, n-butyl, sec-butyl, tert-butyl, n-pentyl and branched pentyl, n-hexyl and branched hexyl, and the like.

A "cycloalkyl" group means $C_3$ to $C_{10}$ cycloalkyl having 3 to 10 ring carbon atoms and may be, for example, cyclopropyl, cyclobutyl, cyclopentyl, cyclohexyl, cycloheptyl or cyclooctyl, cyclononyl and the like. The cycloalkyl group may be monocyclic or fused bicyclic. It is preferred that it is monocyclic. Moreover, the preferred cycloalkyl group is cyclopentyl or cyclohexyl. Most preferably, cycloalkyl is cyclohexyl. The cycloalkyl group may be fully saturated or partially unsaturated, although it is preferred that it is fully saturated. As defined herein, it excludes aryl groups. The cycloalkyl groups may be unsubstituted or substituted with any of the substituents defined below, preferably halo, hydroxy or $C_1$-$C_6$ alkyl such as methyl.

Substituents that facilitate transport of the molecule across a cell membrane are known to those of skill in the medicinal chemistry arts (see, for example, Gangewar S., Pauletti G. M., Wang B., Siahaan T. J., Stella V. J., Borchardt R. T., *Drug Discovery Today*, vol. 2. p 148-155 (1997) and Bundgaard H. and Moss J., *Pharmaceutical Research*, vol. 7, p 885 (1990)). Generally, such substituents are lipophillic substituents. Such lipophillic substituents include a $C_6$-$C_{30}$ alkyl which is saturated, monounsaturated, polyunsaturated, including methylene-interrupted polyene, phenyl, phenyl which is substituted by one or two $C_1$-$C_8$ alkyl groups, $C_5$-$C_9$ cycloalkyl, $C_5$-$C_9$ cycloalkyl which is substituted by one or two $C_1$-$C_8$ alkyl groups, —$X_1$-phenyl, —$X_1$-phenyl which is substituted in the phenyl ring by one or two $C_1$-$C_8$ alkyl groups, $X_1$—$C_5$-$C_9$ cycloalkyl or $X_1$—$C_5$-$C_9$ cycloalkyl which is substituted by one or two $C_1$-$C_8$ alkyl groups; where $X_1$ is $C_1$-$C_{24}$ alkyl which is saturated, monounsaturated or polyunsaturated and straight or branched chain.

Unsubstituted is intended to mean that hydrogen is the only substituent.

Except as described herein, any of the above defined aryl, het, alkyl, alkenyl, alkynyl, or cycloalkyl, may be unsubstituted or independently substituted by up to four, preferably one, two or three substituents, selected from the group consisting of: halo (such as Cl or Br); hydroxy; lower alkyl (such as $C_1$-$C_3$ alkyl); lower alkyl which may be substituted with any of the substituents defined herein; lower alkenyl; lower alkynyl; lower alkanoyl; lower alkoxy (such as methoxy); aryl (such as phenyl or naphthyl); substituted aryl (such as fluoro phenyl or methoxy phenyl); aryl lower alkyl such as benzyl, amino, mono or di-lower alkyl (such as dimethylamino); lower alkanoyl amino acetylamino; amino lower alkoxy (such as ethoxyamine); nitro; cyano; cyano lower alkyl; carboxy; lower carbalkoxy (such as methoxy carbonyl; n-propoxy carbonyl or iso-propoxy carbonyl), lower aryloyl, such as benzoyl; carbamoyl; N-mono- or N,N di-lower alkyl carbamoyl; lower alkyl carbamic acid ester; amidino; guanidine; ureido; mercapto; sulfo; lower alkylthio; sulfoamino; sulfonamide; benzosulfonamide; sulfonate; sulfanyl lower alkyl (such as methyl sulfanyl); sulfoamino; aryl sulfonamide; halogen substituted or unsubstituted aryl sulfonate (such as chloro-phenyl sulfonate); lower alkylsulfinyl; arylsulfinyl; aryl-lower alkylsulfinyl; lower alkylarylsulfinyl; lower alkanesulfonyl; arylsulfonyl; aryl-lower alkylsulfonyl; lower aryl alkyl; lower alkylarylsulfonyl; halogen-lower alkylmercapto; halogen-lower alkylsulfonyl; such as trifluoromethane sulfonyl; phosphono(—P(=O)(OH)$_2$); hydroxy-lower alkoxy phosphoryl or di-lower alkoxyphosphoryl; urea and substituted urea of the formula ($R_9$)NC(O)N($R_{10}$), ($R_{13}$) wherein $R_9$, $R_{10}$ and $R_{13}$ are as defined herein (such as urea or 3-trifluoro-methyl-phenyl urea); alkyl carbamic acid ester or carbamates (such as ethyl-N-phenyl-carbamate) or —N$R_8R_{14}$, wherein $R_8$ and $R_{14}$ can be the same or different and are independently H; lower alkyl (e.g. methyl, ethyl or propyl); or $R_8$ and $R_{14}$ together with the N atom form a 3- to 8-membered heterocyclic ring containing a nitrogen heteroring atom and optionally one or two additional heteroring atoms selected from the group consisting of nitrogen, oxygen and sulfur (e.g. piperazinyl, pyrazinyl, lower alkyl-piperazinyl, pyridyl, indolyl, thiophenyl, thiazolyl, benzothiophenyl, pyrrolidinyl, piperidino or imidazolinyl) where the heterocyclic ring may be substituted with any of the substituents defined hereinabove.

Preferably the above mentioned alkyl, cycloalkyl, and aryl groups are independently unsubstituted or are substituted by lower alkyl, aryl, aryl lower alkyl, carboxy, lower carbalkoxy and especially halogen, —OH, —SH, —OCH$_3$, —SCH$_3$, —CN, —SCN or nitro.

As defined herein the term "lower alkyl", when used alone or in combination refers to alkyl containing 1-6 carbon atoms. The alkyl group may be branched or straight-chained, and is as defined hereinabove.

The term "lower alkenyl" refers to a alkenyl group which contains 2-6 carbon atoms. An alkenyl group is a hydrocarbyl group containing at least one carbon-carbon double bond. As defined herein, it may be unsubstituted or substituted with the substituents described herein. The carbon-carbon double bonds may be between any two carbon atoms of the alkenyl group. It is preferred that it contains 1 or 2 carbon-carbon double bonds and more preferably one carbon-carbon double bond. The alkenyl group may be straight chained or branched. Examples include ethenyl, 1-propenyl, 2-propenyl, 1-butenyl, 2-butenyl, 2-methyl-1-propenyl, 1,3-butadienyl, and the like. The preferred alkenyl group is ethenyl.

The term "lower alkynyl", as used herein, refers to an alkynyl group containing 2-6 carbon atoms. An alkynyl group is a hydrocarbyl group containing at least one carbon-carbon triple bond. The carbon-carbon triple bond may be between any two carbon atom of the alkynyl group. It is preferred that the alkynyl group contains 1 or 2 carbon-carbon triple bonds and more preferably one carbon-carbon triple bond. The alkynyl group may be straight chained or branched. Examples include ethynyl, 1-propynyl, 2-propynyl, 1-butynyl, 2-butynyl and the like. The preferred alkynyl group is ethynyl.

As used herein, the term "aryl alkyl" refers to a aryl group connected to the main chain by a bridging alkylene group. Examples include benzyl, phenethyl, naphthylmethyl, and the like. The preferred aryl alkyl is benzyl. Similarly, cyano alkyl group refers to a cyano group connected to the main chain by a bridging alkylene group.

The term "alkyl aryl" on the other hand, refers to an alkyl group bridged to the main chain through a phenylene group. Examples include methylphenyl, ethylphenyl, and the like.

As used herein, the term lower alkanoyl refers to a lower alkyl chain in which one of the carbon atoms is replaced by a C=O group. The C=O group may be present at one of the ends of the substituent or in the middle of the moiety. Examples include formyl, acetyl, 2-propanoyl, 1-propanoyl and the like.

The term "alkoxy" refers to an alkyl group as defined herein, connected to the main chain by an oxygen atom. Examples include methoxy, ethoxy, and the like.

The term "lower thioalkyl" refers to an alkyl group, as defined herein, connected to the main chain by a sulfur atom. Examples include thiomethyl (or mercapto methyl), thioethyl (mercapto ethyl) and the like.

The term "lower carbalkoxy" or synonym thereto refers to an alkoxycarbonyl group, where the attachment to the main chain is through the aryl group (C(O)). Examples include methoxy carbonyl, ethoxy carbonyl, and the like.

It is to be understood that the terminology C(O) refers to a —C=O group, whether it be ketone, aldehyde or acid or acid derivative. Similarly, S(O) refers to a —S=O group.

As used herein, the term $S(O)_r$ refers to the number of oxygen atoms bonded to the sulfur atom. When r=2, then $S(O)_r=SO_2$, when r is 1, then $S(O)_r$ is SO; and when r=0, then $S(O)_r$ is S.

The term "$C_o$", as used herein, as part of a definition of alkyl, as e.g., $C_{0-10}$, refers to zero carbon atoms. Thus, "$C_0$-$C_{10}$ aryl alkyl" means that the aryl group is bonded directly to the main chain ($C_o$) or that there is a $C_1$-$C_{10}$ alkylene group bridging the main chain to an aryl group.

The term "$(CH_2)_{0-6}$" as part of definition of a larger group, e.g., $(CH_2)_{0-6}$ $C_3$-$C_7$ cycloalkyl, refers to a group that is not present $(CH_2)_0$, or to a group that contains 1-6 carbon atoms $(CH_2)_{1-6}$.

The term $(CH_2)_{0-6}$—$(CH)_{0-1}$, $(aryl)_{1-2}$, in the definition of $R_{11}$ and $R_{12}$, is intended to mean one of the following $(CH_2)_{1-6}$-aryl, aryl, —$CH(aryl)_2$ or $(CH_2)_{1-6}(CH)(aryl)_2$.

As used herein, the variable n refers to number of substitutents on the pyrrolidinyl (tetrahydropyrrolyl) ring. The term "n" is defined as 0-7 and it determines the number of Q substituents on the pyrrolidinyl (tetrahydro-pyrrolyl) ring. Q can only be present at the 2, 3, 4, or 5 positions of the pyrrolidinyl ring, i.e., at the carbon atoms of the pyrrolidinyl ring. Except for carbon number 2 that can allow for one substitution, each of other carbon atoms are saturated and each of them may have two substituents thereon. When n is 7, then each of the carbon atoms are bonded with Q as defined herein. Each Q may be the same or different. However, when n is 6, then one of the seven possible substituents is H, and the other five are Q, which can be the same or different. Further, when n is 5, then two of the possible substitutents are H, and the other five are independently 0, as defined herein. When n is 4, then three of the seven possible substituents are H, and the remainder are Q independently as defined herein. Where n is 3, then four of the seven possible substituents are H, and the other three are Q as defined herein. When n is 2, then two of the seven possible substituent are Q, and the remainder are H. When n is 1, then only one of the seven possible substituent is Q, and the remainder are H. Finally, when n is Q, all seven of the substituents are H.

It is to be understood that each of the Q substituents may be the same or they may be different.

Any asymmetric carbon atom may be present in the (R)-, (S)- or (R,S)-configuration, preferably in the (R)- or (S)-configuration. Substituents at a ring at atoms with saturated bonds or substituents on carbon-carbon double bonds may, if possible, be present in cis-(=Z—) or trans (=E-) form. The compounds may thus be present as mixtures of isomers or preferably as pure isomers, preferably as enantiomercally pure diastereomers or pure enantiomers.

PREFERRED EMBODIMENTS

The preferred $R_1$ group is H and $C_1$-$C_4$ alkyl especially methyl. $R_1$ may be unsubstituted or substituted and is most preferably unsubstituted. The most preferred values of $R_1$ is H, methyl and ethyl, and especially methyl or ethyl and most especially methyl.

$R_2$ is preferably H or $C_1$-$C_4$ alkyl, especially methyl. $R_2$ may be unsubstituted or substituted. It is most preferably unsubstituted. It is preferred that $R_2$ is hydrogen.

$R_3$ and $R_3'$ are, independently, preferably H or $C_1$-$C_4$ alkyl especially hydrogen, methyl, or ethyl and most especially methyl or ethyl, and most especially methyl, which may be unsubstituted or substituted. $R_3$ may be unsubstituted or substituted as defined herein. It is preferred that it is unsubstituted methyl or H. In a most preferred embodiment one of $R_3$ and $R_3'$ is H and the other is methyl.

$R_4$ is preferably $C_5$-$C_7$ cycloalkyl, especially cyclohexyl, or $C_1$-$C_4$ alkyl, especially isopropyl. $R_4$ may be substituted or unsubstituted.

Q is preferably H.

A is a 6-membered heteroaryl or an 8-12 membered fused ring system that may include one 5-7 membered heterocyclic ring containing 1, 2, or 3 heteroring atoms selected from N, O and S. A may be unsubstituted or substituted in any position with one or more Q's. Preferably A is pyridyl, pyrimidinyl, indolyl, benzothiazolyl, or quinolinyl. A may be unsubstituted or substituted. It is preferred that A is unsubstituted or substituted with lower alkyl such as methyl, or halo.

X is aryl, $C_3$-$C_{10}$ cycloalkyl, or het. Preferably X is quinolinyl, isoquinolyl, benzothiazolyl, pyridinyl, indolyl, benzoimidazolyl, naphthyl, benzo[1,3]dioxolyl, benzofurnayl, naphthyridine, pyrrolo[2,3b]pyridinyl, indanzolyl, benzotriazolyl, indazolyl, 2-oxobenzo-oxazolyl, or phenyl. X may be unsubstituted or substituted in any position with one or more Y. Preferably Y is halo especially F or Cl, lower alkyl, especially methyl, ethyl, t-butyl or isopropyl, said lower alkyl may be substituted such as trifluoromethyl, lower alkoxy such as methoxy, lower alkyl amino such as dimethyl amino.

Another embodiment of the compound of Formula I wherein:

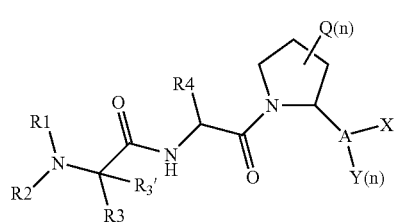

Formula I or pharmaceutically acceptable salts thereof, wherein
$R_1$ is H, $C_1$-$C_4$ alkyl, which $R_1$ may be unsubstituted or substituted;
$R_2$ is H, $C_1$-$C_4$ alkyl, which $R_2$ may be unsubstituted or substituted;
$R_3$ and $R_3'$ are independently H, or $C_1$-$C_4$ alkyl;
$R_4$ is $C_5$-$C_7$ cycloalkyl, especially cyclohexyl, or $C_1$-$C_4$ alkyl, especially isopropyl;
A is a 6 membered heteroaryl ring or an 8-12 membered fused ring system that may include one 5-7 membered heterocyclic ring containing 1, 2, or 3 heteroring atoms selected from N, O and S, which any position of the rings is unsubstituted or substituted with one or more Q's;
Q and Y are independently H, F, Cl, Br, I, $C_1$-$C_{10}$ alkyl, $C_1$-$C_{10}$ alkoxy;
X is aryl, $C_3$-$C_{10}$ cycloalkyl, or het, which may be substituted or unsubstituted.

A preferred embodiment is the compound of Formula I, or pharmaceutically acceptable salts thereof, wherein
$R_1$ is H, or methyl;
$R_2$ is H, or methyl;
one of $R_3$ and $R_3'$ a is H and the other is methyl;
$R_4$ is cyclohexyl, or isopropyl;
A is pyridyl, pyrimidinyl, indolyl, benzothiazolyl, or quinolinyl which may be unsubstituted or substituted with lower alkyl such as methyl, or halo;
Q and Y are independently H, F or Cl, lower alkyl, especially methyl, ethyl, t-butyl or isopropyl, said lower alkyl may be substituted such as trifluoromethyl, lower alkoxy such as methoxy, lower alkyl amino such as dimethyl amino; and X is quinolinyl, isoquinolyl, benzothiazolyl, pyridinyl, indolyl, benzoimidazolyl, naphthyl, benzo[1,3]dioxolyl, benzofurnayl, naphthyridine, pyrrolo[2,3b]pyridinyl, indanzolyl, benzotriazolyl, indazolyl, 2-oxobenzo-oxazolyl, or phenyl, which may be substituted or unsubstituted.

General Procedure

The active compounds of this invention may be prepared as described in the following reaction schemes. Unless otherwise indicated, $R_1$, $R_2$ in the reaction schemes and discussion that follow, are as defined above.

Scheme A

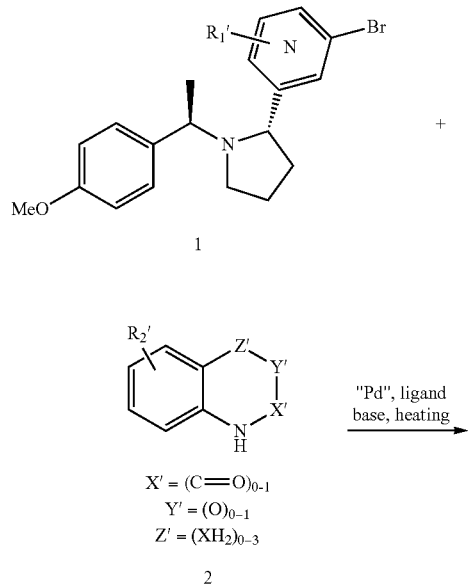

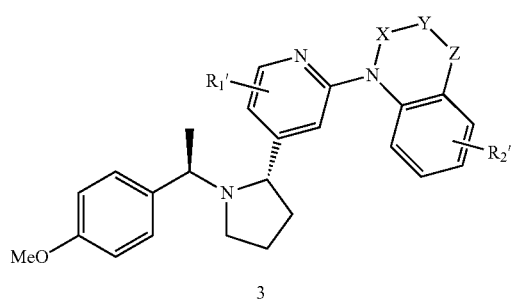

Scheme A illustrates a method for preparing compounds of the formula 3 by reacting a compound of the formula 1 (Int. Pat. Appl. WO2005097791A1), wherein $R_1'$ is either fluorine or methyl, nitrogen could be in any position of the ring, with an excess compound of formula 2. The reaction is run in the presence of a palladium catalyst such as $Pd_2(dba)_3$, a ligand such as 2-(dicyclohexylphosphino)-biphenyl and a base such as potassium tert-butoxide in toluene at a rang of temperature of 70° C. to 100° C., but preferably at around 80° C. The reaction is typically run for a period of 3 hour up to 15 hours but preferably between 3 and 5 hours.

Scheme B

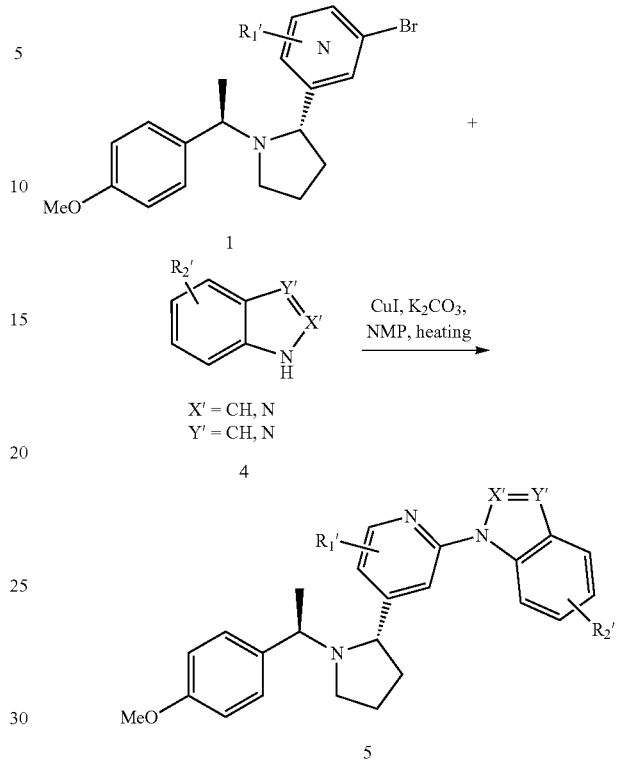

Scheme B illustrates a method for preparing compounds of the formula 5 by reacting a compound of the formula 1 (Int. Pat. Appl. WO2005097791A1), wherein $R'_1$ is either fluorine or methyl, nitrogen could be in any position of the ring, with a compound of formula 4. The reaction typically run in the presence of a base such as potassium carbonate or cesium carbonate. CuI was employed as catalyst in the reaction. The solvent used may be NMP. The temperature of the reaction may vary from 180° C. to 220° C. for a period of 25 min to 60 min in a microwave reaction stove, preferably around 30 min.

Scheme C

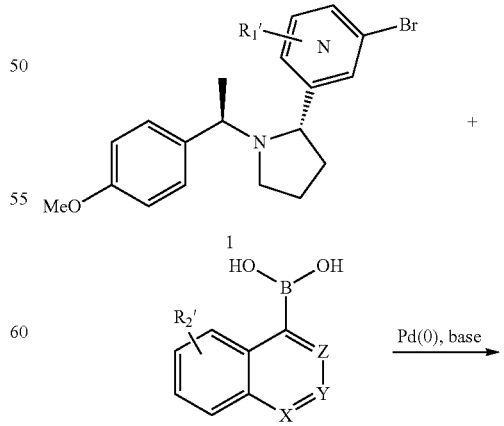

-continued

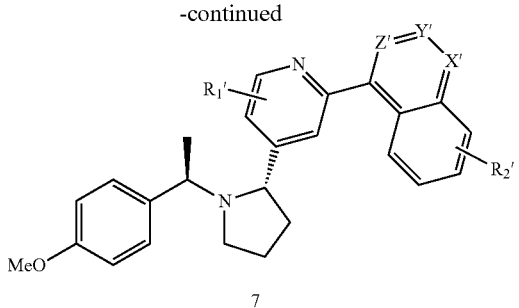

7

Scheme C illustrates a method of Suzuki coupling for preparing compounds of the formula 7 by reacting a compound of the formula 1 (Int. Pat. Appl. WO2005097791A1), wherein $R'_1$ is either fluorine or methyl, nitrogen could be in any position of the ring, with a compound of formula 6. The reaction typically run in the presence of Pd(0) such as $Pd(Ph)_4$ and base such as sodium carbonate, and in a solvent mixture of toluene, ethanol and water. The temperature of the reaction typically is 80° C. Alternatively, compounds of formula 1 may be transformed to boronic acid/ester and couple to heterocyclic bromides similar to formula 6.

TABLE I

| Example | Name | MS ESI $(M + H)^+$ |
|---|---|---|
| 1 | N-{1-Cyclohexyl-2-[2-(1H-indol-3-yl)-pyrrolidin-1-yl]-2-oxo-ethyl}-2-methyl-amino-propionamide | 411.56 |
| 2 | N-{1-Cyclohexyl-2-[2-(1H-indol-3-yl)-pyrrolidin-1-yl]-2-oxo-ethyl}-2-methyl-amino-propionamide | 411.56 |
| 3 | N-{1-Cyclohexyl-2-[2-(1H-indol-2-yl)-pyrrolidin-1-yl]-2-oxo-ethyl}-2-methyl-amino-propionamide | 411.56 |
| 4 | N-(1-Cyclohexyl-2-{2-[2-(2,3-dihydro-indol-1-yl)-pyridin-4-yl]-pyrrolidin-1-yl}-2-oxo-ethyl)-2-methyl-amino-propionamide | 490.67 |

TABLE I-continued

| | Example | Name | MS ESI (M + H)+ |
|---|---|---|---|
| 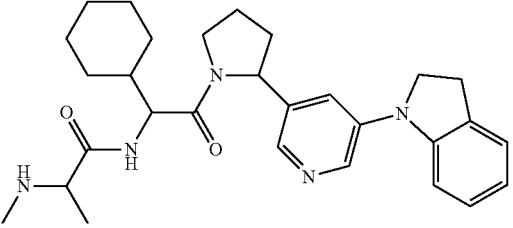 | 5 | N-(1-Cyclohexyl-2-{2-[5-(2,3-dihydro-indol-1-yl)-pyridin-3-yl]-pyrrolidin-1-yl}-2-oxo-ethyl)-2-methylamino-propionamide | 490.67 |
| 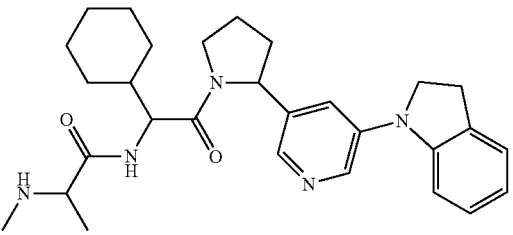 | 6 | N-(1-Cyclohexyl-2-{2-[5-(2,3-dihydro-indol-1-yl)-pyridin-3-yl]-pyrrolidin-1-yl}-2-oxo-ethyl)-2-methylamino-propionamide | 490.67 |
| 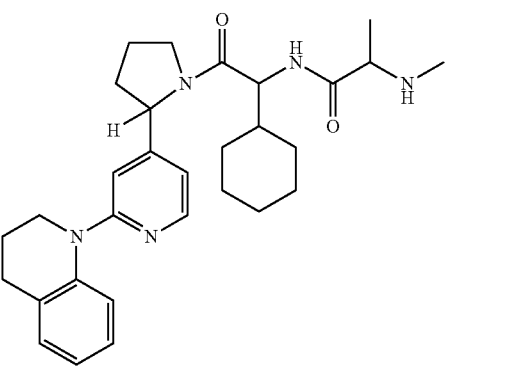 | 7 | N-(1-Cyclohexyl-2-{2-[2-(3,4-dihydro-2H-quinolin-1-yl)-pyridin-4-yl]-pyrrolidin-1-yl}-2-oxo-ethyl)-2-methylamino-propionamide | 504.69 |
| 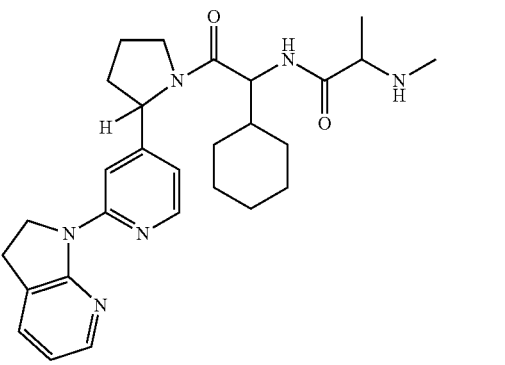 | 8 | N-(1-Cyclohexyl-2-{2-[2-(2,3-dihydro-pyrrolo[2,3-b]pyridin-1-yl)-pyridin-4-yl]-pyrrolidin-1-yl}-oxo-ethyl)-2-methylamino-propionamide | 491.65 |
| 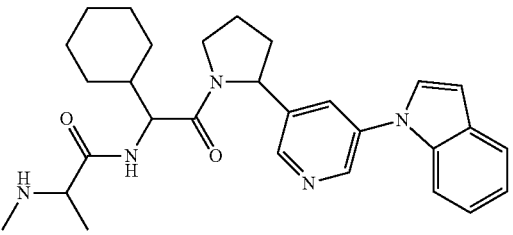 | 9 | N-{1-Cyclohexyl-2-[2-(5-indol-1-yl-pyridin-3-yl)-pyrrolidin-1-yl]-2-oxo-ethyl}-2-methylamino-propionamide | 488.65 |

TABLE I-continued

| | | Example Name | MS ESI (M + H)+ |
|---|---|---|---|
| 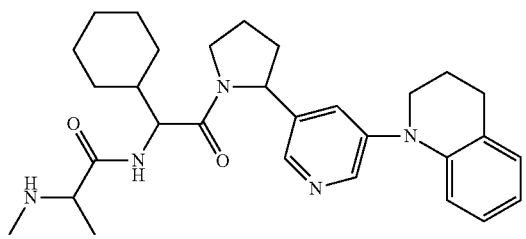 | 10 | N-(1-Cyclohexyl-2-{2-[5-(3,4-dihydro-2H-quinolin-1-yl)-pyridin-3-yl]-pyrrolidin-1-yl}-2-oxo-ethyl)-2-methylamino-propionamide | 504.69 |
| 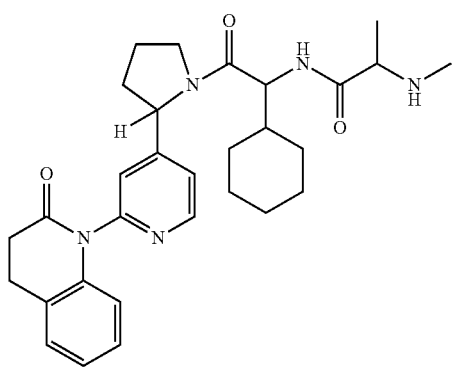 | 11 | N-(1-Cyclohexyl-2-oxo-2-{2-[2-(2-oxo-3,4-dihydro-2H-quinolin-1-yl)-pyridin-4-yl]-pyrrolidin-1-yl}-ethyl)-2-methylamino-propionamide | 518.68 |
| 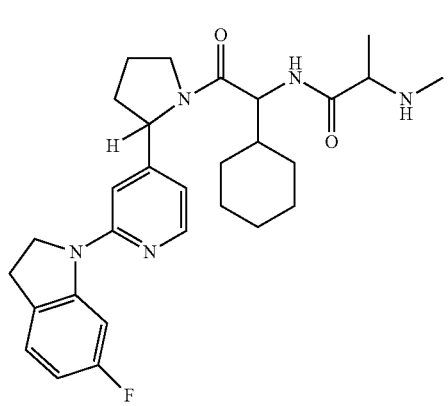 | 12 | N-(1-Cyclohexyl-2-{2-[2-(6-fluoro-2,3-dihydro-indol-1-yl)-pyridin-4-yl]-pyrrolidin-1-yl}-2-oxo-ethyl)-2-methylamino-propionamide | 508.66 |
| 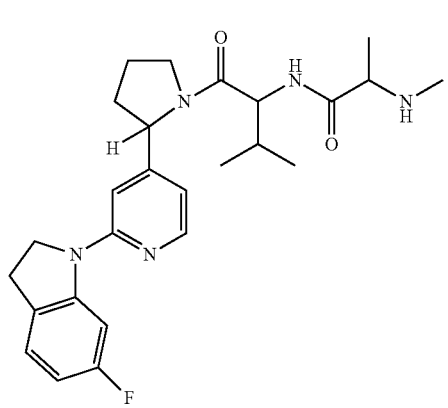 | 13 | N-(1-{2-[2-(6-Fluoro-2,3-dihydro-indol-1-yl)-pyridin-4-yl]-pyrrolidine-1-carbonyl}-2-methyl-propyl)-2-methylamino-propionamide | 468.59 |

TABLE I-continued

| Example | Name | MS ESI (M + H)+ |
|---|---|---|
| 14 | N-{1-Cyclohexyl-2-[2-(2-isoquinolin-4-yl-pyridin-4-yl)-pyrrolidin-1-yl]-2-oxo-ethyl}-2-methylamino-propionamide | 500.66 |
| 15 | N-{1-Cyclohexyl-2-[2-(2-isoquinolin-4-yl-pyridin-4-yl)-pyrrolidin-1-yl]-2-oxo-ethyl}-2-methylamino-propionamide | 500.66 |
| 16 | N-(1-Cyclohexyl-2-{2-[2-(5-fluoro-2,3-dihydro-indol-1-yl)-pyridin-4-yl]-pyrrolidin-1-yl}-2-oxo-ethyl)-2-methylamino-propionamide | 508.66 |
| 17 | N-{1-Cyclohexyl-2-[2-(2-indazol-1-yl-pyridin-4-yl)-pyrrolidin-1-yl]-2-oxo-ethyl}-2-methylamino-propionamide | 489.64 |

TABLE I-continued

| | | Example Name | MS ESI (M + H)+ |
|---|---|---|---|
| 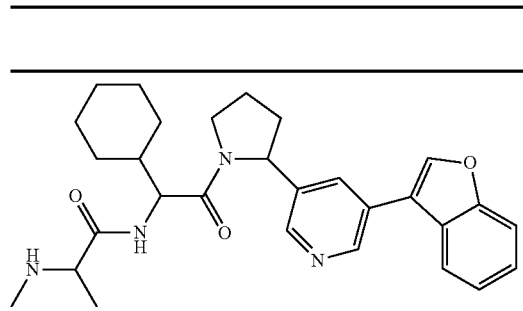 | 18 | N-{2-[2-(5-Benzofuran-3-yl-pyridin-3-yl)-pyrrolidin-1-yl]-1-cyclohexyl-2-oxo-ethyl}-2-methylamino-propionamide | 489.64 |
| 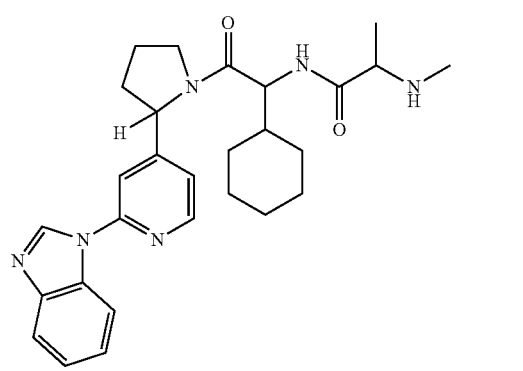 | 19 | N-{2-[2-(2-Benzoimidazol-1-yl-pyridin-4-yl)-pyrrolidin-1-yl]-1-cyclohexyl-2-oxo-ethyl}-2-methylamino-propionamide | 489.64 |
| 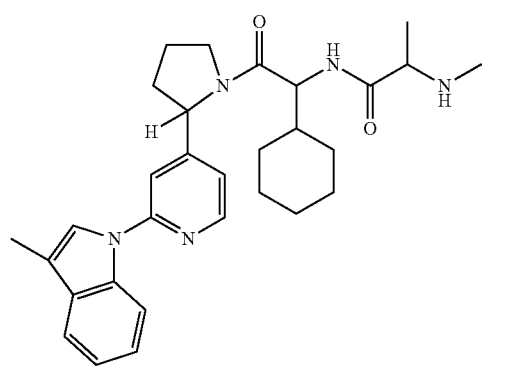 | 20 | N-(1-Cyclohexyl-2-{2-[2-(3-methyl-indol-1-yl)-pyridin-4-yl]-pyrrolidin-1-yl}-2-oxo-ethyl)-2-methylamino-propionamide | 502.68 |
| 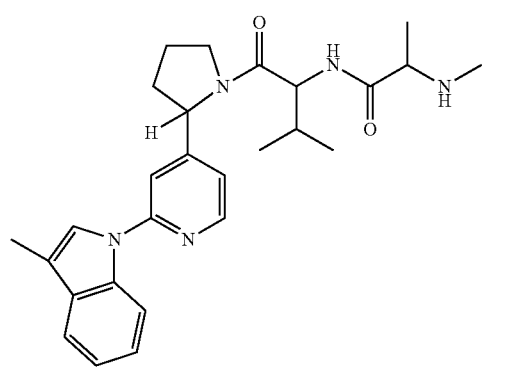 | 21 | 2-Methylamino-N-(2-methyl-1-{2-[2-(3-methyl-indol-1-yl)-pyridin-4-yl]-pyrrolidine-1-carbonyl}-propyl)-propionamide | 462.61 |
| 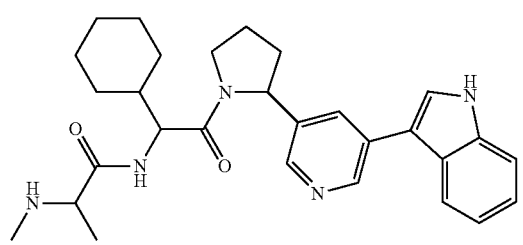 | 22 | N-(1-Cyclohexyl-2-{2-[5-(1H-indol-3-yl)-pyridin-3-yl]-pyrrolidin-1-yl}-2-oxo-ethyl)-2-methylamino-propionamide | 488.65 |

TABLE I-continued

| | Example Name | MS ESI (M + H)+ |
|---|---|---|
| 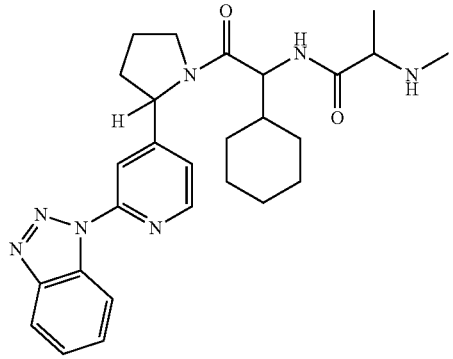 | 23 N-{2-[2-(2-Benzotriazol-1-yl-pyridin-4-yl)-pyrrolidin-1-yl]-1-cyclohexyl-2-oxo-ethyl}-2-methylamino-propionamide | 490.63 |
| 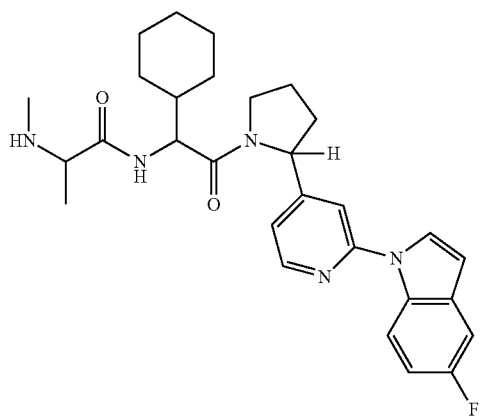 | 24 N-(1-Cyclohexyl-2-{2-[2-(5-fluoro-indol-1-yl)-pyridin-4-yl]-pyrrolidin-1-yl}-2-oxo-ethyl)-2-methylamino-propionamide | 506.64 |
| 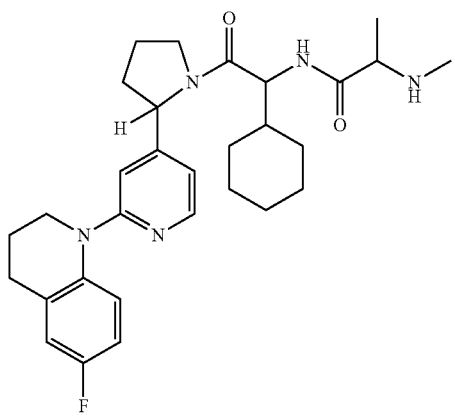 | 25 N-(1-Cyclohexyl-2-{2-[2-(6-fluoro-3,4-dihydro-2H-quinolin-1-yl)-pyridin-4-yl]-pyrrolidin-1-yl}-2-oxo-ethyl)-2-methylamino-propionamide | 522.68 |
| 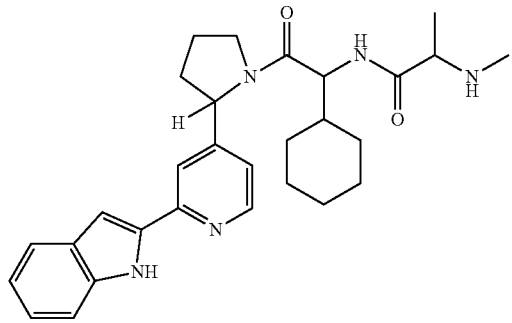 | 26 N-(1-Cyclohexyl-2-{2-[2-(1H-indol-2-yl)-pyridin-4-yl]-pyrrolidin-1-yl}-2-oxo-ethyl)-2-methylamino-propionamide | 488.65 |

TABLE I-continued

| | Example Name | MS ESI (M + H)+ |
|---|---|---|
| 27 | N-(1-Cyclohexyl-2-{2-[5-(5-fluoro-2,3-dihydro-indol-1-yl)-pyridin-3-yl]-pyrrolidin-1-yl}-2-oxo-ethyl)-2-methylamino-propionamide | 508.66 |
| 28 | N-(1-Cyclohexyl-2-{2-[2-(1H-indol-3-yl)-pyridin-4-yl]-pyrrolidin-1-yl}-2-oxo-ethyl)-2-methylamino-propionamide | 488.65 |
| 29 | N-(1-{2-[2-(6-Fluoro-indol-1-yl)-pyridin-4-yl]-pyrrolidine-1-carbonyl}-2-methyl-propyl)-2-methylamino-propionamide | 466.58 |
| 30 | N-(1-Cyclohexyl-2-{-2-[2-(6-fluoro-indol-1-yl)-pyridin-4-yl]-pyrrolidin-1-yl}-2-oxo-ethyl)-2-methylamino-propionamide | 506.64 |

TABLE I-continued

| | | Example Name | MS ESI (M + H)+ |
|---|---|---|---|
| 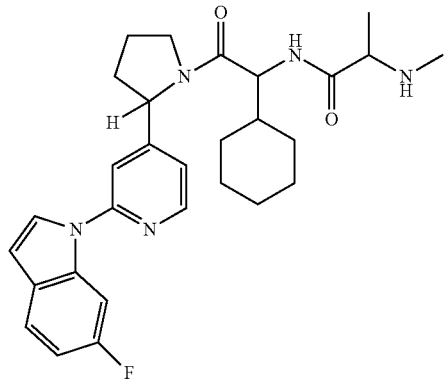 | 31 | N-(1-Cyclohexyl-2-{2-[2-(6-fluoro-indol-1-yl)-pyridin-4-yl]-pyrrolidin-1-yl}-2-oxo-ethyl)-2-methylamino-propionamide | 506.64 |
| 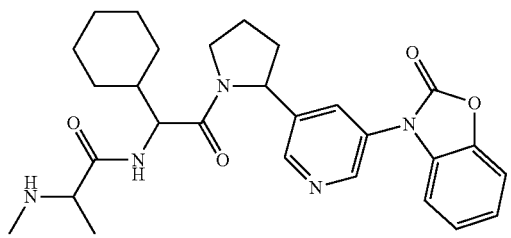 | 32 | N-(1-Cyclohexyl-2-oxo-2-{2-[5-(2-oxo-benzooxazol-3-yl)-pyridin-3-yl]-pyrrolidin-1-yl}-ethyl)-2-methylamino-propionamide | 506.62 |
| 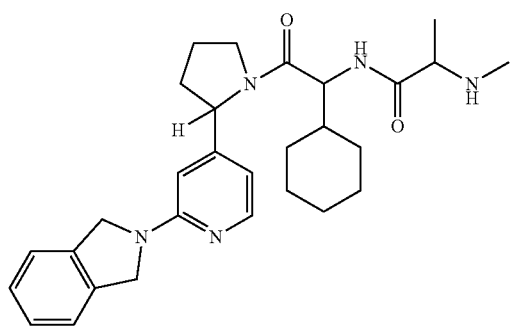 | 33 | N-(1-Cyclohexyl-2-{2-[2-(1,3-dihydro-isoindol-2-yl)-pyridin-4-yl]-pyrrolidin-1-yl}-2-oxo-ethyl)-2-methylamino-propionamide | 490.67 |
| 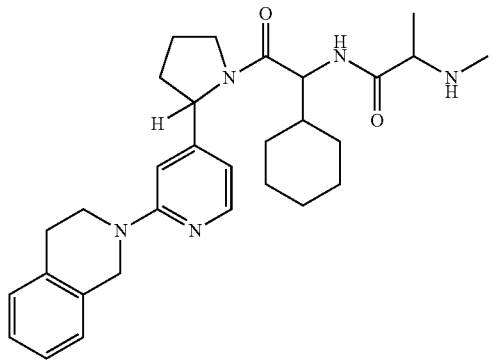 | 34 | N-(1-Cyclohexyl-2-{2-[2-(3,4-dihydro-1H-isoquinolin-2-yl)-pyridin-4-yl]-pyrrolidin-1-yl}-2-oxo-ethyl)-2-methylamino-propionamide | 504.69 |

TABLE I-continued

| | Example | Name | MS ESI (M + H)+ |
|---|---|---|---|
| | 35 | N-{2-[2-(5-Benzoimidazol-1-yl-pyridin-3-yl)-pyrrolidin-1-yl]-1-cyclohexyl-2-oxo-ethyl}-2-methylamino-propionamide | 489.64 |
| | 36 | N-{2-[2-(5-Benzotriazol-1-yl-pyridin-3-yl)-pyrrolidin-1-yl]-1-cyclohexyl-2-oxo-ethyl}-2-methylamino-propionamide | 490.63 |
| | 37 | N-{1-Cyclohexyl-2-[2-(5-indazol-1-yl-pyridin-3-yl)-pyrrolidin-1-yl]-2-oxo-ethyl}-2-methylamino-propionamide | 489.64 |
| | 38 | N-(1-Cyclohexyl-2-{2-[2-(5-fluoro-3-methyl-indol-1-yl)-pyridin-4-yl]-pyrrolidin-1-yl}-2-oxo-ethyl)-2-methylamino-propionamide | 520.67 |

TABLE I-continued

| | Example Name | MS ESI (M + H)+ |
|---|---|---|
| 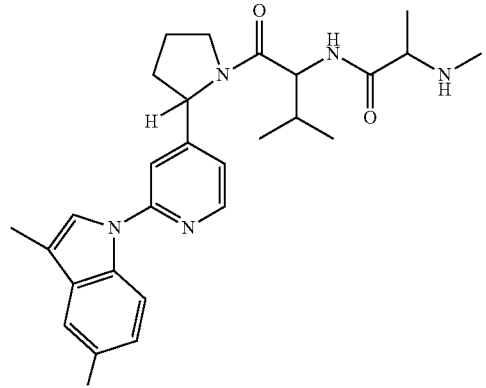 39 | N-(1-{2-[2-(5-Fluoro-3-methyl-indol-1-yl)-pyridin-4-yl]-pyrrolidine-1-carbonyl}-2-methyl-propyl)-2-methylamino-propionamide | 480.6 |
| 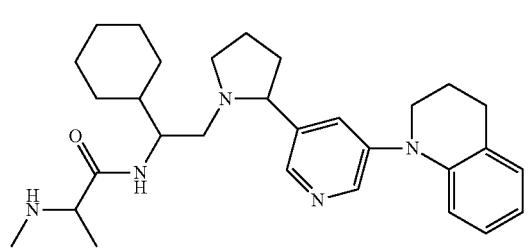 40 | N-(1-Cyclohexyl-2-{2-[5-(3,4-dihydro-2H-quinolin-1-yl)-pyridin-3-yl]-pyrrolidin-1-yl}-ethyl)-2-methylamino-propionamide | 490.71 |
| 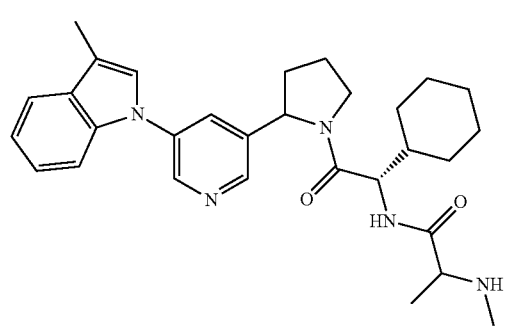 41 | N-(1-Cyclohexyl-2-{2-[5-(3-methyl-indol-1-yl)-pyridin-3-yl]-pyrrolidin-1-yl}-2-oxo-ethyl)-2-methylamino-propionamide | 502.68 |
| 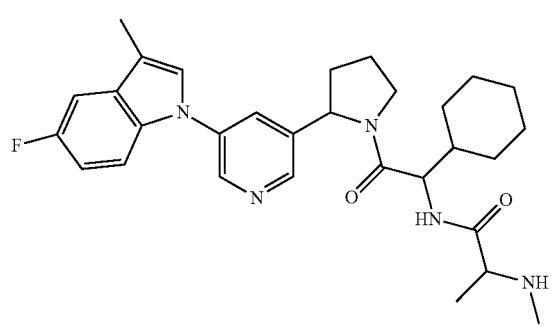 42 | N-(1-Cyclohexyl-2-{2-[5-(5-fluoro-3-methyl-indol-1-yl)-pyridin-3-yl]-pyrrolidin-1-yl}-2-oxo-ethyl)-2-methylamino-propionamide | 520.67 |
| 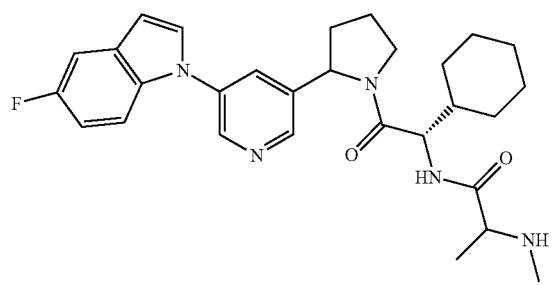 43 | N-(1-Cyclohexyl-2-{2-[5-(5-fluoro-indol-1-yl)-pyridin-3-yl]-pyrrolidin-1-yl}-2-oxo-ethyl)-2-methylamino-propionamide | 506.64 |

TABLE I-continued

| | Example | Name | MS ESI (M + H)+ |
|---|---|---|---|
| | 44 | N-{1-Cyclohexyl-2-oxo-2-[2-(5-pyrrolo[2,3-b]pyridin-1-yl-pyridin-3-yl)-pyrrolidin-1-yl]-ethyl}-2-methylamino-propionamide | 489.64 |
| | 45 | N-{2-[2-(2-Benzoimidazol-1-yl-3-fluoro-pyridin-4-yl)-pyrrolidin-1-yl]-1-cyclohexyl-2-oxo-ethyl}-2-methylamino-propionamide | 507.63 |
| | 46 | N-{1-[2-(2-Benzoimidazol-1-yl-pyridin-4-yl)-pyrrolidine-1-carbonyl]-2-methyl-propyl}-2-methylamino-propionamide | 449.57 |
| | 47 | 3-(5-{1-[2-Cyclohexyl-2-(2-methylamino-propionylamino)-acetyl]-pyrrolidin-2-yl}-pyridin-3-yl)-indole-1-carboxylic acid dimethylamide | 559.73 |

TABLE I-continued

| | Example Name | MS ESI (M + H)+ |
|---|---|---|
| 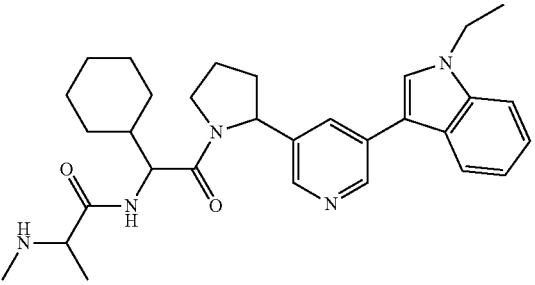 48 | N-(1-Cyclohexyl-2-{2-[5-(1-ethyl-1H-indol-3-yl)-pyridin-3-yl]-pyrrolidin-1-yl}-2-oxo-ethyl)-2-methylamino-propionamide | 516.7 |
| 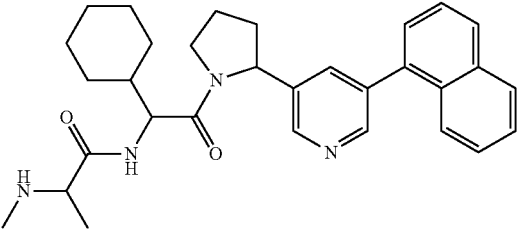 49 | N-{1-Cyclohexyl-2-[2-(5-naphthalen-1-yl-pyridin-3-yl)-pyrrolidin-1-yl]-2-oxo-ethyl}-2-methylamino-propionamide | 499.67 |
| 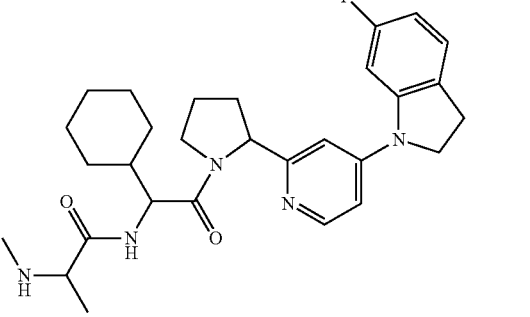 50 | N-(1-Cyclohexyl-2-{2-[4-(6-fluoro-2,3-dihydro-indol-1-yl)-pyridin-2-yl]-pyrrolidin-1-yl}-2-oxo-ethyl)-2-methylamino-propionamide | 508.66 |
| 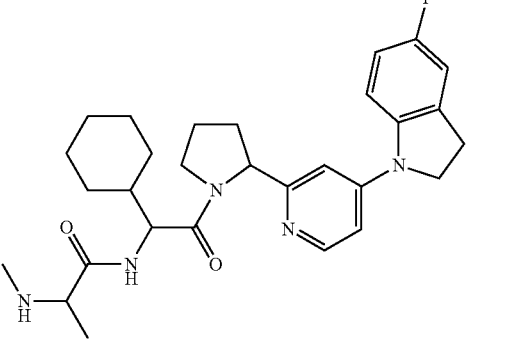 51 | N-(1-Cyclohexyl-2-{2-[4-(5-fluoro-2,3-dihydro-indol-1-yl)-pyridin-2-yl]-pyrrolidin-1-yl}-2-oxo-ethyl)-2-methylamino-propionamide | 508.66 |
| 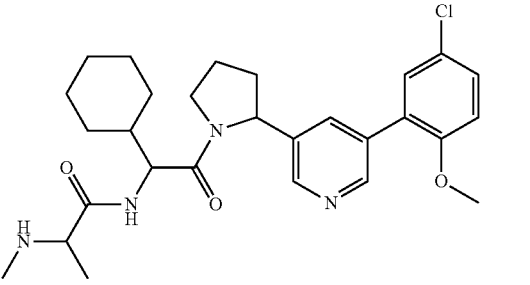 52 | N-(2-{2-[5-(5-Chloro-2-methoxy-phenyl)-pyridin-3-yl]-pyrrolidin-1-yl}-1-cyclohexyl-2-oxo-ethyl)-2-methylamino-propionamide | 514.09 |

TABLE I-continued

| | | Example Name | MS ESI (M + H)+ |
|---|---|---|---|
| 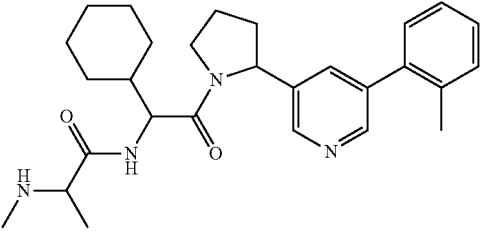 | 53 | N-{1-Cyclohexyl-2-oxo-2-[2-(5-o-tolyl-pyridin-3-yl)-pyrrolidin-1-yl]-ethyl}-2-methylamino-propionamide | 463.64 |
| 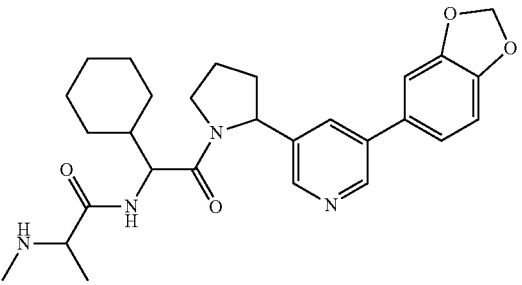 | 54 | N-{2-[2-(5-Benzo[1,3]dioxol-5-yl-pyridin-3-yl)-pyrrolidin-1-yl]-1-cyclohexyl-2-oxo-ethyl}-2-methylamino-propionamide | 493.62 |
| 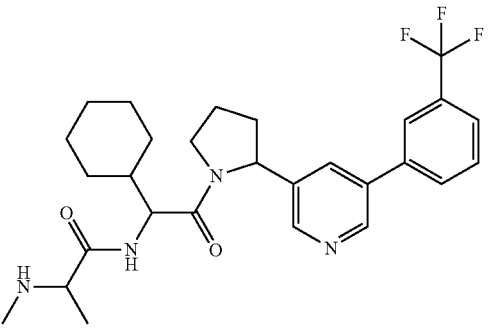 | 55 | N-(1-Cyclohexyl-2-oxo-2-{2-[5-(3-trifluoromethyl-phenyl)-pyridin-3-yl]-pyrrolidin-1-yl}-ethyl)-2-methylamino-propionamide | 517.61 |
| 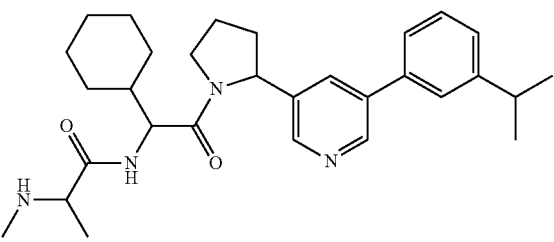 | 56 | N-(1-Cyclohexyl-2-{2-[5-(3-isopropyl-phenyl)-pyridin-3-yl]-pyrrolidin-1-yl}-2-oxo-ethyl)-2-methylamino-propionamide | 491.69 |
| 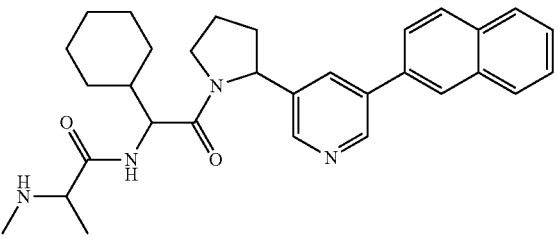 | 57 | N-{1-Cyclohexyl-2-[2-(5-naphthalen-2-yl-pyridin-3-yl)-pyrrolidin-1-yl]-2-oxo-ethyl}-2-methylamino-propionamide | 499.67 |

TABLE I-continued

| | Example | Name | MS ESI (M + H)+ |
|---|---|---|---|
| | 58 | N-{1-Cyclohexyl-2-oxo-2-[2-(7-phenyl-4,5,6,7-tetrahydro-benzothiazol-2-yl)-pyrrolidin-1-yl]-ethyl}-2-methylamino-propionamide | 509.73 |
| | 59 | N-{1-Cyclohexyl-2-oxo-2-[2-(1-phenyl-isoquinolin-7-yl)-pyrrolidin-1-yl]-ethyl}-2-methylamino-propionamide | 499.67 |
| | 60 | N-{1-Cyclohexyl-2-oxo-2-[2-(7-phenyl-6,7-dihydro-5H-[2]pyrindin-4-yl)-pyrrolidin-1-yl]-ethyl}-2-methylamino-propionamide | 489.68 |
| | 61 | N-{1-Cyclohexyl-2-oxo-2-[2-(5-phenyl-5,6,7,8-tetrahydro-quinolin-3-yl)-pyrrolidin-1-yl]-ethyl}-2-methylamino-propionamide | 503.71 |
| | 62 | N-(1-Cyclohexyl-2-{2-[7-(4-fluoro-phenyl)-benzothiazol-2-yl]-pyrrolidin-1-yl}-2-oxo-ethyl)-2-methylamino-propionamide | 523.69 |

TABLE I-continued

| Example | Name | MS ESI (M + H)+ |
|---|---|---|
| 63 | N-(2-{2-[2-Chloro-5-(3-trifluoromethyl-phenyl)-pyridin-3-yl]-pyrrolidin-1-yl}-1-cyclohexyl-2-oxo-ethyl)-2-methylamino-propionamide | 551.24 |
| 64 | N-(2-{2-[5-(3,5-Bis-trifluoromethyl-phenyl)-pyridin-3-yl]-pyrrolidin-1-yl}-1-cyclohexyl-2-oxo-ethyl)-2-methylamino-propionamide | 585.27 |
| 65 | N-(1-Cyclohexyl-2-oxo-2-{2-[5-(2-trifluoromethyl-phenyl)-pyridin-3-yl]-pyrrolidin-1-yl}-ethyl)-2-methylamino-propionamide | 517.28 |
| 66 | N-(1-Cyclohexyl-2-{2-[5-(3,5-dimethyl-phenyl)-pyridin-3-yl]-pyrrolidin-1-yl}-2-oxo-ethyl)-2-methylamino-propionamide | 477.32 |
| 67 | N-(2-{2-[5-(4-tert-Butyl-phenyl)-pyridin-3-yl]-pyrrolidin-1-yl}-1-cyclohexyl-2-oxo-ethyl)-2-methylamino-propionamide | 505.35 |

TABLE I-continued

| | | Example Name | MS ESI (M + H)+ |
|---|---|---|---|
| 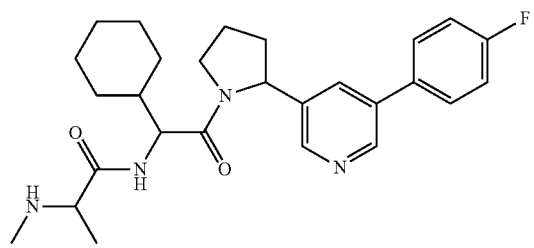 | 68 | N-(1-Cyclohexyl-2-{2-[5-(4-fluoro-phenyl)-pyridin-3-yl]-pyrrolidin-1-yl}-2-oxo-ethyl)-2-methylamino-propionamide | 467.28 |
| 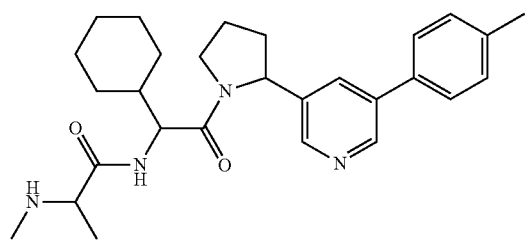 | 69 | N-{1-Cyclohexyl-2-oxo-2-[2-(5-p-tolyl-pyridin-3-yl)-pyrrolidin-1-yl]-ethyl}-2-methylamino-propionamide | 463.31 |
| 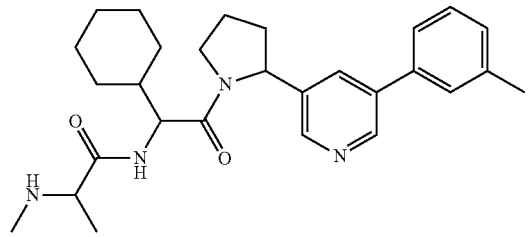 | 70 | N-{1-Cyclohexyl-2-oxo-2-[2-(5-m-tolyl-pyridin-3-yl)-pyrrolidin-1-yl]-ethyl}-2-methylamino-propionamide | 463.31 |
| 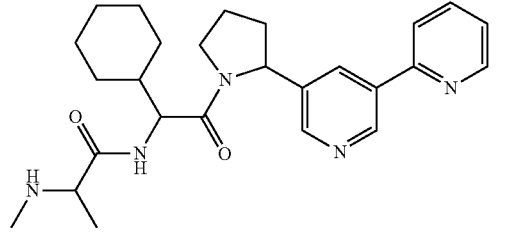 | 71 | N-[2-(2-[2,3']Bipyridinyl-5'-yl-pyrrolidin-1-yl)-1-cyclohexyl-2-oxo-ethyl]-2-methylamino-propionamide | 450.29 |
| 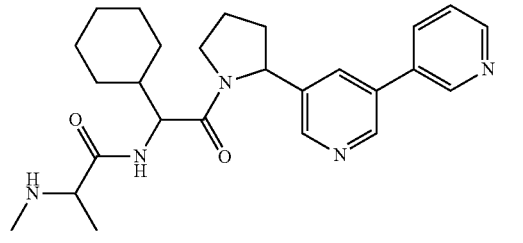 | 72 | N-[2-(2-[3,3']Bipyridinyl-5-yl-pyrrolidin-1-yl)-1-cyclohexyl-2-oxo-ethyl]-2-methylamino-propionamide | 450.29 |
| 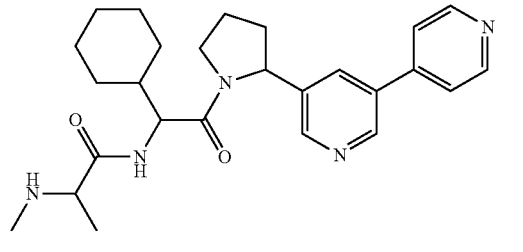 | 73 | N-[2-(2-[3,4']Bipyridinyl-5-yl-pyrrolidin-1-yl)-1-cyclohexyl-2-oxo-ethyl]-2-methylamino-propionamide | 450.29 |

TABLE I-continued

| | Example Name | MS ESI (M + H)+ |
|---|---|---|
| 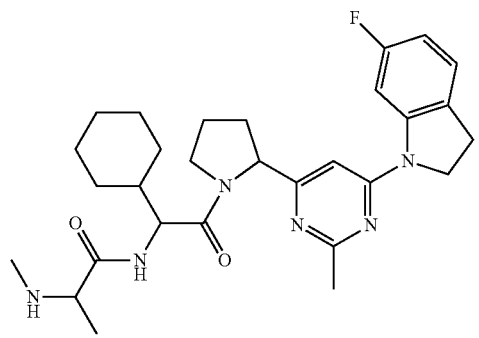 | 74 N-(1-Cyclohexyl-2-{2-[6-(6-fluoro-2,3-dihydro-indol-1-yl)-2-methyl-pyrimidin-4-yl]-pyrrolidin-1-yl}-2-oxo-ethyl)-2-methylamino-propionamide | 523.32 |
| 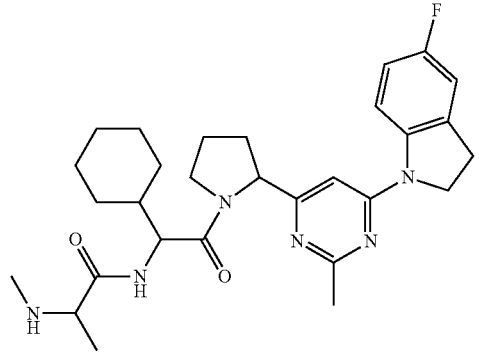 | 75 N-(1-Cyclohexyl-2-{2-[6-(5-fluoro-2,3-dihydro-indol-1-yl)-2-methyl-pyrimidin-4-yl]-pyrrolidin-1-yl}-2-oxo-ethyl)-2-methylamino-propionamide | 523.32 |
| 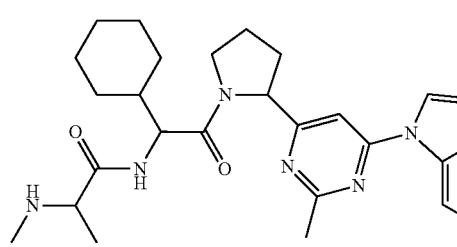 | 76 N-{1-Cyclohexyl-2-[2-(6-indol-1-yl-2-methyl-pyrimidin-4-yl)-pyrrolidin-1-yl]-2-oxo-ethyl}-2-methylamino-propionamide | 503.21 |
| 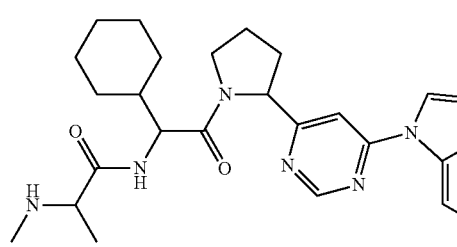 | 77 N-{1-Cyclohexyl-2-[2-(6-indol-1-yl-pyrimidin-4-yl)-pyrrolidin-1-yl]-2-oxo-ethyl}-2-methylamino-propionamide | 489.3 |
| 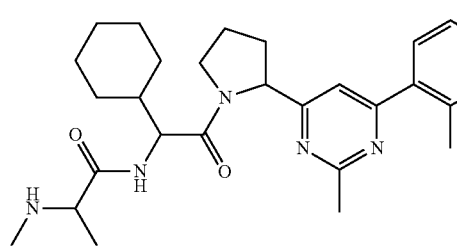 | 78 N-{1-Cyclohexyl-2-[2-(2-methyl-6-o-tolyl-pyrimidin-4-yl)-pyrrolidin-1-yl]-2-oxo-ethyl}-2-methylamino-propionamide | 478.32 |

TABLE I-continued

| | Example Name | MS ESI (M + H)+ |
|---|---|---|
| 79 | N-{1-Cyclohexyl-2-oxo-2-[2-(6-o-tolyl-pyrimidin-4-yl)-pyrrolidin-1-yl]-ethyl}-2-methylamino-propionamide | 464.3 |
| 80 | N-(1-Cyclohexyl-2-{2-[2-methyl-6-(3-methyl-indol-1-yl)-pyrimidin-4-yl]-pyrrolidin-1-yl}-2-oxo-ethyl)-2-methylamino-propionamide | 517.33 |
| 81 | N-(1-Cyclohexyl-2-{2-[2-methyl-6-(3-trifluoromethyl-phenyl)-pyrimidin-4-yl]-pyrrolidin-1-yl}-2-oxo-ethyl)-2-methylamino-propionamide | 532.29 |
| 82 | N-{2-[2-(6-Benzoimidazol-1-yl-2-methyl-pyrimidin-4-yl)-pyrrolidin-1-yl]-1-cyclohexyl-2-oxo-ethyl}-2-methylamino-propionamide | 504.31 |
| 83 | N-{1-Cyclohexyl-2-[2-(2-methyl-6-naphthalen-1-yl-pyrimidin-4-yl)-pyrrolidin-1-yl]-2-oxo-ethyl}-2-methylamino-propionamide | 514.32 |

TABLE I-continued

| | Example Name | MS ESI (M + H)+ |
|---|---|---|
| 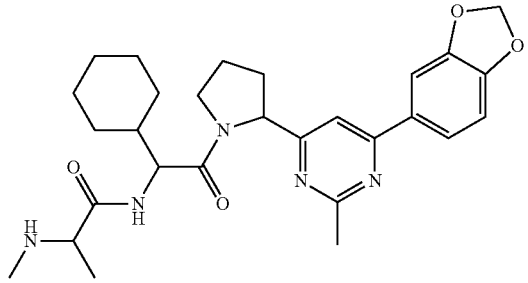 | 84 N-{2-[2-(6-Benzo[1,3]dioxol-5-yl-2-methyl-pyrimidin-4-yl)-pyrrolidin-1-yl]-1-cyclohexyl-2-oxo-ethyl}-2-methylamino-propionamide | 508.29 |
| 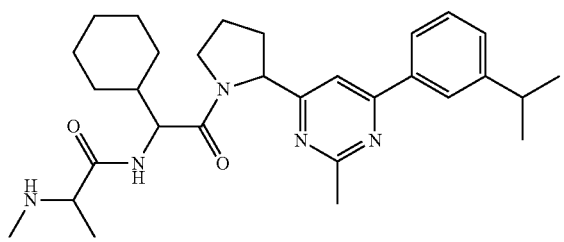 | 85 N-(1-Cyclohexyl-2-{2-[6-(3-isopropyl-phenyl)-2-methyl-pyrimidin-4-yl]-pyrrolidin-1-yl}-2-oxo-ethyl)-2-methylamino-propionamide | 506.35 |
| 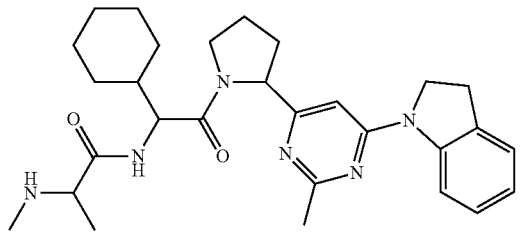 | 86 N-(1-Cyclohexyl-2-{2-[6-(2,3-dihydro-indol-1-yl)-2-methyl-pyrimidin-4-yl]-pyrrolidin-1-yl}-2-oxo-ethyl)-2-methylamino-propionamide | 505.33 |
| 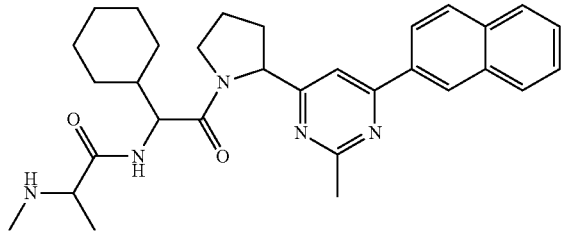 | 87 N-{1-Cyclohexyl-2-[2-(2-methyl-6-naphthalen-2-yl-pyrimidin-4-yl)-pyrrolidin-1-yl]-2-oxo-ethyl}-2-methylamino-propionamide | 504.32 |
| 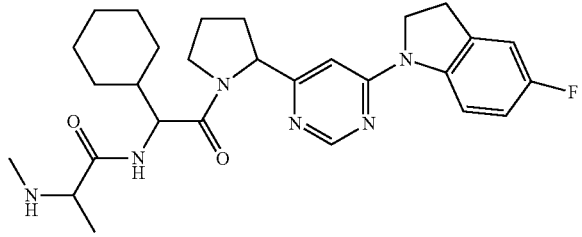 | 88 N-(1-Cyclohexyl-2-{2-[6-(5-fluoro-2,3-dihydro-indol-1-yl)-pyrimidin-4-yl]-pyrrolidin-1-yl}-2-oxo-ethyl)-2-methylamino-propionamide | 509.3 |
| 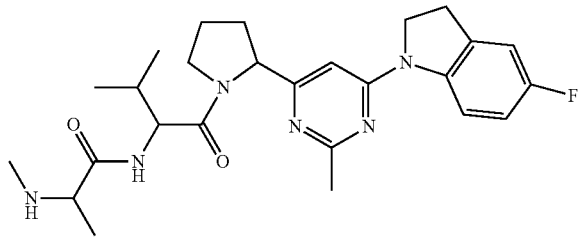 | 89 N-(1-{2-[6-(5-Fluoro-2,3-dihydro-indol-1-yl)-2-methyl-pyrimidin-4-yl]-pyrrolidine-1-carbonyl}-2-methyl-propyl)-2-methylamino-propionamide | 483.29 |

TABLE I-continued

| | | Example Name | MS ESI (M + H)+ |
|---|---|---|---|
| 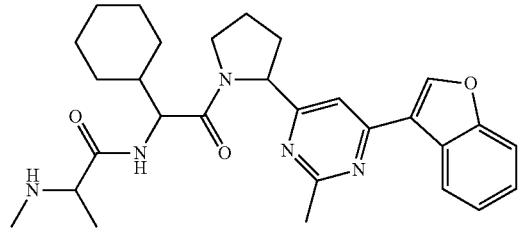 | 90 | N-{2-[2-(6-Benzofuran-3-yl-2-methyl-pyrimidin-4-yl)-pyrrolidin-1-yl]-1-cyclohexyl-2-oxo-ethyl}-2-methylamino-propionamide | 504.3 |
| 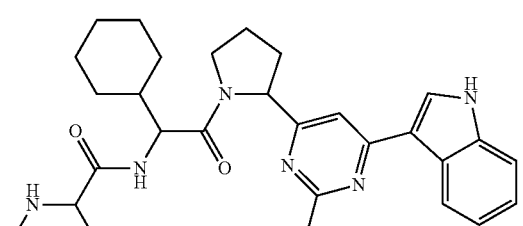 | 91 | N-(1-Cyclohexyl-2-{2-[6-(1H-indol-3-yl)-2-methyl-pyrimidin-4-yl]-pyrrolidin-1-yl}-2-oxo-ethyl)-2-methylamino-propionamide | 503.31 |
| 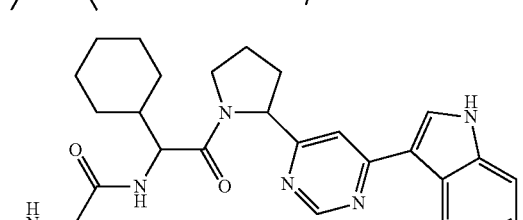 | 92 | N-(1-Cyclohexyl-2-{2-[6-(1H-indol-3-yl)-pyrimidin-4-yl]-pyrrolidin-1-yl}-2-oxo-ethyl)-2-methylamino-propionamide | 489.3 |
| 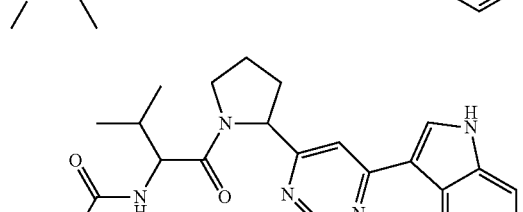 | 93 | N-(1-{2-[6-(1H-Indol-3-yl)-2-methyl-pyrimidin-4-yl]-pyrrolidine-1-carbonyl}-2-methyl-propyl)-2-methylamino-propionamide | 463.28 |
| 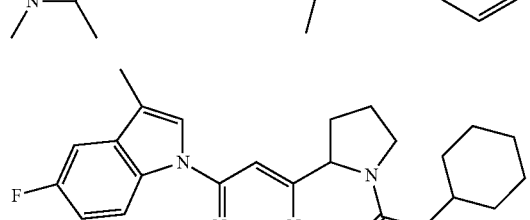 | 94 | N-(1-Cyclohexyl-2-{2-[6-(5-fluoro-3-methyl-indol-1-yl)-2-methyl-pyrimidin-4-yl]-pyrrolidin-1-yl}-2-oxo-ethyl)-2-methylamino-propionamide | 535.32 |
| 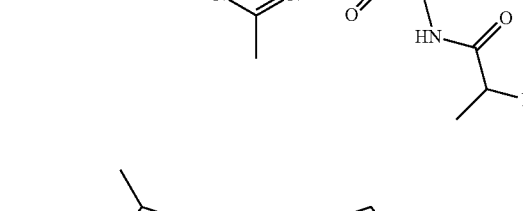 | 95 | N-(1-{2-[6-(5-Fluoro-3-methyl-indol-1-yl)-2-methyl-pyrimidin-4-yl]-pyrrolidine-1-carbonyl}-2-methyl-propyl)-2-methylamino-propionamide | 495.29 |

TABLE I-continued

| | Example | Name | MS ESI (M + H)+ |
|---|---|---|---|
| | 96 | N-(1-Cyclohexyl-2-{2-[6-(5-fluoro-3-methyl-indol-1-yl)-pyrimidin-4-yl]-pyrrolidin-1-yl}-2-oxo-ethyl)-2-methylamino-propionamide | 521.3 |
| | 97 | N-(1-Cyclohexyl-2-{2-[6-(5-fluoro-indol-1-yl)-2-methyl-pyrimidin-4-yl]-pyrrolidin-1-yl}-2-oxo-ethyl)-2-methylamino-propionamide | 521.3 |
| | 98 | N-(1-{2-[6-(5-Fluoro-indol-1-yl)-2-methyl-pyrimidin-4-yl]-pyrrolidine-1-carbonyl}-2-methyl-propyl)-2-methylamino-propionamide | 481.27 |
| | 99 | N-(1-Cyclohexyl-2-{2-[6-(5-fluoro-indol-1-yl)-pyrimidin-4-yl]-pyrrolidin-1-yl}-2-oxo-ethyl)-2-methylamino-propionamide | 507.29 |
| | 100 | 3-(6-{1-[2-Cyclohexyl-2-(2-methylamino-propionylamino)-acetyl]-pyrrolidin-2-yl}-2-methyl-pyrimidin-4-yl)-indole-1-carboxylic acid dimethylamide | 574.35 |

TABLE I-continued

| structure | | Example Name | MS ESI (M + H)+ |
|---|---|---|---|
| 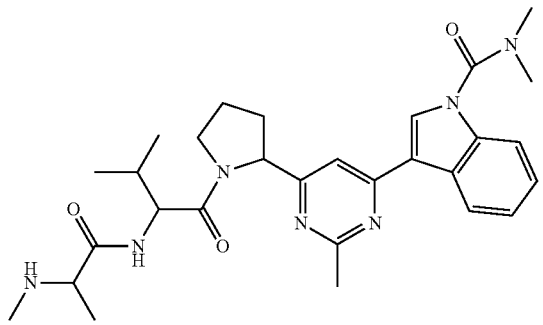 | 101 | 3-(2-Methyl-6-{1-[3-methyl-2-(2-methylamino-propionylamino)-butyryl]-pyrrolidin-2-yl}-pyrimidin-4-yl)-indole-1-carboxylic acid dimethylamide | 534.32 |
| 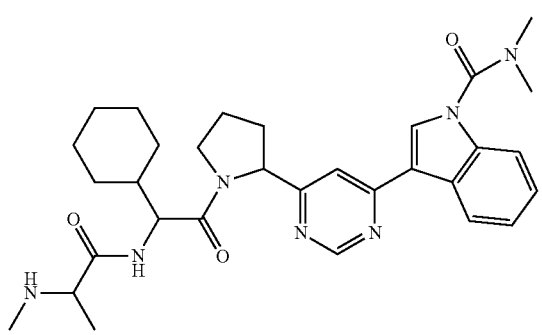 | 102 | 3-(6-{1-[2-Cyclohexyl-2-(2-methylamino-propionylamino)-acetyl]-pyrrolidin-2-yl}-pyrimidin-4-yl)-indole-1-carboxylic acid dimethylamide | 560.33 |
| 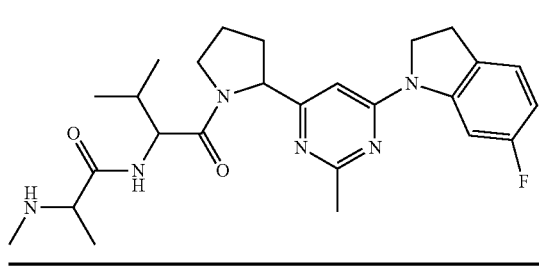 | 103 | N-(1-{2-[6-(6-Fluoro-2,3-dihydro-indol-1-yl)-2-methyl-pyrimidin-4-yl]-pyrrolidine-1-carbonyl}-2-methyl-propyl)-2-methylamino-propionamide | 483.29 |

TABLE 2

| structure | | Example name | MS ESI (M + H)+ |
|---|---|---|---|
| 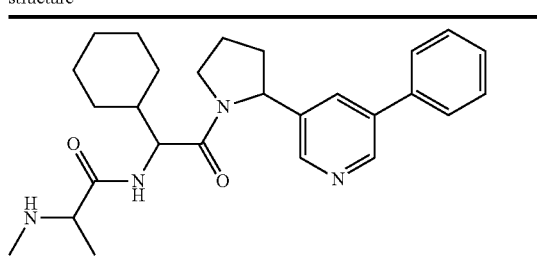 | 104 | N-{1-Cyclohexyl-2-oxo-2-[2-(5-phenyl-pyridin-3-yl)-pyrrolidin-1-yl]-ethyl}-2-methylamino-propionamide | 449.29 |
| 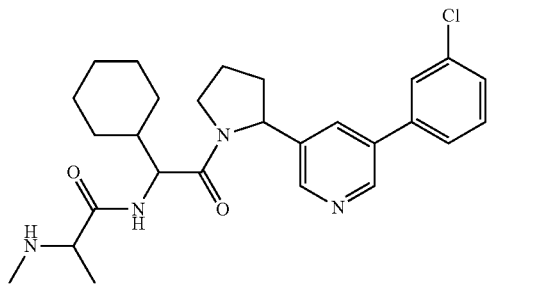 | 105 | N-(2-{2-[5-(3-Chloro-phenyl)-pyridin-3-yl]-pyrrolidin-1-yl}-1-cyclohexyl-2-oxo-ethyl)-2-methylamino-propionamide | 483.25 |

TABLE 2-continued

| structure | Example name | | MS ESI (M + H)+ |
|---|---|---|---|
| 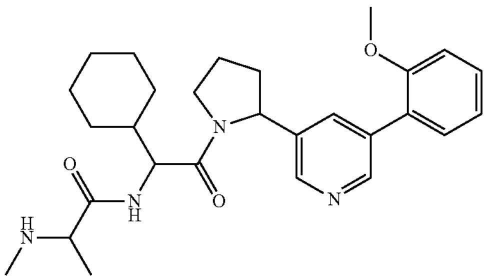 | 106 | N-(1-Cyclohexyl-2-{2-[5-(2-methoxy-phenyl)-pyridin-3-yl]-pyrrolidin-1-yl}-2-oxo-ethyl)-2-methylamino-propionamide | 479.3 |
| 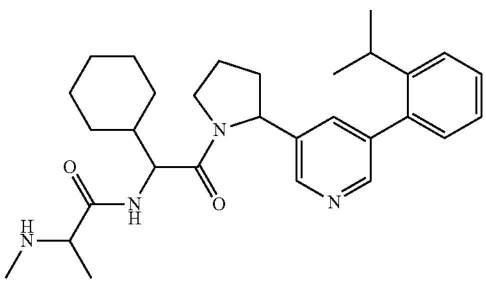 | 107 | N-(1-Cyclohexyl-2-{2-[5-(2-isopropyl-phenyl)-pyridin-3-yl]-pyrrolidin-1-yl}-2-oxo-ethyl)-2-methylamino-propionamide | 491.34 |
| 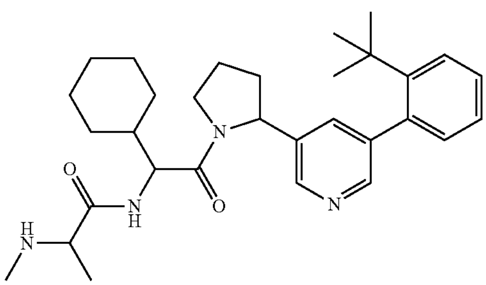 | 108 | N-(2-{2-[5-(2-tert-Butyl-phenyl)-pyridin-3-yl]-pyrrolidin-1-yl}-1-cyclo-hexyl-2-oxo-ethyl)-2-methylamino-propionamide | 505.35 |
| 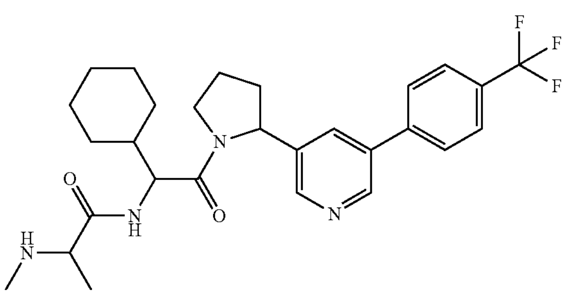 | 109 | N-(1-Cyclohexyl-2-oxo-2-{2-[5-(4-trifluoromethyl-phenyl)-pyridin-3-yl]-pyrrolidin-1-yl}-ethyl)-2-methyl-amino-propionamide | 517.28 |
| 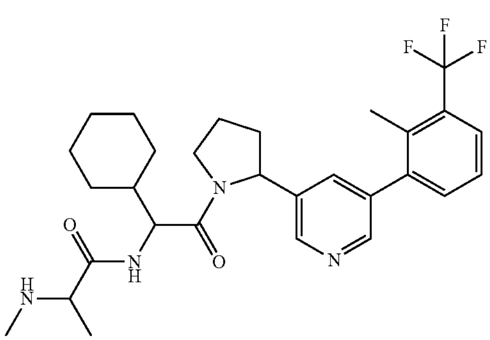 | 110 | N-(1-Cyclohexyl-2-{2-[5-(2-methyl-3-trifluoromethyl-phenyl)-pyridin-3-yl]-pyrrolidin-1-yl}-2-oxo-ethyl)-2-methylamino-propionamide | 531.29 |

TABLE 2-continued

| structure | Example | name | MS ESI (M + H)+ |
|---|---|---|---|
| 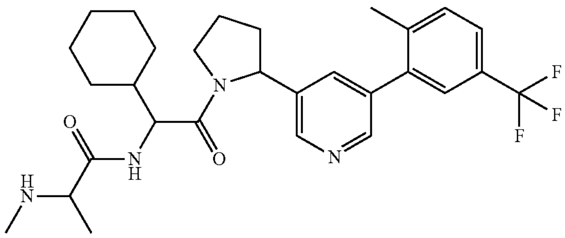 | 111 | N-(1-Cyclohexyl-2-{2-[5-(2-methyl-5-trifluoromethyl-phenyl)-pyridin-3-yl]-pyrrolidin-1-yl}-2-oxo-ethyl)-2-methylamino-propionamide | 531.29 |
| 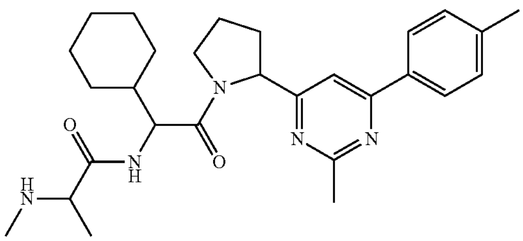 | 112 | N-{1-Cyclohexyl-2-[2-(2-methyl-6-p-tolyl-pyrimidin-4-yl)-pyrrolidin-1-yl]-2-oxo-ethyl}-2-methylamino-propionamide | 478.32 |
| 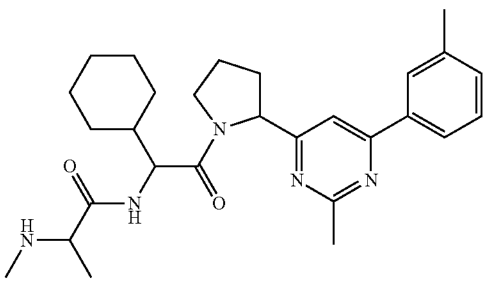 | 113 | N-{1-Cyclohexyl-2-[2-(2-methyl-6-m-tolyl-pyrimidin-4-yl)-pyrrolidin-1-yl]-2-oxo-ethyl}-2-methylamino-propionamide | 478.32 |
| 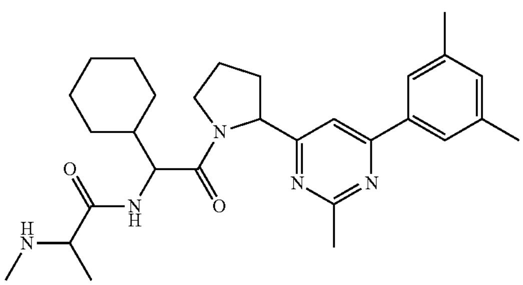 | 114 | N-(1-Cyclohexyl-2-{2-[6-(3,5-dimethyl-phenyl)-2-methyl-pyrimidin-4-yl]-pyrrolidin-1-yl}-2-oxo-ethyl)-2-methylamino-propionamide | 492.33 |
| 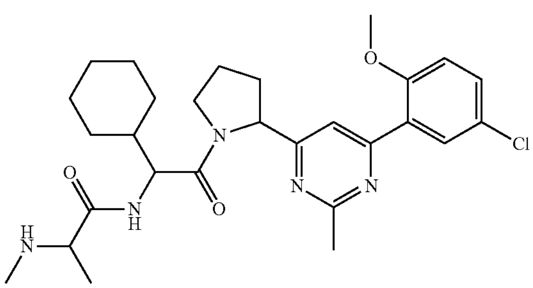 | 115 | N-(2-{2-[6-(5-Chloro-2-methoxy-phenyl)-2-methyl-pyrimidin-4-yl]-pyrrolidin-1-yl}-1-cyclohexyl-2-oxo-ethyl)-2-methylamino-propionamide | 528.27 |
| 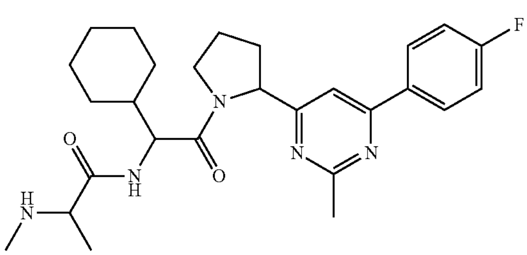 | 116 | N-(1-Cyclohexyl-2-{2-[6-(4-fluoro-phenyl)-2-methyl-pyrimidin-4-yl]-pyrrolidin-1-yl}-2-oxo-ethyl)-2-methylamino-propionamide | 482.29 |

TABLE 2-continued

| structure | Example name | | MS ESI (M + H)+ |
|---|---|---|---|
| 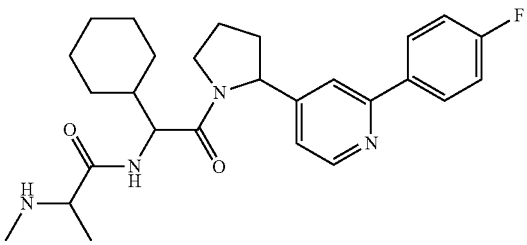 | 117 | N-(1-Cyclohexyl-2-{2-[2-(4-fluoro-phenyl)-pyridin-4-yl]-pyrrolidin-1-yl}-2-oxo-ethyl)-2-methylamino-propionamide | 467.28 |
| 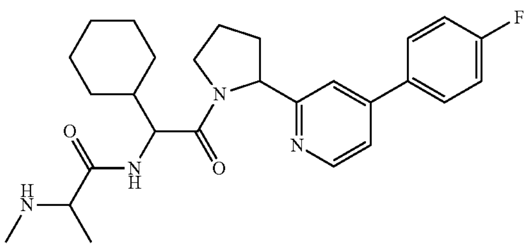 | 118 | N-(1-Cyclohexyl-2-{2-[4-(4-fluoro-phenyl)-pyridin-2-yl]-pyrrolidin-1-yl}-2-oxo-ethyl)-2-methylamino-propionamide | 467.28 |
| 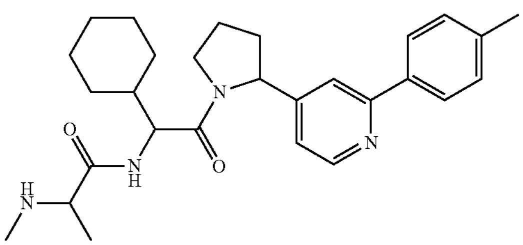 | 119 | N-{1-Cyclohexyl-2-oxo-2-[2-(2-p-tol-yl-pyridin-4-yl)-pyrrolidin-1-yl]-ethyl}-2-methylamino-propionamide | 463.31 |
| 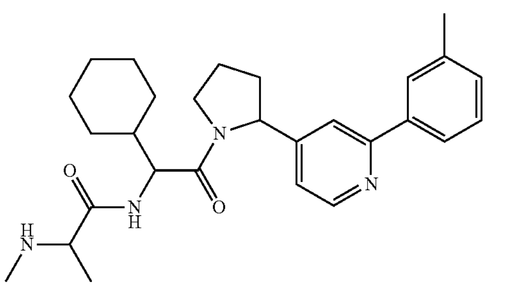 | 120 | N-{1-Cyclohexyl-2-oxo-2-[2-(2-m-tol-yl-pyridin-4-yl)-pyrrolidin-1-yl]-ethyl}-2-methylamino-propionamide | 463.31 |
| 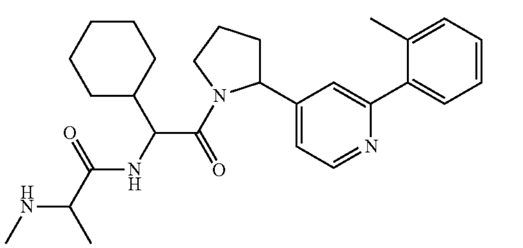 | 121 | N-{1-Cyclohexyl-2-oxo-2-[2-(2-o-tol-yl-pyridin-4-yl)-pyrrolidin-1-yl]-ethyl}-2-methylamino-propionamide | 463.31 |
| 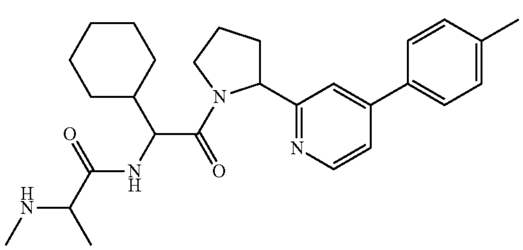 | 122 | N-{1-Cyclohexyl-2-oxo-2-[2-(4-p-tol-yl-pyridin-2-yl)-pyrrolidin-1-yl]-ethyl}-2-methylamino-propionamide | 463.31 |

TABLE 2-continued

| structure | Example name | | MS ESI (M + H)+ |
|---|---|---|---|
| 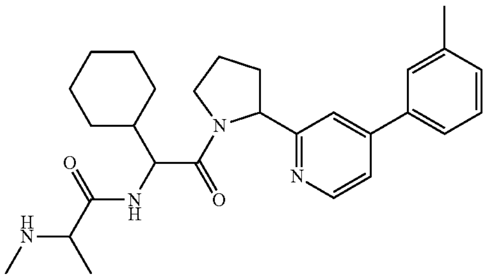 | 123 | N-{1-Cyclohexyl-2-oxo-2-[2-(4-m-tol-yl-pyridin-2-yl)-pyrrolidin-1-yl]-ethyl}-2-methylamino-propionamide | 463.31 |
| 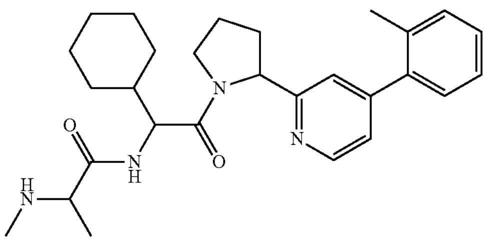 | 124 | N-{1-Cyclohexyl-2-oxo-2-[2-(4-o-tol-yl-pyridin-2-yl)-pyrrolidin-1-yl]-ethyl}-2-methylamino-propionamide | 463.31 |
| 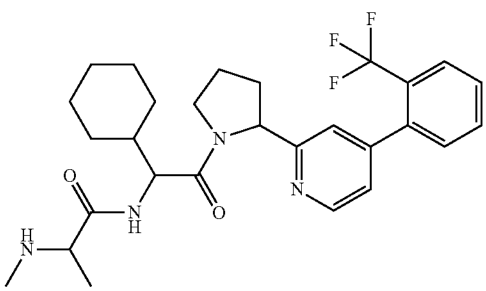 | 125 | N-(1-Cyclohexyl-2-oxo-2-{2-[4-(2-tri-fluoromethyl-phenyl)-pyridin-2-yl]-pyrrolidin-1-yl}-ethyl)-2-methyl-amino-propionamide | 517.28 |
| 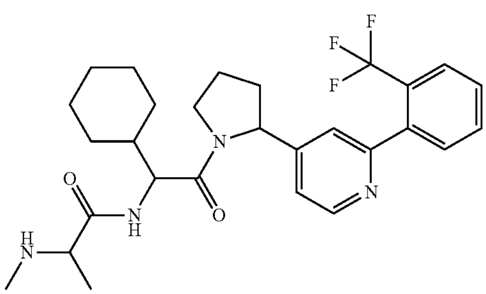 | 126 | N-(1-Cyclohexyl-2-oxo-2-{2-[2-(2-tri-fluoromethyl-phenyl)-pyridin-4-yl]-pyrrolidin-1-yl}-ethyl)-2-methyl-amino-propionamide | 517.28 |
| 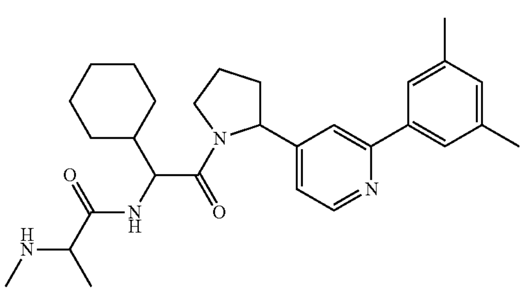 | 127 | N-(1-Cyclohexyl-2-{2-[2-(3,5-dimeth-yl-phenyl)-pyridin-4-yl]-pyrrolidin-1-yl}-2-oxo-ethyl)-2-methylamino-propionamide | 477.32 |

TABLE 2-continued

| structure | Example name | MS ESI (M + H)+ |
|---|---|---|
| | 128 N-(1-Cyclohexyl-2-{2-[4-(3,5-dimethyl-phenyl)-pyridin-2-yl]-pyrrolidin-1-yl}-2-oxo-ethyl)-2-methylamino-propionamide | 477.32 |
| | 129 N-(2-{2-[2-(5-Chloro-2-methoxy-phenyl)-pyridin-4-yl]-pyrrolidin-1-yl}-1-cyclohexyl-2-oxo-ethyl)-2-methyl-amino-propionamide | 513.26 |
| | 130 N-(2-{2-[4-(5-Chloro-2-methoxy-phenyl)-pyridin-2-yl]-pyrrolidin-1-yl}-1-cyclohexyl-2-oxo-ethyl)-2-methyl-amino-propionamide | 513.26 |
| | 131 N-{2-[2-(2-Benzo[1,3]dioxol-5-yl-pyridin-4-yl)-pyrrolidin-1-yl]-1-cyclo-hexyl-2-oxo-ethyl}-2-methylamino-propionamide | 493.28 |
| | 132 N-{2-[2-(4-Benzo[1,3]dioxol-5-yl-pyridin-2-yl)-pyrrolidin-1-yl]-1-cyclo-hexyl-2-oxo-ethyl}-2-methylamino-propionamide | 493.28 |

TABLE 2-continued

| structure | Example | name | MS ESI (M + H)+ |
|---|---|---|---|
| 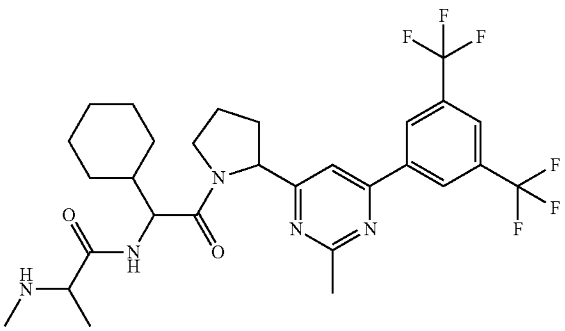 | 133 | N-(2-{2-[6-(3,5-Bis-trifluoromethyl-phenyl)-2-methyl-pyrimidin-4-yl]-pyrrolidin-1-yl}-1-cyclohexyl-2-oxo-ethyl)-2-methylamino-propionamide | 600.28 |
| 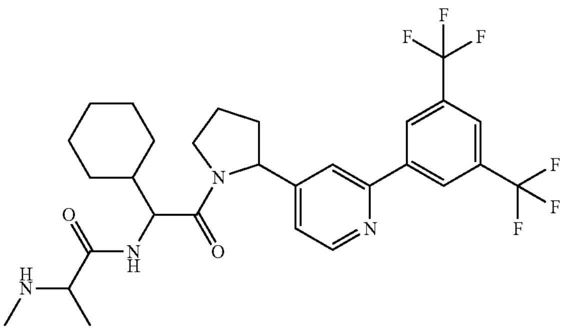 | 134 | N-(2-{2-[2-(3,5-Bis-trifluoromethyl-phenyl)-pyridin-4-yl]-pyrrolidin-1-yl}-1-cyclohexyl-2-oxo-ethyl)-2-methylamino-propionamide | 585.27 |
| 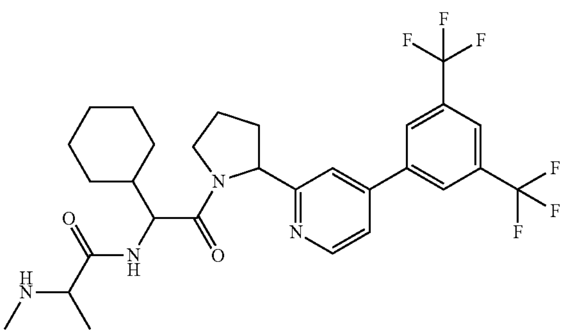 | 135 | N-(2-{2-[4-(3,5-Bis-trifluoromethyl-phenyl)-pyridin-2-yl]-pyrrolidin-1-yl}-1-cyclohexyl-2-oxo-ethyl)-2-methylamino-propionamide | 585.27 |

The preferred stereochemistry of the compound of Examples 1-103 are:

(S)—N-{(S)-1-Cyclohexyl-2-[(R)-2-(1H-indol-3-yl)-pyrrolidin-1-yl]-2-oxo-ethyl}-2-methylamino-propionamide;

(S)—N-{(S)-1-Cyclohexyl-2-[(S)-2-(1H-indol-3-yl)-pyrrolidin-1-yl]-2-oxo-ethyl}-2-methylamino-propionamide;

(S)—N-{(S)-1-Cyclohexyl-2-[(R)-2-(1H-indol-2-yl)-pyrrolidin-1-yl]-2-oxo-ethyl}-2-methylamino-propionamide;

(S)—N—((S)-1-Cyclohexyl-2-{(S)-2-[2-(2,3-dihydro-indol-1-yl)-pyridin-4-yl]-pyrrolidin-1-yl}-2-oxo-ethyl)-2-methylamino-propionamide;

(S)—N—((S)-1-Cyclohexyl-2-{(S)-2-[5-(2,3-dihydro-indol-1-yl)-pyridin-3-yl]-pyrrolidin-1-yl}-2-oxo-ethyl)-2-methylamino-propionamide;

(S)—N—((R)-1-Cyclohexyl-2-{(S)-2-[5-(2,3-dihydro-indol-1-yl)-pyridin-3-yl]-pyrrolidin-1-yl}-2-oxo-ethyl)-2-methylamino-propionamide;

(S)—N—((S)-1-Cyclohexyl-2-{(S)-2-[2-(3,4-dihydro-2H-quinolin-1-yl)-pyridin-4-yl]-pyrrolidin-1-yl}-2-oxo-ethyl)-2-methylamino-propionamide;

(S)—N—((S)-1-Cyclohexyl-2-{(S)-2-[2-(2,3-dihydro-pyrrolo[2,3-b]pyridin-1-yl)-pyridin-4-yl]-pyrrolidin-1-yl}-2-oxo-ethyl)-2-methylamino-propionamide;

(S)—N-{(S)-1-Cyclohexyl-2-[(S)-2-(5-indol-1-yl-pyridin-3-yl)-pyrrolidin-1-yl]-2-oxo-ethyl}-2-methylamino-propionamide;

(S)—N—((S)-1-Cyclohexyl-2-{(S)-2-[5-(3,4-dihydro-2H-quinolin-1-yl)-pyridin-3-yl]-pyrrolidin-1-yl}-2-oxo-ethyl)-2-methylamino-propionamide;

(S)—N—((S)-1-Cyclohexyl-2-oxo-2-{(S)-2-[2-(2-oxo-3,4-dihydro-2H-quinolin-1-yl)-pyridin-4-yl]-pyrrolidin-1-yl}-ethyl)-2-methylamino-propionamide;

(S)—N—((S)-1-Cyclohexyl-2-{(S)-2-[2-(6-fluoro-2,3-dihydro-indol-1-yl)-pyridin-4-yl]-pyrrolidin-1-yl}-2-oxo-ethyl)-2-methylamino-propionamide;

(S)—N—((S)-1-{(S)-2-[2-(6-Fluoro-2,3-dihydro-indol-1-yl)-pyridin-4-yl]-pyrrolidine-1-carbonyl}-2-methyl-propyl)-2-methylamino-propionamide;

(S)—N-{(S)-1-Cyclohexyl-2-[(S)-2-(2-isoquinolin-4-yl-pyridin-4-yl)-pyrrolidin-1-yl]-2-oxo-ethyl}-2-methylamino-propionamide;

(S)—N-{(S)-1-Cyclohexyl-2-[(R)-2-(2-isoquinolin-4-yl-pyridin-4-yl)-pyrrolidin-1-yl]-2-oxo-ethyl}-2-methylamino-propionamide;

(S)—N—((S)-1-Cyclohexyl-2-{(S)-2-[2-(5-fluoro-2,3-dihydro-indol-1-yl)-pyridin-4-yl]-pyrrolidin-1-yl}-2-oxo-ethyl)-2-methylamino-propionamide;

(S)—N-{(S)-1-Cyclohexyl-2-[(S)-2-(2-indazol-1-yl-pyridin-4-yl]-pyrrolidin-1-yl]-2-oxo-ethyl}-2-methylamino-propionamide;
(S)—N-{(S)-2-[(S)-2-(5-Benzofuran-3-yl-pyridin-3-yl)-pyrrolidin-1-yl]-1-cyclohexyl-2-oxo-ethyl}-2-methylamino-propionamide;
(S)—N-{(S)-2-[(S)-2-(2-Benzoimidazol-1-yl-pyridin-4-yl)-pyrrolidin-1-yl]-1-cyclohexyl-2-oxo-ethyl}-2-methylamino-propionamide;
(S)—N—((S)-1-Cyclohexyl-2-{(S)-2-[2-(3-methyl-indol-1-yl)-pyridin-4-yl]-pyrrolidin-1-yl}-2-oxo-ethyl)-2-methylamino-propionamide;
(S)-2-Methylamino-N—((S)-2-methyl-1-{(S)-2-[2-(3-methyl-indol-1-yl)-pyridin-4-yl]-pyrrolidine-1-carbonyl}-propyl)-propionamide;
(S)—N—((S)-1-Cyclohexyl-2-{(S)-2-[5-(1H-indol-3-yl)-pyridin-3-yl]-pyrrolidin-1-yl}-2-oxo-ethyl)-2-methylamino-propionamide;
(S)—N-{(S)-2-[(S)-2-(2-Benzotriazol-1-yl-pyridin-4-yl)-pyrrolidin-1-yl]-1-cyclohexyl-2-oxo-ethyl}-2-methylamino-propionamide;
(S)—N—((S)-1-Cyclohexyl-2-{(S)-2-[2-(5-fluoro-indol-1-yl)-pyridin-4-yl]-pyrrolidin-1-yl}-2-oxo-ethyl)-2-methylamino-propionamide;
(S)—N—((S)-1-Cyclohexyl-2-{(S)-2-[2-(6-fluoro-3,4-dihydro-2H-quinolin-1-yl)-pyridin-4-yl]-pyrrolidin-1-yl}-2-oxo-ethyl)-2-methylamino-propionamide;
(S)—N—((S)-1-Cyclohexyl-2-{(S)-2-[2-(1H-indol-2-yl)-pyridin-4-yl]-pyrrolidin-1-yl}-2-oxo-ethyl)-2-methylamino-propionamide;
(S)—N—((S)-1-Cyclohexyl-2-{(S)-2-[5-(5-fluoro-2,3-dihydro-indol-1-yl)-pyridin-3-yl]-pyrrolidin-1-yl}-2-oxo-ethyl)-2-methylamino-propionamide;
(S)—N—((S)-1-Cyclohexyl-2-{(S)-2-[2-(1H-indol-3-yl)-pyridin-4-yl]-pyrrolidin-1-yl}-2-oxo-ethyl)-2-methylamino-propionamide;
(S)—N—((S)-1-{(S)-2-[2-(6-Fluoro-indol-1-yl)-pyridin-4-yl]-pyrrolidine-1-carbonyl}-2-methyl-propyl)-2-methylamino-propionamide;
(S)—N—((S)-1-Cyclohexyl-2-{(R)-2-[2-(6-fluoro-indol-1-yl)-pyridin-4-yl]-pyrrolidin-1-yl}-2-oxo-ethyl)-2-methylamino-propionamide;
(S)—N—((S)-1-Cyclohexyl-2-{(S)-2-[2-(6-fluoro-indol-1-yl)-pyridin-4-yl]-pyrrolidin-1-yl}-2-oxo-ethyl)-2-methylamino-propionamide;
(S)—N—((S)-1-Cyclohexyl-2-oxo-2-{(S)-2-[5-(2-oxo-benzooxazol-3-yl)-pyridin-3-yl]-pyrrolidin-1-yl}-ethyl)-2-methylamino-propionamide;
(S)—N—((S)-1-Cyclohexyl-2-{(S)-2-[2-(1,3-dihydro-isoindol-2-yl)-pyridin-4-yl]-pyrrolidin-1-yl}-2-oxo-ethyl)-2-methylamino-propionamide;
(S)—N—((S)-1-Cyclohexyl-2-{(S)-2-[2-(3,4-dihydro-1H-isoquinolin-2-yl)-pyridin-4-yl]-pyrrolidin-1-yl}-2-oxo-ethyl)-2-methylamino-propionamide;
(S)—N-{(S)-2-[(S)-2-(5-Benzoimidazol-1-yl-pyridin-3-yl)-pyrrolidin-1-yl]-1-cyclohexyl-2-oxo-ethyl}-2-methylamino-propionamide;
(S)—N-{(S)-2-[(S)-2-(5-Benzotriazol-1-yl-pyridin-3-yl)-pyrrolidin-1-yl]-1-cyclohexyl-2-oxo-ethyl}-2-methylamino-propionamide;
(S)—N-{(S)-1-Cyclohexyl-2-[(S)-2-(5-indazol-1-yl-pyridin-3-yl)-pyrrolidin-1-yl]-2-oxo-ethyl}-2-methylamino-propionamide;
(S)—N—((S)-1-Cyclohexyl-2-{(S)-2-[2-(5-fluoro-3-methyl-indol-1-yl)-pyridin-4-yl]-pyrrolidin-1-yl}-2-oxo-ethyl)-2-methylamino-propionamide;
(S)—N—((S)-1-{(S)-2-[2-(5-Fluoro-3-methyl-indol-1-yl)-pyridin-4-yl]-pyrrolidine-1-carbonyl}-2-methyl-propyl)-2-methylamino-propionamide;
(S)—N—((S)-1-Cyclohexyl-2-{(S)-2-[5-(3,4-dihydro-2H-quinolin-1-yl)-pyridin-3-yl]-pyrrolidin-1-yl}-ethyl)-2-methylamino-propionamide;
(S)—N—((S)-1-Cyclohexyl-2-{(S)-2-[5-(3-methyl-indol-1-yl)-pyridin-3-yl]-pyrrolidin-1-yl}-2-oxo-ethyl)-2-methylamino-propionamide;
(S)—N—((S)-1-Cyclohexyl-2-{(S)-2-[5-(5-fluoro-3-methyl-indol-1-yl)-pyridin-3-yl]-pyrrolidin-1-yl}-2-oxo-ethyl)-2-methylamino-propionamide;
(S)—N—((S)-1-Cyclohexyl-2-{(S)-2-[5-(5-fluoro-indol-1-yl)-pyridin-3-yl]-pyrrolidin-1-yl}-2-oxo-ethyl)-2-methylamino-propionamide;
(S)—N-{(S)-1-Cyclohexyl-2-oxo-2-[(S)-2-(5-pyrrolo[2,3-b]pyridin-1-yl-pyridin-3-yl)-pyrrolidin-1-yl]-ethyl}-2-methylamino-propionamide;
(S)—N-{(S)-2-[(S)-2-(2-Benzoimidazol-1-yl-3-fluoro-pyridin-4-yl)-pyrrolidin-1-yl]-1-cyclohexyl-2-oxo-ethyl}-2-methylamino-propionamide;
(S)—N-{(S)-1-[(S)-2-(2-Benzoimidazol-1-yl-pyridin-4-yl)-pyrrolidine-1-carbonyl]-2-methyl-propyl}-2-methylamino-propionamide;
3-(5-{(S)-1-[(S)-2-Cyclohexyl-2-((S)-2-methylamino-propionylamino)-acetyl]-pyrrolidin-2-yl}-pyridin-3-yl)-indole-1-carboxylic acid dimethylamide;
(S)—N—((S)-1-Cyclohexyl-2-{(S)-2-[5-(1-ethyl-1H-indol-3-yl)-pyridin-3-yl]-pyrrolidin-1-yl}-2-oxo-ethyl)-2-methylamino-propionamide;
(S)—N-{(S)-1-Cyclohexyl-2-[(S)-2-(5-naphthalen-1-yl-pyridin-3-yl)-pyrrolidin-1-yl]-2-oxo-ethyl}-2-methylamino-propionamide;
(S)—N—((S)-1-Cyclohexyl-2-{(S)-2-[4-(6-fluoro-2,3-dihydro-indol-1-yl)-pyridin-2-yl]-pyrrolidin-1-yl}-2-oxo-ethyl)-2-methylamino-propionamide;
(S)—N—((S)-1-Cyclohexyl-2-{(S)-2-[4-(5-fluoro-2,3-dihydro-indol-1-yl)-pyridin-2-yl]-pyrrolidin-1-yl}-2-oxo-ethyl)-2-methylamino-propionamide;
(S)—N—((S)-2-{(S)-2-[5-(5-Chloro-2-methoxy-phenyl)-pyridin-3-yl]-pyrrolidin-1-yl}-1-cyclohexyl-2-oxo-ethyl)-2-methylamino-propionamide;
(S)—N-{(S)-1-Cyclohexyl-2-oxo-2-[(S)-2-(5-o-tolyl-pyridin-3-yl)-pyrrolidin-1-yl]-ethyl}-2-methylamino-propionamide;
(S)—N-{(S)-2-[(S)-2-(5-Benzo[1,3]dioxol-5-yl-pyridin-3-yl)-pyrrolidin-1-yl]-1-cyclohexyl-2-oxo-ethyl}-2-methylamino-propionamide;
(S)—N—((S)-1-Cyclohexyl-2-oxo-2-{(S)-2-[5-(3-trifluoromethyl-phenyl)-pyridin-3-yl]-pyrrolidin-1-yl}-ethyl)-2-methylamino-propionamide;
(S)—N—((S)-1-Cyclohexyl-2-{(S)-2-[5-(3-isopropyl-phenyl)-pyridin-3-yl]-pyrrolidin-1-yl}-2-oxo-ethyl)-2-methylamino-propionamide;
(S)—N-{(S)-1-Cyclohexyl-2-[(S)-2-(5-naphthalen-2-yl-pyridin-3-yl)-pyrrolidin-1-yl]-2-oxo-ethyl}-2-methylamino-propionamide;
(S)—N-{(S)-1-Cyclohexyl-2-oxo-2-[(S)-2-(7-phenyl-4,5,6,7-tetrahydro-benzothiazol-2-yl)-pyrrolidin-1-yl]-ethyl}-2-methylamino-propionamide;
(S)—N-{(S)-1-Cyclohexyl-2-oxo-2-[(S)-2-(1-phenyl-isoquinolin-7-yl)-pyrrolidin-1-yl]-ethyl}-2-methylamino-propionamide;
(S)—N-{(S)-1-Cyclohexyl-2-oxo-2-[(S)-2-(7-phenyl-6,7-dihydro-5H-[2]pyrindin-4-yl)-pyrrolidin-1-yl]-ethyl}-2-methylamino-propionamide;

(S)—N-{(S)-1-Cyclohexyl-2-oxo-2-[(S)-2-(5-phenyl-5,6,7,8-tetrahydro-quinolin-3-yl)-pyrrolidin-1-yl]-ethyl}-2-methylamino-propionamide;
(S)—N—((S)-1-Cyclohexyl-2-{(S)-2-[7-(4-fluoro-phenyl)-benzothiazol-2-yl]-pyrrolidin-1-yl}-2-oxo-ethyl)-2-methylamino-propionamide;
(S)—N—((S)-2-{(S)-2-[2-Chloro-5-(3-trifluoromethyl-phenyl)-pyridin-3-yl]-pyrrolidin-1-yl}-1-cyclohexyl-2-oxo-ethyl)-2-methylamino-propionamide;
(S)—N—((S)-2-{(S)-2-[5-(3,5-Bis-trifluoromethyl-phenyl)-pyridin-3-yl]-pyrrolidin-1-yl}-1-cyclohexyl-2-oxo-ethyl)-2-methylamino-propionamide;
(S)—N—((S)-1-Cyclohexyl-2-oxo-2-{(S)-2-[5-(2-trifluoromethyl-phenyl)-pyridin-3-yl]-pyrrolidin-1-yl}-ethyl)-2-methylamino-propionamide;
(S)—N—((S)-1-Cyclohexyl-2-{(S)-2-[5-(3,5-dimethyl-phenyl)-pyridin-3-yl]-pyrrolidin-1-yl}-2-oxo-ethyl)-2-methylamino-propionamide;
(S)—N—((S)-2-{(S)-2-[5-(4-tert-Butyl-phenyl)-pyridin-3-yl]-pyrrolidin-1-yl}-1-cyclohexyl-2-oxo-ethyl)-2-methylamino-propionamide;
(S)—N—((S)-1-Cyclohexyl-2-{(S)-2-[5-(4-fluoro-phenyl)-pyridin-3-yl]-pyrrolidin-1-yl}-2-oxo-ethyl)-2-methylamino-propionamide;
(S)—N-{(S)-1-Cyclohexyl-2-oxo-2-[(S)-2-(5-p-tolyl-pyridin-3-yl)-pyrrolidin-1-yl]-ethyl}-2-methylamino-propionamide;
(S)—N-{(S)-1-Cyclohexyl-2-oxo-2-[(S)-2-(5-m-tolyl-pyridin-3-yl)-pyrrolidin-1-yl]-ethyl}-2-methylamino-propionamide;
(S)—N—-[(S)-2-(S)-2-[2,3']-Bipyridinyl-5'-yl-pyrrolidin-1-yl)-1-cyclohexyl-2-oxo-ethyl]-2-methylamino-propionamide;
(S)—N—[(S)-2-((S)-2-[3,3']Bipyridinyl-5-yl-pyrrolidin-1-yl)-1-cyclohexyl-2-oxo-ethyl]-2-methylamino-propionamide;
(S)—N—[(S)-2-((S)-2-[3,4']Bipyridinyl-5-yl-pyrrolidin-1-yl)-1-cyclohexyl-2-oxo-ethyl]-2-methylamino-propionamide;
(S)—N—((S)-1-Cyclohexyl-2-{(S)-2-[6-(6-fluoro-2,3-dihydro-indol-1-yl)-2-methyl-pyrimidin-4-yl]-pyrrolidin-1-yl}-2-oxo-ethyl)-2-methylamino-propionamide;
(S)—N—((S)-1-Cyclohexyl-2-{(S)-2-[6-(5-fluoro-2,3-dihydro-indol-1-yl)-2-methyl-pyrimidin-4-yl]-pyrrolidin-1-yl}-2-oxo-ethyl)-2-methylamino-propionamide;
(S)—N-{(S)-1-Cyclohexyl-2-[(S)-2-(6-indol-1-yl-2-methyl-pyrimidin-4-yl)-pyrrolidin-1-yl]-2-oxo-ethyl}-2-methylamino-propionamide;
(S)—N-{(S)-1-Cyclohexyl-2-[(S)-2-(6-indol-1-yl-pyrimidin-4-yl)-pyrrolidin-1-yl]-2-oxo-ethyl}-2-methylamino-propionamide;
(S)—N-{(S)-1-Cyclohexyl-2-[(S)-2-(2-methyl-6-o-tolyl-pyrimidin-4-yl)-pyrrolidin-1-yl]-2-oxo-ethyl}-2-methylamino-propionamide;
(S)—N-{(S)-1-Cyclohexyl-2-oxo-2-[(S)-2-(6-o-tolyl-pyrimidin-4-yl)-pyrrolidin-1-yl]-ethyl}-2-methylamino-propionamide;
(S)—N—((S)-1-Cyclohexyl-2-{(S)-2-[2-methyl-6-(3-methyl-indol-1-yl)-pyrimidin-4-yl]-pyrrolidin-1-yl}-2-oxo-ethyl)-2-methylamino-propionamide;
(S)—N—((S)-1-Cyclohexyl-2-{(S)-2-[2-methyl-6-(3-trifluoromethyl-phenyl)-pyrimidin-4-yl]-pyrrolidin-1-yl}-2-oxo-ethyl)-2-methylamino-propionamide;
(S)—N-{(S)-2-[(S)-2-(6-Benzoimidazol-1-yl-2-methyl-pyrimidin-4-yl)-pyrrolidin-1-yl]-1-cyclohexyl-2-oxo-ethyl}-2-methylamino-propionamide;
(S)—N-{(S)-1-Cyclohexyl-2-[(S)-2-(2-methyl-6-naphthalen-1-yl-pyrimidin-4-yl)-pyrrolidin-1-yl]-2-oxo-ethyl}-2-methylamino-propionamide;
(S)—N-{(S)-2-[(S)-2-(6-Benzo[1,3]dioxol-5-yl-2-methyl-pyrimidin-4-yl)-pyrrolidin-1-yl]-1-cyclohexyl-2-oxo-ethyl}-2-methylamino-propionamide;
(S)—N—((S)-1-Cyclohexyl-2-{(S)-2-[6-(3-isopropyl-phenyl)-2-methyl-pyrimidin-4-yl]-pyrrolidin-1-yl}-2-oxo-ethyl)-2-methylamino-propionamide;
(S)—N—((S)-1-Cyclohexyl-2-{(S)-2-[6-(2,3-dihydro-indol-1-yl)-2-methyl-pyrimidin-4-yl]-pyrrolidin-1-yl}-2-oxo-ethyl)-2-methylamino-propionamide;
(S)—N-{(S)-1-Cyclohexyl-2-[(S)-2-(2-methyl-6-naphthalen-2-yl-pyrimidin-4-yl)-pyrrolidin-1-yl]-2-oxo-ethyl}-2-methylamino-propionamide;
(S)—N—((S)-1-Cyclohexyl-2-{(S)-2-[6-(5-fluoro-2,3-dihydro-indol-1-yl)-pyrimidin-4-yl]-pyrrolidin-1-yl}-2-oxo-ethyl)-2-methylamino-propionamide;
(S)—N—((S)-1-{(S)-2-[6-(5-Fluoro-2,3-dihydro-indol-1-yl)-2-methyl-pyrimidin-4-yl]-pyrrolidine-1-carbonyl}-2-methyl-propyl)-2-methylamino-propionamide;
(S)—N-{(S)-2-[(S)-2-(6-Benzofuran-3-yl-2-methyl-pyrimidin-4-yl)-pyrrolidin-1-yl]-1-cyclohexyl-2-oxo-ethyl}-2-methylamino-propionamide;
(S)—N—((S)-1-Cyclohexyl-2-{(S)-2-[6-(1H-indol-3-yl)-2-methyl-pyrimidin-4-yl]-pyrrolidin-1-yl}-2-oxo-ethyl)-2-methylamino-propionamide;
(S)—N—((S)-1-Cyclohexyl-2-{(S)-2-[6-(1H-indol-3-yl)-pyrimidin-4-yl]-pyrrolidin-1-yl}-2-oxo-ethyl)-2-methylamino-propionamide;
(S)—N—((S)-1-{(S)-2-[6-(1H-Indol-3-yl)-2-methyl-pyrimidin-4-yl]-pyrrolidine-1-carbonyl}-2-methyl-propyl)-2-methylamino-propionamide;
(S)—N—((S)-1-Cyclohexyl-2-{(S)-2-[6-(5-fluoro-3-methyl-indol-1-yl)-2-methyl-pyrimidin-4-yl]-pyrrolidin-1-yl}-2-oxo-ethyl)-2-methylamino-propionamide;
(S)—N—((S)-1-{(S)-2-[6-(5-Fluoro-3-methyl-indol-1-yl)-2-methyl-pyrimidin-4-yl]-pyrrolidine-1-carbonyl}-2-methyl-propyl)-2-methylamino-propionamide;
(S)—N—((S)-1-Cyclohexyl-2-{(S)-2-[6-(5-fluoro-3-methyl-indol-1-yl)-pyrimidin-4-yl]-pyrrolidin-1-yl}-2-oxo-ethyl)-2-methylamino-propionamide;
(S)—N—((S)-1-Cyclohexyl-2-{(S)-2-[6-(5-fluoro-indol-1-yl)-2-methyl-pyrimidin-4-yl]-pyrrolidin-1-yl}-2-oxo-ethyl)-2-methylamino-propionamide;
(S)—N—((S)-1-{(S)-2-[6-(5-Fluoro-indol-1-yl)-2-methyl-pyrimidin-4-yl]-pyrrolidine-1-carbonyl}-2-methyl-propyl)-2-methylamino-propionamide;
(S)—N—((S)-1-Cyclohexyl-2-{(S)-2-[6-(5-fluoro-indol-1-yl)-pyrimidin-4-yl]-pyrrolidin-1-yl}-2-oxo-ethyl)-2-methylamino-propionamide;
3-(6-{(S)-1-[(S)-2-Cyclohexyl-2-((S)-2-methylamino-propionylamino)-acetyl]-pyrrolidin-2-yl}-2-methyl-pyrimidin-4-yl)-indole-1-carboxylic acid dimethylamide;
3-(2-Methyl-6-{(S)-1-[(S)-3-methyl-2-((S)-2-methylamino-propionylamino)-butyryl]-pyrrolidin-2-yl}-pyrimidin-4-yl)-indole-1-carboxylic acid dimethylamide;
3-(6-{(S)-1-[(S)-2-Cyclohexyl-2-((S)-2-methylamino-propionylamino)-acetyl]-pyrrolidin-2-yl}-pyrimidin-4-yl)-indole-1-carboxylic acid dimethylamide;
(S)—N—((S)-1-{(S)-2-[6-(6-Fluoro-2,3-dihydro-indol-1-yl)-2-methyl-pyrimidin-4-yl]-pyrrolidine-1-carbonyl}-2-methyl-propyl)-2-methylamino-propionamide.

Preparation of Example 4
(S)—N—((S)-Cyclohexyl-2-{(S)-2-{2-[2,3-dihydro-indol-1-yl)-pyridin-4-yl]-pyrrolidin-1-yl}-pyrrolidin-1-yl)-2-oxo-ethyl)-2-methylamino-propionamide
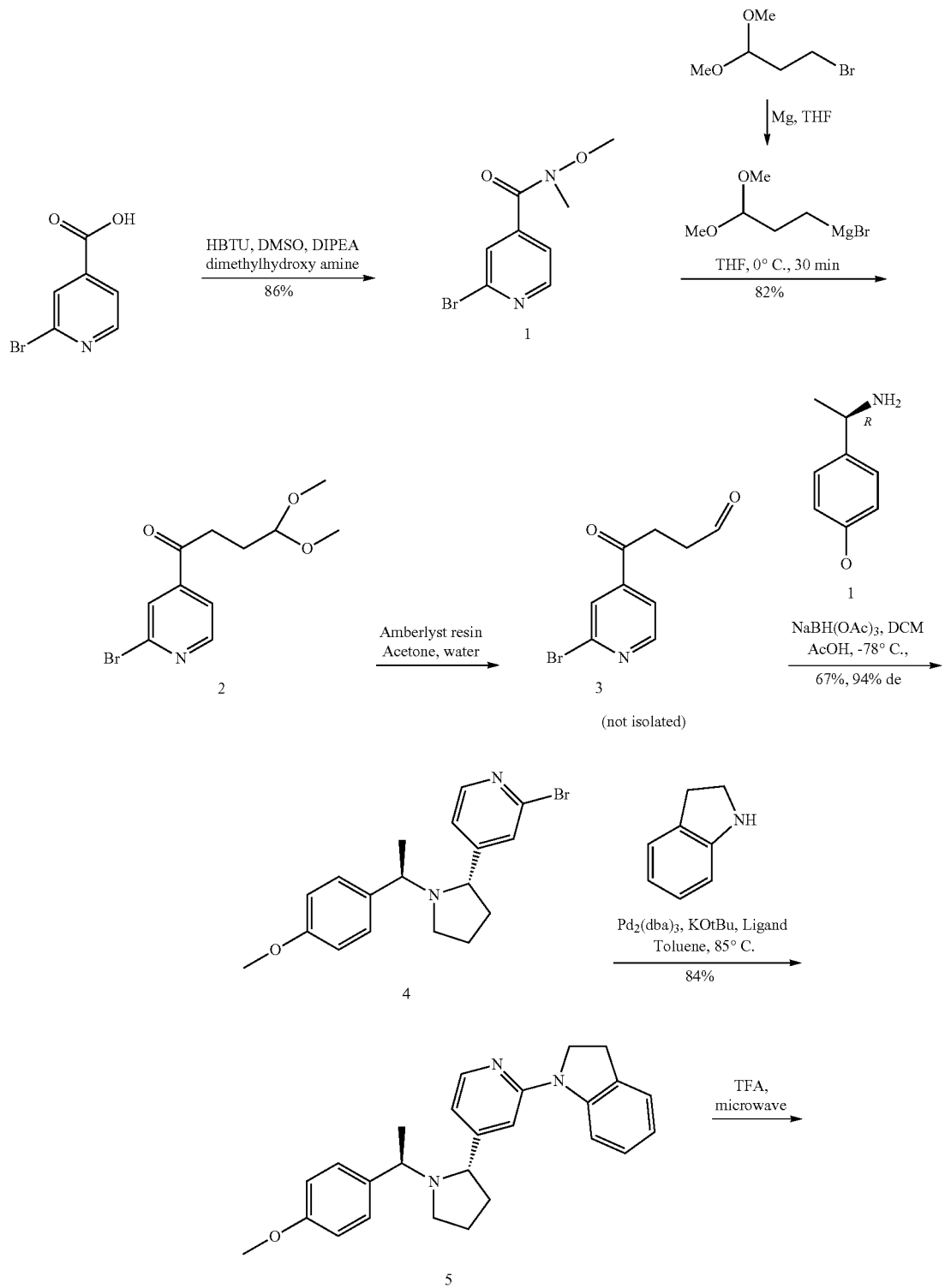

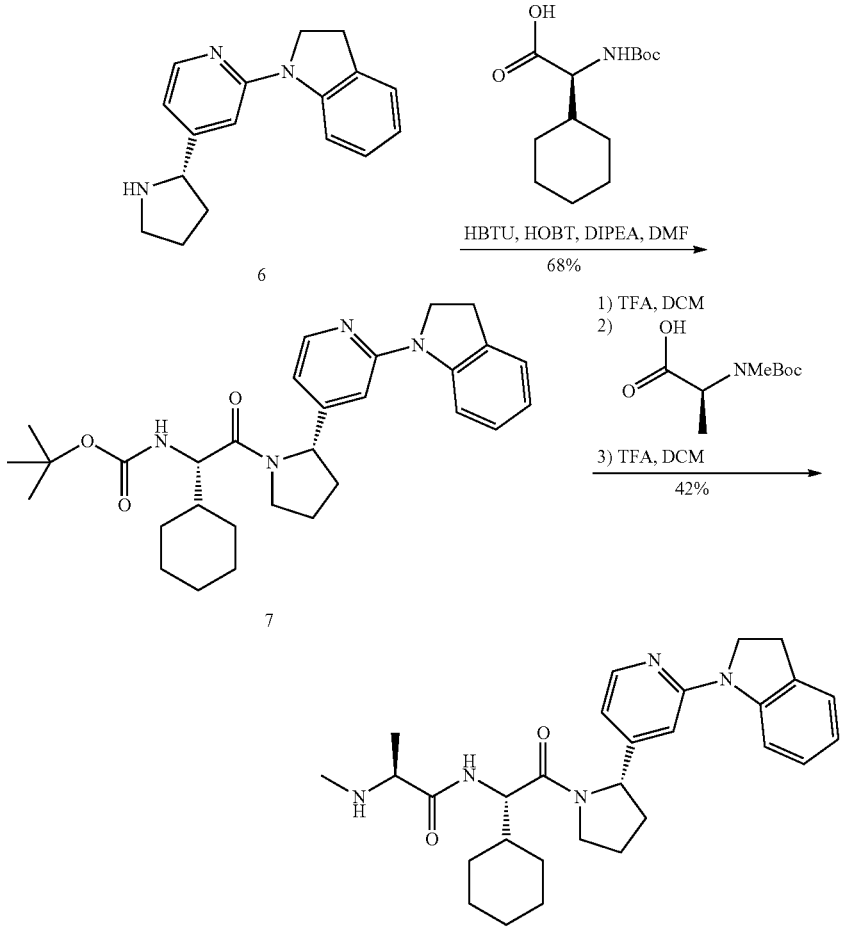

Example 4

2-Bromo-N-methoxy-N-methyl-isonicotinamide (1)

To a solution of 2-bromo-pyridine-4-carboxylic acid (11.83 g, 58.56 mmol) in DMSO (100 mL) are added HOBt (9.49 g, 70.30 mmol) and HBTU (26.70 g, 70.30 mmol). The mixture is stirred at room temperature for 20 min, then N,O-dimethylhydroxylamine HCl (6.28 g, 64.41 mmol) and diisopropylethylamine (22.72 g, 175.68 mmol) are added to the mixture. After stirring at room temperature for 3 h, the reaction mixture is diluted with water and extracted with EtOAc. The combined organic layers are washed with water, sat. NaHCO$_3$, brine, dried over Na$_2$SO$_4$, filtered and concentrated down. The crude product is purified by flash chromatography on silica gel (EtOAc/Hexane: 10%~40%) to give 2-Bromo-N-methoxy-N-methyl-isonicotinamide (12.4 g, 86%) as a white solid. M/Z=245.0

1-(2-Bromo-pyridin-4-yl)-4,4-dimethyoxy-butane-1-one (2)

To a suspension of Mg (3.67 g, 153.01 mmol) in THF (40 mL) is added cat. Iodine, followed by a solution of 3-bromo-1,1-dimethoxy-propane (21.47 g, 117.30 mmol) in THF (40 mL). The mixture is stirred at room temperature for 2 h. Then the fresh prepared Grignard reagent is cooled down in an ice bath, and added to a solution of 2-bromo-N-methoxy-N-methyl-isonicotinamide (12.50 g, 51.00 mmol) in THF (50 mL) at 0° C. The mixture is warmed up to room temperature and stirred at this temperature for 2 h. Then the reaction mixture is cooled in an ice bath, sat. NH$_4$Cl and water are added and the mixture is extracted with EtOAc. The combined organic layers are washed with brine, dried over Na$_2$SO$_4$, filtered and concentrated down. The crude product is purified by flash chromatography on silica gel (EtOAc/Hexane: 10%) to give 1-(2-Bromo-pyridin-4-yl)-4,4-dimethyoxy-butane-1-one (12.1 g, 82%) as a pale yellow oil. M/Z=288.14

2-Bromo-4-{(S)-1-[(R)-1-(4-methoxy-phenyl)-ethyl]-pyrrolidin-2-yl}-pyridine (4)

To a solution of 1-(2-Bromo-pyridin-4-yl)-4,4-dimethyoxy-butane-1-one (1.34 g, 4.65 mmol) in acetone (15 mL) is added Amberlyst resin 15 (1 g) and water (0.5 mL). After mechanical shaking for 3 h at room temperature, the mixture is filtered. The resin beads are washed with acetone and dichloromethane. The filtrate is concentrated down to give 4-(2-bromo-pyridin-4-yl)-4-oxo-butylaldehyde (3), which is used in next step without further purification.

A solution of 4-(2-bromo-pyridin-4-yl)-4-oxo-butylaldehyde in dichloromethane (50 mL) is cooled to −78° C., then sodium triethoxyborohydride (2.96 g, 13.95 mmol) and acetic acid (0.5 mL) are added. After the mixture was stirred at this temperature for 30 min, R(+)-α-methylbenzylamine (0.67 g, 4.42 mmol) is added and the mixture was warmed up to room temperature overnight. Sat. NaHCO₃ is added to the mixture and the layers are separated. The aqueous layer is extracted with dichloromethane and the combined organic layers are washed with brine, dried over Na₂SO₄, filtered and concentrated down. The crude product is purified by flash chromatography on silica gel (EtOAc/Hexane: 5%~20%) to give 2-Bromo-4-{(S)-1-[(R)-1-(4-methoxy-phenyl)-ethyl]-pyrrolidin-2-yl}-pyridine as a white solid (1.12 g, 67%). M/Z=361.28

1-(4-{(S)-1-[(R)-1-(4-Methoxy-phenyl)-ethyl]pyrrolidin-2-yl}-pyridin-2-yl)-2,3-dihydro-1H-indole (5)

To a solution of 2-Bromo-4-{(S)-1-[(R)-1-(4-methoxy-phenyl)-ethyl]-pyrrolidin-2-yl}-pyridine (0.15 g, 0.41 mmol) in toluene (30 mL) are added indoline (0.10 g, 0.83 mmol), 2-(dicyclohexylphosphino)-biphenyl (14 mg, 0.04 mmol), Pd₂(dba)₃ (19 mg, 0.02 mmol) and potassium tert-butoxide (0.11 g, 1.04 mmol). The reaction mixture is stirred at 85° C. for 3 h and cooled to room temperature. Water and EtOAc are added to the mixture. The layers are separated and the aqueous layer is extracted with EtOAc. The combined organic layers are washed with brine, dried over Na₂SO₄, filtered and concentrated down. The crude product is purified by flash chromatography on silica gel (EtOAc/Hexane: 5%~25%) to give (1-(4-{(S)-1-[(R)-1-(4-Methoxy-phenyl)-ethyl]-pyrrolidin-2-yl}-pyridin-2-yl)-2,3-dihydro-1H-indole (140 mg, 84%) as an oil. M/Z=400.2 [M+1]

((S)-1-Cyclohexyl-2-{(S)-2-[2-(2,3-dihydro-indol-1-yl)-pyridin-4-yl]-pyrrolidin-1-yl}-2-oxo-ethyl)-carbamic Acid Tert-butyl Ester (7)

A solution of (1-(4-{(S)-1-[(R)-1-(4-Methoxy-phenyl)-ethyl]-pyrrolidin-2-yl}-pyridin-2-yl)-2,3-dihydro-1H-indole (140 mg, 0.35 mmol) in TFA (10 mL) is heated in microwave at 100° C. for 30 min and concentrated down to give crude 1-((S)-4-pyrrolidin-2-yl-pyridin-2-yl)-2,3-dihydro-1H-indole (6), which is used in next step without further purification.

A solution of (S)-tert-butoxycarbonylamino-cyclohexyl-acetic acid (99 mg, 0.39 mmol), HOBt (57 mg, 0.42 mmol) and HBTU (160 mg, 0.42 mmol) in DMF (10 mL) is stirred at room temperature for 30 min. Then a solution of 1-((S)-4-pyrrolidin-2-yl-pyridin-2-yl)-2,3-dihydro-1H-indole (6) in DMF (10 mL) is added, followed by diisopropylamine (226 mg, 1.75 mmol). After stirring at room temperature for 2 h, the reaction mixture is diluted with water and extracted with EtOAc. The combined organic layers are washed with water, sat. NaHCO₃, brine, dried over Na₂SO₄, filtered and concentrated down. The crude product is purified by flash chromatography on silica gel (EtOAc/Hexane: 5%~40%) to give ((S)-1-Cyclohexyl-2-{(S)-2-[2-(2,3-dihydro-indol-1-yl)-pyridin-4-yl]-pyrrolidin-1-yl}-2-oxo-ethyl)-carbamic acid tert-butyl ester as white solid (120 mg, 68%). M/Z=505.3 [M+1]

(S)—N—((S)-1-Cyclohexyl-2-{(S)-2-[2-(2,3-dihydro-indol-1-yl)-pyridin-4-yl]-pyrrolidin-1-yl}-2-oxo-ethyl)-2-methylamino-propionamide (Example 4)

A solution of ((S)-1-Cyclohexyl-2-{(S)-2-[2-(2,3-dihydro-indol-1-yl)-pyridin-4-yl]-pyrrolidin-1-yl}-2-oxo-ethyl)-carbamic acid tert-butyl ester (120 mg, 0.24 mmol) in DCM (5 mL) is added TFA (6 mL). After stirring at room temperature for 1 h, the reaction mixture is concentrated down to give crude (S)-2-Amino-2-cyclohexyl-1-{(S)-2-[2-(2,3-dihydro-indol-1-yl)-pyridin-4-yl]-pyrrolidin-1-yl}-ethanone, which is used in next step without further purification.

A solution of Boc-N-methyl-L-α-alanine (53 mg, 0.26 mmol), HOBt (39 mg, 0.29 mmol) and HBTU (108 mg, 0.29 mmol) in DMF (10 mL) is stirred at room temperature for 30 min. Then a solution of (S)-2-Amino-2-cyclohexyl-1-{(S)-2-[2-(2,3-dihydro-indol-1-yl)-pyridin-4-yl]-pyrrolidin-1-yl}-ethanone in DMF (10 mL) is added, followed by diisopropylethylamine (153 mg, 1.19 mmol). The mixture is stirs at room temperature for 2 h, then diluted with water and extracted with EtOAc. The combined organic layers are washed with water, sat. NaHCO₃, brine, dried over Na₂SO₄, filtered and concentrated down. The crude product is dissolved in dichloromethane (5 mL). TFA (5 mL) is added. The resulting mixture is stirred at room temperature for 1 h and concentrated down to give a crude product, which is purified by prep. reverse phase HPLC (Column: Waters Sunfire Prep C18 OBD 5 µM 30×100 mm; Gradient: AcCN/water with 0.1% TFA: 10%~70%) to give (S)—N—((S)-1-Cyclohexyl-2-{(S)-2-[2-(2,3-dihydro-indol-1-yl)-pyridin-4-yl]-pyrrolidin-1-yl}-2-oxo-ethyl)-2-methylamino-propionamide (72 mg, 42%) as a TFA salt. M/Z=490.2 [M+1].

Preparation of Example 19

(S)—N-{(S)-2-[(S)-2-(2-Benzoimidazol-1-yl-pyridin-4-yl)-pyrrolidin-1-yl]-2-oxo-ethyl}-2-methylamino-propionamide

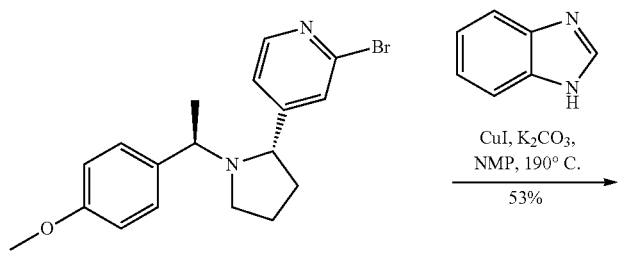

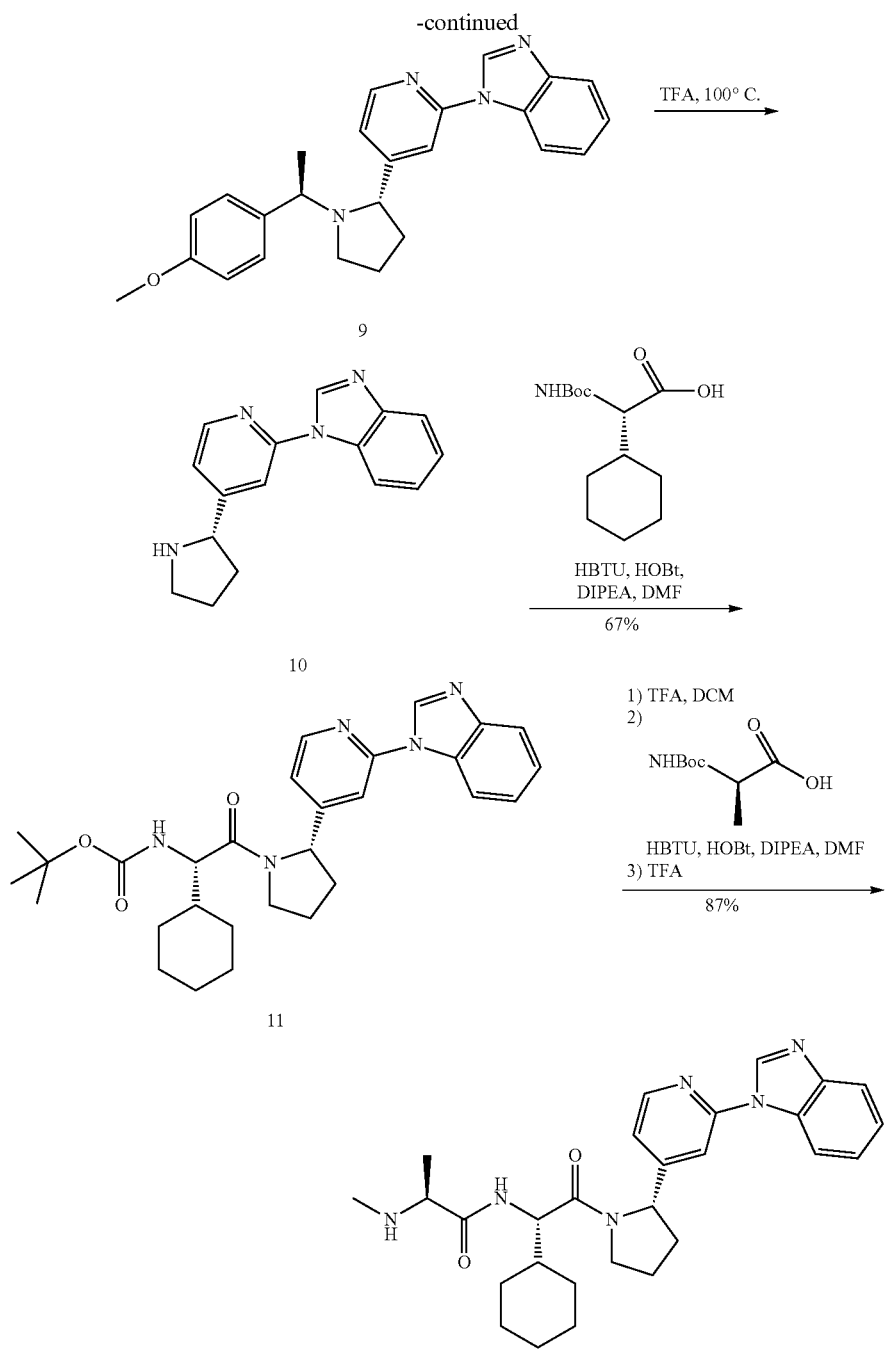

Example 19

2-(4-{(S)-1-[(R)-1-(4-methoxy-phenyl)-ethyl]-pyrrolidin-2-yl}-Pyridin-2-yl)-1H-benzomidazole (9)

To a solution of 2-Bromo-4-{(S)-1-[(R)-1-(4-methoxy-phenyl)-ethyl]-pyrrolidin-2-yl}-Pyridine (0.15 g, 0.41 mmol) in NMP (1 mL) are added benzomidazole (98 mg, 0.83 mmol), copper(I) iodide (8 mg, 0.04 mmol) and potassium carbonate (143 mg, 1.04 mmol). The mixture is heated in microwave at 190° C. for 30 min and cooled down. Water and EtOAc are added. The layers are separated and the organic layer is washed with water, brine, dried over $Na_2SO_4$, filtered and concentrated down. The crude product is purified by flash chromatography on silica gel (EtOAc/Hexane: 5%~15%) to give 2-(4-{(S)-1-[(R)-1-(4-methoxy-phenyl)-ethyl]-pyrrolidin-2-yl}-pyridin-2-yl)-1H-benzomidazole as a yellow solid (88 mg, 53%). M/Z=399.2 [M+1]

{(S)-2-[(S)-2-(2-benzoimidazol-1-yl-pyridin-4-yl)-pyrrolidin-1-yl]-1-cyclohexyl-2-oxo-ethyl}-carbamic Acid Tert-butyl Ester (11)

A solution of 2-(4-{(S)-1-[(R)-1-(4-methoxy-phenyl)-ethyl]-pyrrolidin-2-yl}-pyridin-2-yl)-1H-benzomidazole (88 mg, 0.21 mmol) in TFA (5 mL) is heated in microwave at 100°

C. for 30 min and concentrated down to give crude 1-((S)-4-pyrrolidin-2-yl-pyridine-2-yl)-1H-benzoimidazole (10), which is used in next step without further purification.

A solution of (S)-tert-butoxycarbonylamino-cyclohexyl-acetic acid (51 mg, 0.21 mmol), HOBt (31 mg, 0.23 mmol) and HBTU (88 mg, 0.23 mmol) in DMF (5 mL) is stirred at room temperature for 30 min. Then a solution of —((S)-4-pyrrolidin-2-yl-pyridine-2-yl)-1H-benzoimidazole (10) in DMF (5 mL) is added, followed by diisopropylethylamine (135 mg, 1.05 mmol). After stirring at room temperature for 2 h, the reaction mixture is diluted with water and extracted with EtOAc. The combined organic layers are washed with water, sat. NaHCO$_3$, brine, dried over Na$_2$SO$_4$, filtered and concentrated down. The crude product is purified by flash chromatography on silica gel (EtOAc/Hexane: 5%~40%) to give {(S)-2-[(S)-2-(2-benzoimidazol-1-yl-pyridin-4-yl)-pyrrolidin-1-yl]-1-cyclohexyl-2-oxo-ethyl}-carbamic acid tert-butyl ester (71 mg, 67%) as a white solid. M/Z=504.2 [M+1]

(S)—N-{(S)-2-[(S)-2-(2-Benzoimidazol-1-yl-pyridin-4-yl)-pyrrolidin-1-yl]-2-oxo-ethyl}-2-methylamino-propionamide (Example 18)

A solution of {(S)-2-[(S)-2-(2-benzoimidazol-1-yl-pyridin-4-yl)-pyrrolidin-1-yl]-1-cyclohexyl-2-oxo-ethyl}-carbamic acid tert-butyl ester (70 mg, 0.14 mmol) in DCM (2 mL) is added TFA (2 mL). After stirring at room temperature for 1 h, the reaction mixture is concentrated down to give crude (S)-2-Amino-1-[(S)-2-(2-benzoimidazol-1-yl-pyridin-4-yl)-pyrrolidin-1-yl]-2-cyclohexyl-ethanone, which is used in next step without further purification.

A solution of Boc-N-methyl-L-α-alanine (27 mg, 0.14 mmol), HOBt (21 mg, 0.15 mmol) and HBTU (58 mg, 0.15 mmol) in DMF (5 mL) is stirred at room temperature for 30 min. Then a solution of (S)-2-Amino-1-[(S)-2-(2-benzoimidazol-1-yl-pyridin-4-yl)-pyrrolidin-1-yl]-2-cyclohexyl-ethanone in DMF (5 mL) is added, followed by diisopropylethylamine (90 mg, 0.69 mmol). After stirring at room temperature for 2 h, the reaction mixture is diluted with water and extracted with EtOAc. The combined organic layers are washed with water, sat. NaHCO$_3$, brine, dried over Na$_2$SO$_4$, filtered and concentrated down. The crude product is dissolved in dichloromethane (2 mL) and TFA (2 mL) is added. The resulting mixture is stirred at room temperature for 1 h and concentrated down to give a crude product, which is purified by prep. reverse phase HPLC (Column: Waters Sunfire Prep C18 OBD 5 uM 30×100 mm; Gradient: AcCN/water with 0.1% TFA: 10%~70%) to give (S)—N-{(S)-2-[(S)-2-(2-Benzoimidazol-1-yl-pyridin-4-yl)-pyrrolidin-1-yl]-2-oxo-ethyl}-2-methylamino-propionamide (87 mg, 87%) as a TFA salt. Mass M/Z=489.36 [M+1]).

Preparation of Example 28

(S)—N—((S)-1-Cyclohexyl-2-{(S)-2-[2-[2-(1H-indol-3-yl)-pyridin-4-yl]-pyrrolidin-1-yl}-2-oxo-ethyl)-2-methylamino-propionamide

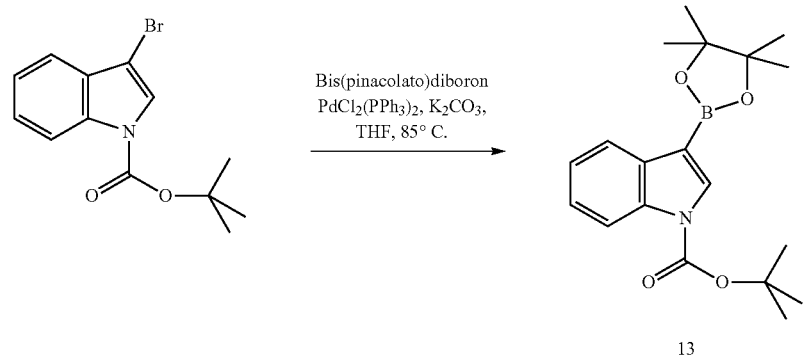

13

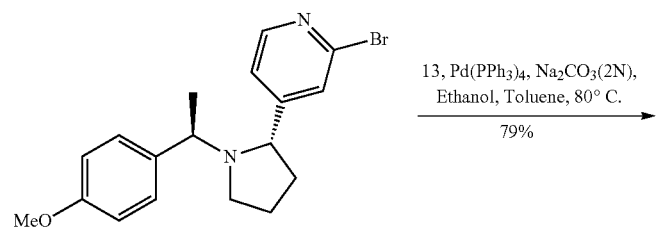

4

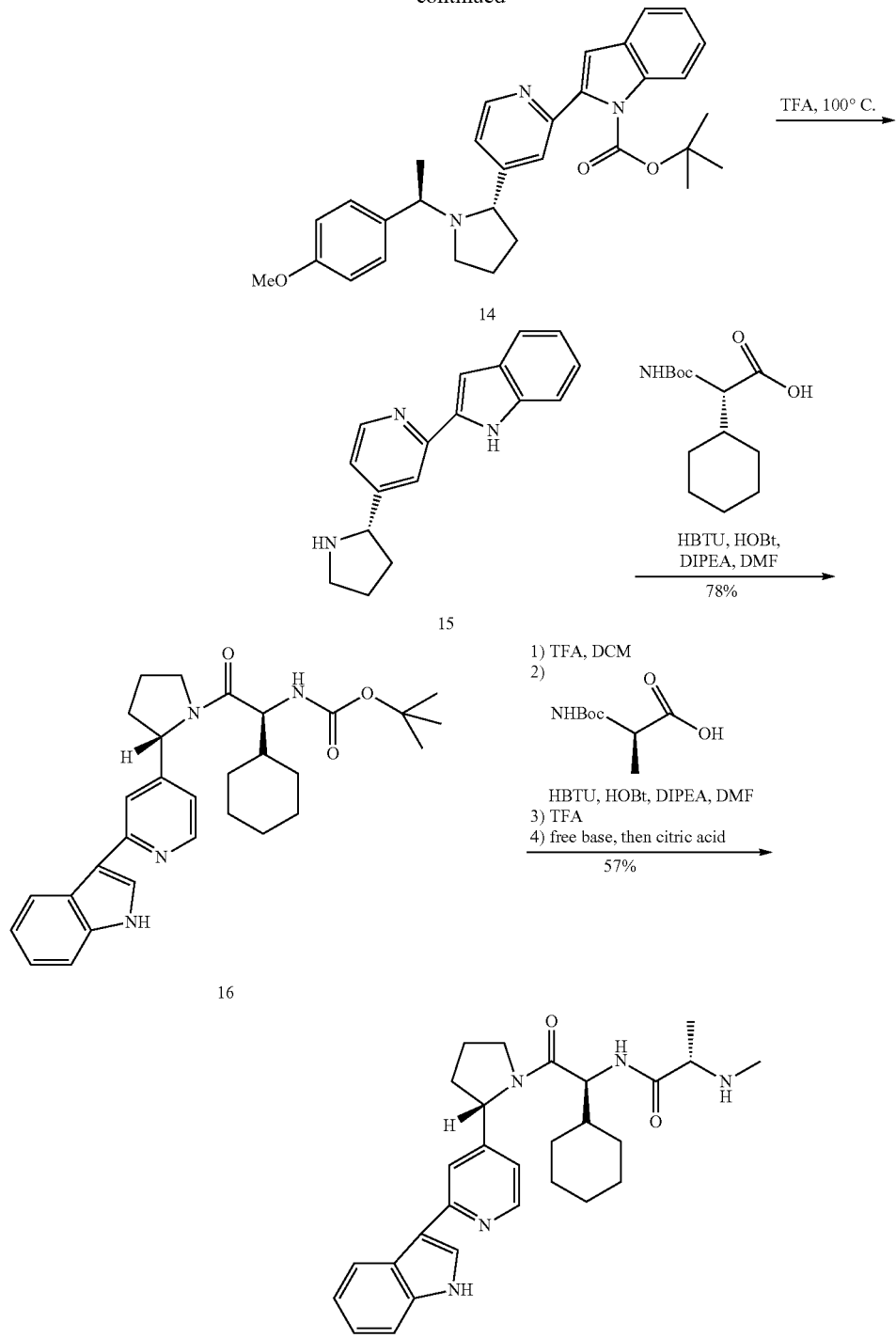

Example 28

3-(4-{(S)-1-[(R)-1-(4-Methoxy-phenyl)-ethyl]-pyrrolidin-2-yl}-pyridin-2-yl)-indole-1-carboxylic Acid Tert-butyl Ester (14)

To a solution of 3-bromoindole-1-carboxylic acid tert-butyl ester (200 mg, 0.67 mmol) in THF (10 mL) are added bis(pinacolato)diboron (257 mg, 1.01 mmol), PdCl$_2$(PPh$_3$)$_2$ (23 mg, 0.03 mmol) and potassium carbonate (0.23 g, 2.36 mmol). The reaction mixture is stirred at 85° C. overnight, cooled to room temperature, filtered through a celite pad and concentrated down to give crude 3-(4,4,5,5-tetramethyl-[1,3,2]dioxaborolan-2-yl)-indole-1-carboxylic acid tert-butyl ester (13), which is used in next step without further purification.

To a solution of 2-Bromo-4-{(S)-1-[(R)-1-(4-methoxy-phenyl)-ethyl]-pyrrolidin-2-yl}-pyridine (160 mg, 0.44 mmol) in a mixture of toluene (9 mL) and ethanol (3 mL) are added 3-(4,4,5,5-tetramethyl-[1,3,2]dioxaborolan-2-yl)-indole-1-carboxylic acid tert-butyl ester (228 mg, 0.66 mmol), Pd(PPh₃)₄ (51 mg, 0.04 mmol) and sodium carbonate (2N) (0.7 mL, 1.40 mmol). The reaction mixture is stirred at 85° C. overnight, cooled to room temperature. Water and EtOAc are added to the mixture. The layers are separated and the aqueous layer is extracted with EtOAc. The combined organic layers are washed with brine, dried over Na₂SO₄, filtered and concentrated down. The crude product is purified by flash chromatography on silica gel (EtOAc/Hexane: 10%~90%) to give 3-(4-{(S)-1-[(R)-1-(4-Methoxy-phenyl)-ethyl]-pyrrolidin-2-yl}-pyridin-2-yl)-indole-1-carboxylic acid tert-butyl ester as a yellow solid (175 mg, 79%). M/Z=498.32 [M+1]

((S)-1-Cyclohexyl-2-{(S)-2-[2-(1H-indol-3-yl)-pyridin-4-yl]-pyrrolidin-1-yl}-2-oxo-ethyl-carbamic Acid Tert-butyl Ester (16)

A solution of 3-(4-{(S)-1-[(R)-1-(4-Methoxy-phenyl)-ethyl]-pyrrolidin-2-yl}-pyridin-2-yl)-indole-1-carboxylic acid tert-butyl ester (160 mg, 0.31 mmol) in TFA (5 mL) is heated in microwave at 100° C. for 30 min and concentrated down to give crude 3-((S)-4-pyrrolidin-2-yl-pyridine-2-yl)-1H-indole (15), which is used in next step without further purification.

A solution of (S)-tert-butoxycarbonylamino-cyclohexyl-acetic acid (75 mg, 0.29 mmol), HOBt (46 mg, 0.33 mmol) and HBTU (127 mg, 0.33 mmol) in DMF (5 mL) is stirred at room temperature for 30 min. Then a solution of 3-((S)-4-pyrrolidin-2-yl-pyridine-2-yl)-1H-indole (15) in DMF (5 mL) is added, followed by diisopropylethylamine (198 mg, 1.50 mmol). After stirring at room temperature for 2 h, the reaction mixture is diluted with water and extracted with EtOAc. The combined organic layers are washed with water, sat. NaHCO₃, brine, dried over Na₂SO₄, filtered and concentrated down. The crude product is purified by flash chromatography on silica gel (EtOAc/Hexane: 5%~40%) to give ((S)-1-Cyclohexyl-2-{(S)-2-[2-(1H-indol-3-yl)-pyridin-4-yl]-pyrrolidin-1-yl}-2-oxo-ethyl)-carbamic acid tert-butyl ester as a yellow solid (120 mg, 78%). Mass M/Z=503.34 [M+1]

(S)—N—((S)-1-Cyclohexyl-2-{(S)-2-[2-(1H-indol-3-yl)-pyridin-4-yl]-pyrrolidin-1-yl}-2-oxo-ethyl)-2-methylamino-propionamide (Example 28)

A solution of ((S)-1-Cyclohexyl-2-{(S)-2-[2-(1H-indol-3-yl)-pyridin-4-yl]-pyrrolidin-1-yl}-2-oxo-ethyl)-carbamic acid tert-butyl ester (120 mg, 0.24 mmol) in DCM (2 mL) is added TFA (2 mL). After stirring at room temperature for 1 h, the reaction mixture is concentrated down to give crude (S)-2-Amino-2-cyclohexyl-1-{(S)-2-[2-(1H-indole-3-yl)-pyridin-4-yl]-pyrrolidin-1-yl}-ethanone, which is used in next step without purification.

A solution of Boc-N-methyl-L-α-alanine (46 mg, 0.22 mmol), HOBt (35 mg, 0.26 mmol) and HBTU (100 mg, 0.26 mmol) in DMF mL) is stirred at room temperature for 30 min. Then a solution of (S)-2-Amino-2-cyclohexyl-1-{(S)-2-[2-(1H-indole-3-yl)-pyridin-4-yl]-pyrrolidin-1-yl}-ethanone in DMF (5 mL) is added, followed by diisopropylethylamine (154 mg, 1.19 mmol). After stirring at room temperature for 2 h, the reaction mixture is diluted with water and extracted with EtOAc. The combined organic layers are washed with water, sat. NaHCO₃, brine, dried over Na₂SO₄, filtered and concentrated down. The crude product is dissolved in dichloromethane (2 mL) and TFA (2 mL) is added. The resulting mixture is stirred at room temperature for 1 h and concentrated down to give a crude product, which is purified by prep. reverse phase HPLC (Column: Waters Sunfire Prep C18 OBD 5 uM 30)(100 mm; Gradient: AcCN/water with 0.1% TFA: 10%~70%)) to give (S)—N—((S)-1-Cyclohexyl-2-{(S)-2-[2-[2-(1H-indol-3-yl)-pyridin-4-yl]-pyrrolidin-1-yl}-2-oxo-ethyl)-2-methylamino-propionamide (91 mg, 56%) as a TFA salt. Mass M/Z=488.33 [M+1].

Preparation of Example 24

(S)—N—((S)-1-Cyclohexyl-2-{(S)-2-[2-(5-fluoro-indol-1-yl)-pyridin-4-yl]-pyrrolidin-1-yl}-2-oxo-ethyl)-2-methylamino-propionamide

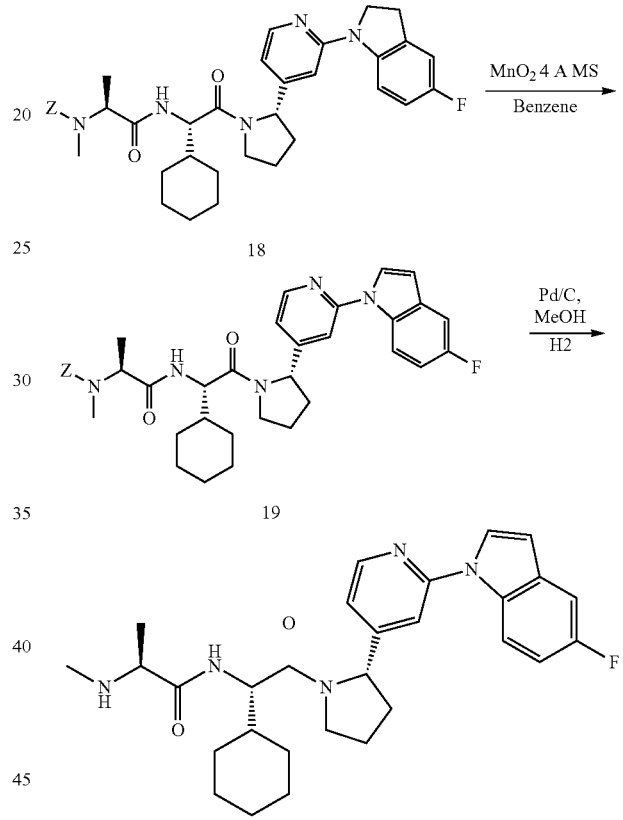

Example 24

[(S)-1-((S)-1-Cyclohexyl-2-{(S)-2-[2-(5-fluoro-indol-1-yl)-pyridin-4-yl]-pyrrolidin-1-yl}-2-oxo-ethylcarbamoyl)-ethyl]-methyl-carbamic acid benzyl ester (19)

A solution of [(S)-1-(S)-1-Cyclohexyl-2-{(S)-2-[2-(5-fluoro-2,3-dihydro-indol-1-yl)-pridin-4-yl]-pyrrolidin-1-yl}-2-oxo-ethylcarbamoyl)-ethyl]-methyl-carbamic acid benzyl ester (18) (50 mg, 0.08 mmol, prepared with a similar procedure of 7) in benzene (2 mL) is added the activated MnO₂ (72 mg, 820 mmol) and grounded 4 Å molecular sieves (0.1 g). After stirring at 45° C. for 1 h, the reaction mixture is concentrated down to give crude [(S)-1-(S)-1-Cyclohexyl-2-{(S)-2-[2-(5-fluoro-indol-1-yl)-pyridin-4-yl]-pyrrolidin-1-yl}-2-oxo-ethylcarbamoyl)-ethyl]-methyl-carbamic acid benzyl ester (19) (39 mg, 78%), which is used in next step without further purification. M/Z=640.1 [M+1].

(S)—N—((S)-1-Cyclohexyl-2-{(S)-2-[2-(5-fluoro-indol-1-yl)-pyridin-4-yl]-pyrrolidin-1-yl}-2-oxo-ethyl)-2-methylamino-propionamide (Example 24)

A solution of [(S)-1-((S)-1-Cyclohexyl-2-{(S)-2-[2-(5-fluoro-indol-1-yl)-pyridin-4-yl]-pyrrolidin-1-yl}-2-oxo-ethylcarbamoyl)-ethyl]-methyl-carbamic acid benzyl ester (19) (23 mg, 0.04 mmol) in 2 ml methanol, is added 23 mg of 10% Pd/C. The hydrogen gas balloon is connected with the reaction flask and the reaction is stirred at room temperature for 60 min. The catalyst is filtered out and the organic solvent is concentrated down under a reduced pressure. The crude product is purified by prep. Analogix column (Gradient: Ethyl acetate/MeOH=1:0 to 1:9) to give (S)—N—((S)-1-Cyclohexyl-2-{(S)-2-[2-(5-fluoro-indol-1-yl)-pyridin-4-yl]-pyrrolidin-1-yl}-2-oxo-ethyl)-2-methylamino-propionamide (Example 24) as a free base (9.9 mg, 55%). M/Z=506.1 [M+1].

Preparation of Example 22

(S)—N—((S)-1-Cyclohexyl-2-{(S)-2-[5-(1H-indol-3-yl)-pyridin-3-yl]-pyrrolidin-1-yl}-2-oxo-ethyl)-2-methylamino-propionamide

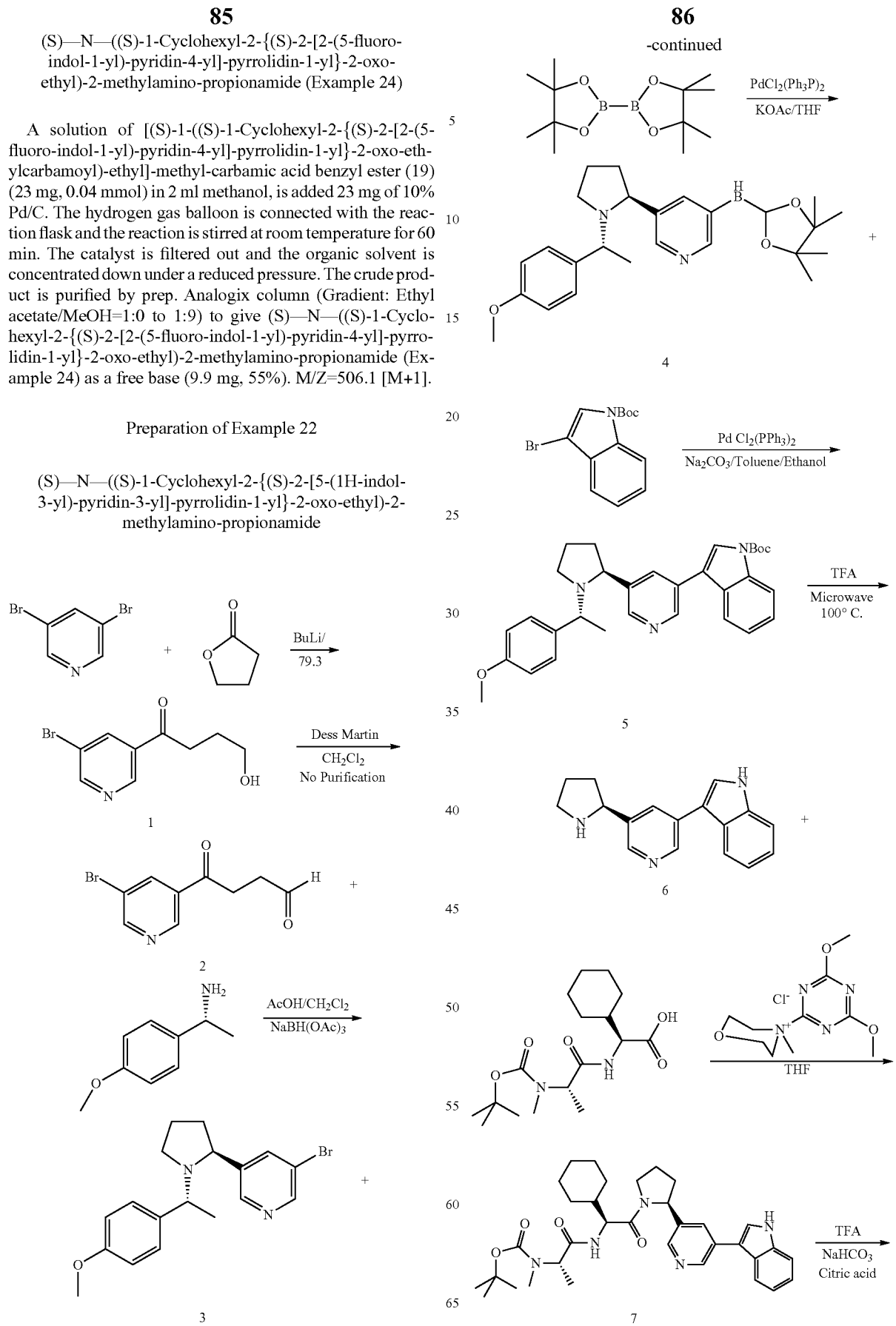

87

-continued

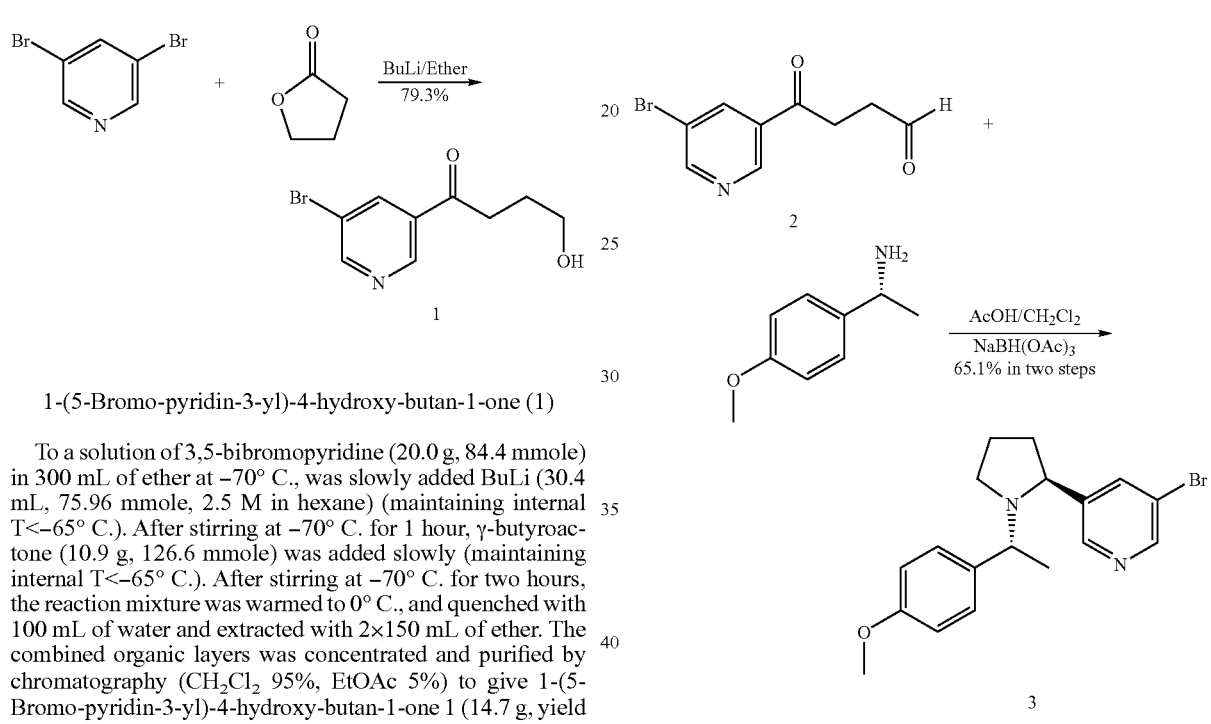

Example 22

Step 1.

1-(5-Bromo-pyridin-3-yl)-4-hydroxy-butan-1-one (1)

To a solution of 3,5-bibromopyridine (20.0 g, 84.4 mmole) in 300 mL of ether at −70° C., was slowly added BuLi (30.4 mL, 75.96 mmole, 2.5 M in hexane) (maintaining internal T<−65° C.). After stirring at −70° C. for 1 hour, γ-butyroactone (10.9 g, 126.6 mmole) was added slowly (maintaining internal T<−65° C.). After stirring at −70° C. for two hours, the reaction mixture was warmed to 0° C., and quenched with 100 mL of water and extracted with 2×150 mL of ether. The combined organic layers was concentrated and purified by chromatography (CH$_2$Cl$_2$ 95%, EtOAc 5%) to give 1-(5-Bromo-pyridin-3-yl)-4-hydroxy-butan-1-one 1 (14.7 g, yield 79%) as pale yellow liquid.

Step 2.

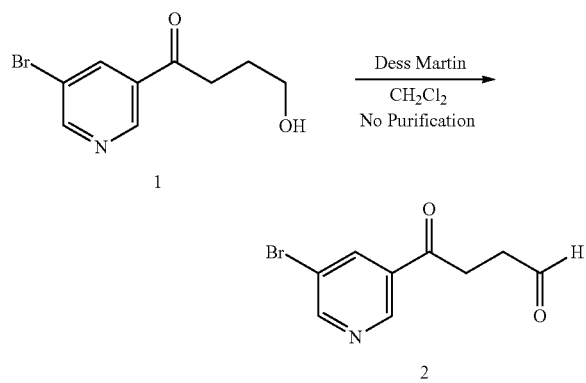

4-(5-Bromo-pyridin-3-yl)-4-oxo-butyraldehyde (2)

To a solution of 1-(5-Bromo-pyridin-3-yl)-4-hydroxy-butan-1-one 1 (5.0 g, 20.5 mmole) in 90 mL of CH$_2$Cl$_2$ at 25° C.,

88 was slowly added a solution of Dess-Martin periodinane (9.6 g, 22.5 mmole) in 70 mL of CH$_2$Cl$_2$. After stirring at 25° C. for 20 minutes, the reaction mixture was diluted with 200 mL of ether and cooled by dry-ice-acetone bath. The solid precipitant was filtered out and discarded, and the filtrate was concentrated. The residue was diluted with 100 mL of ether and cooled by dry-ice-acetone bath and the precipitate was removed by filtration. The filtrate was concentrated to give 6.2 g of 4-(5-Bromo-pyridin-3-yl)-4-oxo-butyraldehyde 2 as a pale/brown oily liquid which turned to a pale brown solid after being cooled to 0° C., which was used without further purification for next step reaction.

Step 3.

3-Bromo-5-{(S)-1-[(R)-1-(4-methoxy-phenyl)-ethyl]-pyrrolidin-2-yl}-pyridine (3)

To a solution of 4-(5-Bromo-pyridin-3-yl)-4-oxo-butyraldehyde 2 (crude from step 2, 20.5 mmole) in 150 mL of CH$_2$Cl$_2$ at −70° C., was slowly added 3.5 mL of acetic acid and triacetoxyl sodium borohydride (10.2 g, 48.0 mmole) and then R-(+)-1-(4-methoxyphenyl)ethylamine (3.9 g, 26.0 mmole) with stirring. After stirring at −70° C. for 1 hour, the reaction mixture was warmed to room temperature. After stirring at room temperature for 2 hours, the reaction mixture was diluted with 200 ml of CH$_2$Cl$_2$, and washed with a solution of 50 mL of water and 20 mL of saturated sodium bicarbonate, and 2×100 mL of water. After concentration, the crude product (dr=86:14 by HPLC analysis) was purified by flash column chromatography (CH$_2$Cl$_2$ 95%, EtOAc 5%) to give 3-Bromo-5-{(S)-1-[(R)-1-(4-methoxy-phenyl)-ethyl]-pyrrolidin-2-yl}-pyridine 3 (3.2 g, yield 44% in two steps) as a light brown viscose liquid.

Step 4

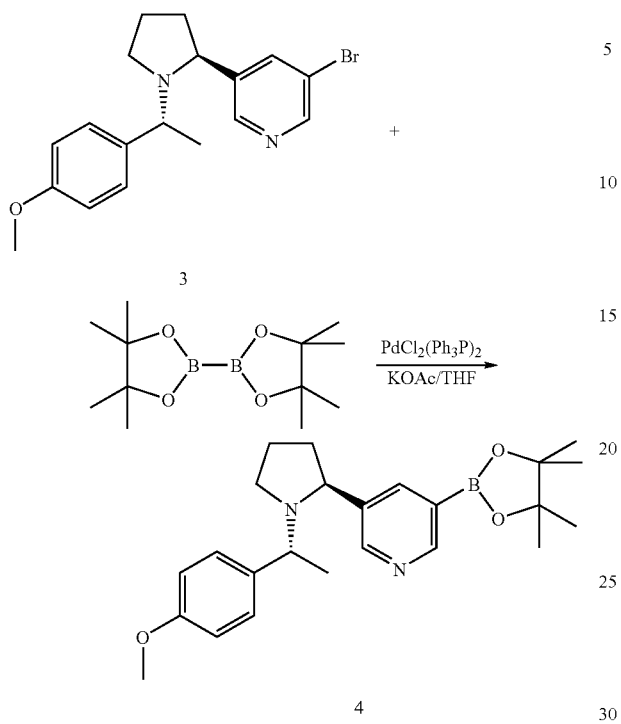

3-{(S)-1-[(R)-1-(4-Methoxy-phenyl)-ethyl]-pyrrolidin-2-yl}-5-(4,4,5,5-tetramethyl-[1,3,2]dioxaborolan-2-yl)-pyridine (4)

The mixture of 3-Bromo-5-{(S)-1-[(R)-1-(4-methoxy-phenyl)-ethyl]-pyrrolidin-2-yl}-pyridine 3 (2.5 g. 6.93 mmole), bis(pinacolato)diboron (2.46 g, 9.67 mmol), dichloro-bis(triphenylphosphine)palladium(II) (1.05 g, 1.5 mmole) and potassium acetate (4.9 g, 50 mmole) in 40 mL of THF was degassed under vacuum. After stirring at 80° C. in a seal glass bottle with nitrogen for 2 hours, the reaction mixture was cooled to room temperature and diluted with 150 mL EtOAc. After filtration, the flitrate was washed with 2×100 mL of water and dried over $Na_2SO_4$, and concentrated to give 3-{(S)-1-[(R)-1-(4-Methoxy-phenyl)-ethyl]-pyrrolidin-2-yl}-5-(4,4,5,5-tetramethyl-[1,3,2]dioxaborolan-2-yl)-pyridine 4 (4.99 g) as a deep brown gum, a crude product without further purification for next step reaction.

Step 5

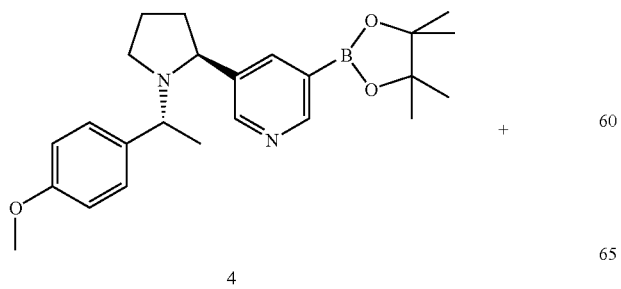

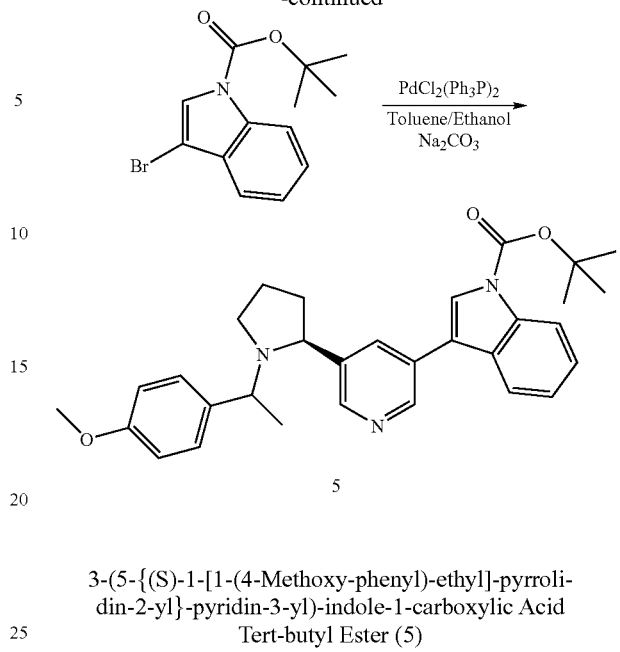

3-(5-{(S)-1-[1-(4-Methoxy-phenyl)-ethyl]-pyrrolidin-2-yl}-pyridin-3-yl)-indole-1-carboxylic Acid Tert-butyl Ester (5)

A mixture of 3-{(S)-1-[(R)-1-(4-Methoxy-phenyl)-ethyl]-pyrrolidin-2-yl}-5-(4,4,5,5-tetramethyl-[1,3,2]dioxaborolan-2-yl)-pyridine 4 (crude, 6.93 mmole), 3-bromo-indole-1-carboxylic acid tert-butyl ester (2.46 g, 8.32 mmole), $Na_2CO_3$ (35 mL, 35 mole, 1 M aqueous) in a mixed solution of 50 mL of toluene and 20 mL of ethanol was degased under vacuum. After heat at 80° C. for 1.5 hours, the reaction mixture was cooled to room temperature and dilutied with 150 mL of EtOAc, and washed by 2×100 mL of water. The organic layer was filtered and concentrated. The crude producte was purified by flash chromatography (Hexane 70%, EtOAc 30%) to give 3-(5-{(S)-1-[1-(4-Methoxy-phenyl)-ethyl]-pyrrolidin-2-yl}-pyridin-3-yl)-indole-1-carboxylic acid tert-butyl ester 5 (2.02 g, 59% in two steps) as light brown gum.

Step 6

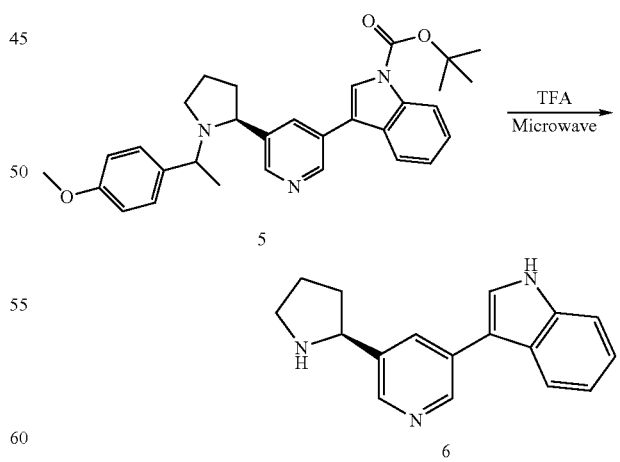

3-((S)-5-Pyrrolidin-2-yl-pyridin-3-yl)-1H-indole (6)

A solution of 3-(5-{(S)-1-[1-(4-Methoxy-phenyl)-ethyl]-pyrrolidin-2-yl}-pyridin-3-yl)-indole-1-carboxylic acid tert-butyl ester 5 (300 mg, 0.63 mmole) in 4 mL of TFA was heated at 100° C. in a microwave reactor for 20 minutes. The result solution was concentrated to remove TFA as much as possible. The residue was purified by HPLC (Column: Waters Sunfire, 30×30 mm; Mobile phase: CH$_3$CN 15% H$_2$O 85% with 0.1% TFA to CH$_3$CN 60% H$_2$O 40% with 0.1% TFA by gradient in 11 minutes; Flow rate 45 mL/minute; Detector: 215 nm UV) to give 3-((S)-5-Pyrrolidin-2-yl-pyridin-3-yl)-1H-indole 6 (78 mg, yield 49%) as white solid.

Step 7

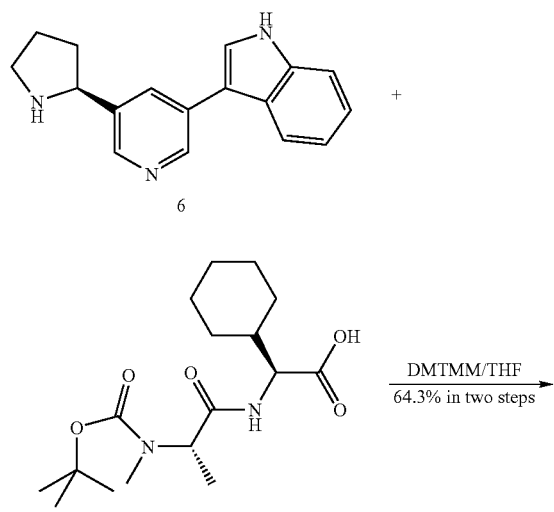

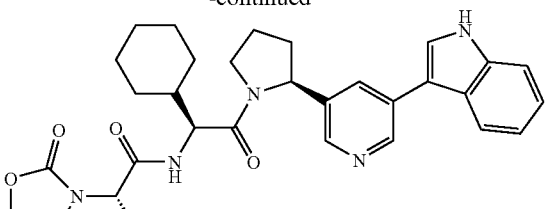

[(S)-1-(S)-1-Cyclohexyl-2-{(S)-2-[5-(1H-indol-3-yl)-pyridin-3-yl]-pyrrolidin-1-yl}-2-oxo-ethylcarbamoyl)-ethyl]-methyl-carbamic Acid Tert-butyl Ester (7)

To a solution of 3-((S)-5-Pyrrolidin-2-yl-pyridin-3-yl)-1H-indole 6 (78 mg, 0.30 mmole) and (S)-[(S)-2-(tert-Butoxycarbonyl-methyl-amino)-propionylamino]-cyclohexyl-acetic acid (111.6 mg, 0.33 mmole) in 5 ml of THF at 0° C., was added 4-(4,6-Dimethoxy-[1,3,5]triazin-2-yl)-4-methyl-morpholinium chloride hydrate (98.6 mg, 0.36 mmole) in one portion. After stirring at 20° C. for 2 hours, the reaction mixture was diluted with 30 mL of EtOAc, washed with 3×10 mL of water and concentration to give [(S)-1-(S)-1-Cyclohexyl-2-{(S)-2-[5-(1H-indol-3-yl)-pyridin-3-yl]-pyrrolidin-1-yl}-2-oxo-ethylcarbamoyl)-ethyl]-methyl-carbamic acid tert-butyl ester 7 (143.5 mg, crude) as pale yellow solid without further purification for next step.

Step 8

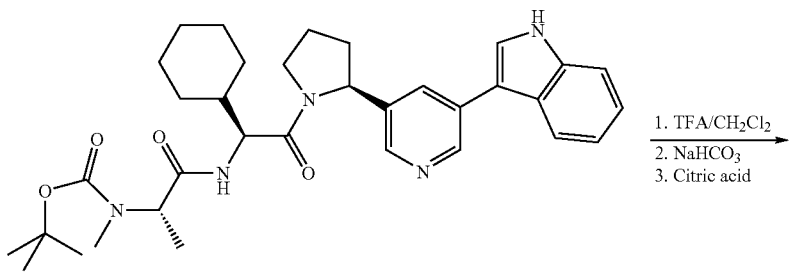

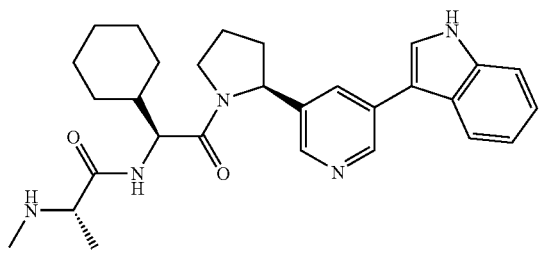

(S)—N—((S)-1-Cyclohexyl-2-{(S)-2-[5-(1H-indol-3-yl)-pyridin-3-yl]-pyrrolidin-1-yl}-2-oxo-ethyl)-2-methylamino-propionamide (8)

To a solution of [(S)-1-((S)-1-Cyclohexyl-2-{(S)-2-[5-(1H-indol-3-yl)-pyridin-3-yl]-pyrrolidin-1-yl}-2-oxo-ethyl-carbamoyl)-ethyl]-methyl-carbamic acid tert-butyl ester 7 (143 mg, crude) in 2 mL of $CH_2Cl_2$ at −20° C., was added 5 mL of TFA (pre-cooled to −20° C.) slowly. After stirring at 0° C. for 20 minutes, the reaction mixture was concentrated to remove TFA as much as possible at room temperature under high vacuum. The crude product was purified by reversed phase HPLC (Column: Waters Sunfire, 30×30 mm; Mobile phase: $CH_3CN$ 15% $H_2O$ 85% with 0.1% TFA to $CH_3CN$ 60% $H_2O$ 40% with 0.1% TFA by gradient in 11 minutes; Flow rate 40 mL/minute; Detector: 215 nm UV) to give product as TFA salt which was dissolved in 30 mL of dichloromethane and basicfied by saturated sodium bicabonate to pH 8. The solution was dried over $Na_2SO_4$ and concentrated to give (S)—N—((S)-1-Cyclohexyl-2-{(S)-2-[5-(1H-indol-3-yl)-pyridin-3-yl]-pyrrolidin-1-yl}-2-oxo-ethyl)-2-methylamino-propionamide Example 22 (17.4 mg) as white solid free base which was dissolved in 5 mL of water with 6.86 mg of citric acid and dried by freeze-drier to give (S)—N—((S)-1-Cyclohexyl-2-{(S)-2-[5-(1H-indol-3-yl)-pyridin-3-yl]-pyrrolidin-1-yl}-2-oxo-ethyl)-2-methylamino-propionamide Example 22 (22.2 mg, yield 12% in three steps) as white citrate salt.

Preparation of Example 54

(S)—N-{(S)-2-[(S)-2-(5-Benzo[1,3]dioxol-5-yl-pyridin-3-yl)-pyrrolidin-1-yl]-1-cyclohexyl-2-oxo-ethyl}-2-methylamino-propionamide

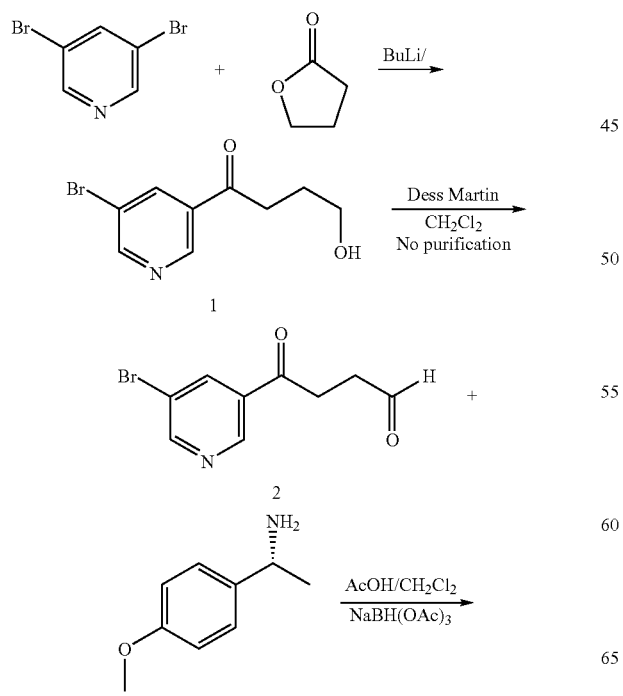

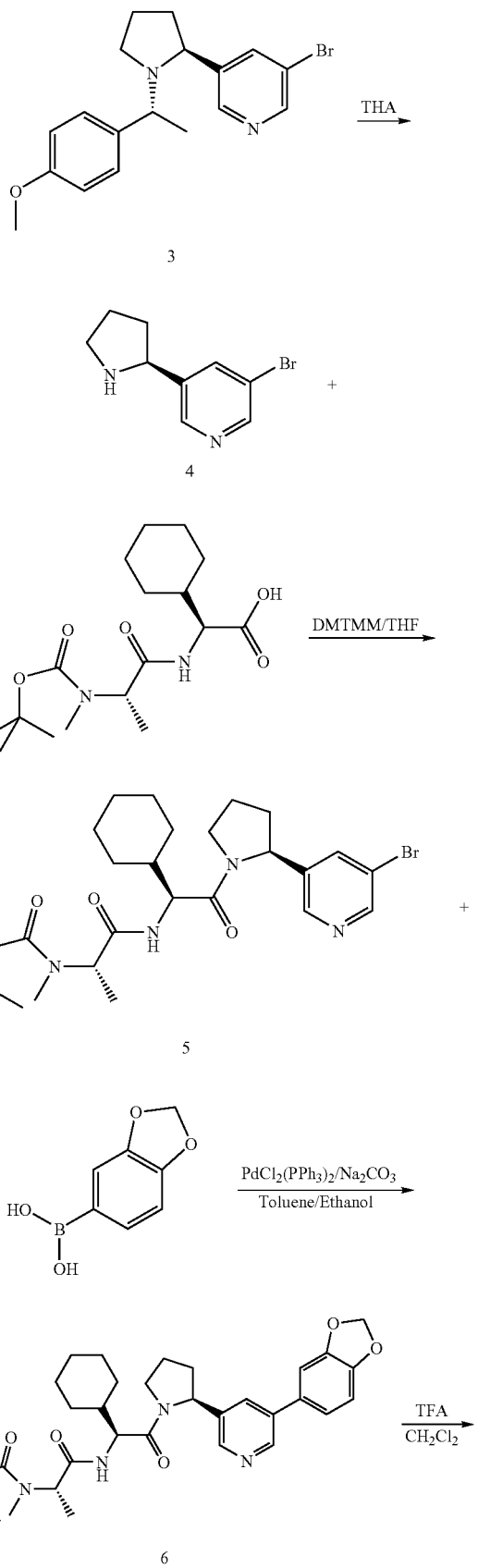

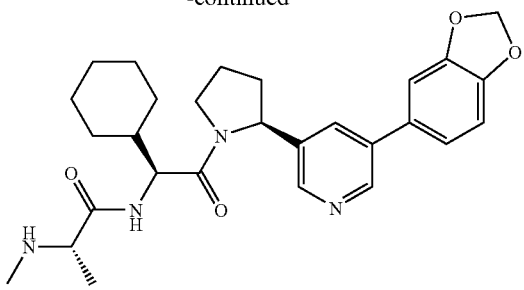

Example 54

Step 1.

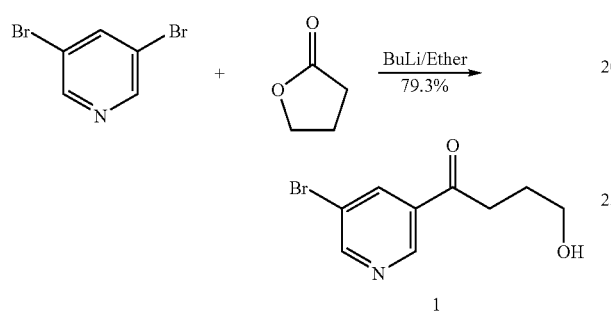

1-(5-Bromo-pyridin-3-yl)-4-hydroxy-butan-1-one (1)

To a solution of 3,5-bibromopyridine (20.0 g, 84.4 mmole) in 300 mL of ether at −70° C., was added BuLi (30.4 mL, 75.96 mmole, 2.5 M in hexane) slowly (maintaining internal T<−65° C.). After stirring at −70° C. for 1 hour, γ-butyroactone (10.9 g, 126.6 mmole) was added slowly (maintaining internal T<−65° C.). After stirring at −70° C. for two hours, the reaction mixture was warmed to 0° C., and quenched with 100 mL of water and extracted with 2×150 mL of ether. The combined organic layers was concentrated and purified by chromatography ($CH_2Cl_2$ 95%, EtOAc 5%) to give 1-(5-Bromo-pyridin-3-yl)-4-hydroxy-butan-1-one 1 (14.7 g, yield 79%) as pale yellow liquid.

Step 2.

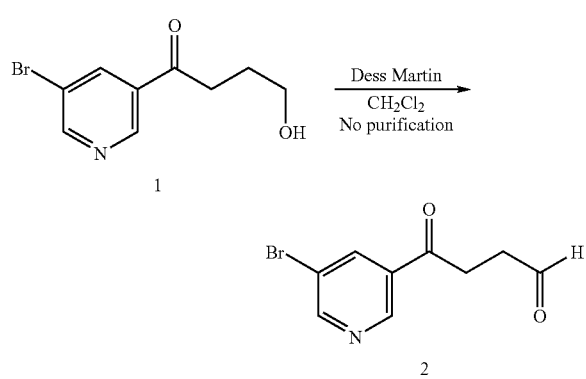

4-(5-Bromo-pyridin-3-yl)-4-oxo-butyraldehyde (2)

To a solution of 1-(5-Bromo-pyridin-3-yl)-4-hydroxy-butan-1-one 1 (5.0 g, 20.5 mmole) in 90 mL of $CH_2Cl_2$ at 25° C., was slowly added a solution of Dess-Martin periodinane (9.6 g, 22.5 mmole) in 70 mL of $CH_2Cl_2$. After stirring at 25° C. for 20 minutes, the reaction mixture was diluted with 200 mL of ether and cooled by dry-ice-acetone bath. The solid precipitant was filtered away and discarded. The filtrate was concentrated and residue was diluted with 100 mL of ether, cooled with in a dry ice-acetone bath and the precipitant was removed by filtration. The filtrate was concentrated to give 6.2 g of 4-(5-Bromo-pyridin-3-yl)-4-oxo-butyraldehyde 2 as a pale/brown oily liquid which turned to a pale/brown solid after cooled to 0° C., without further purification for next step reaction.

Step 3.

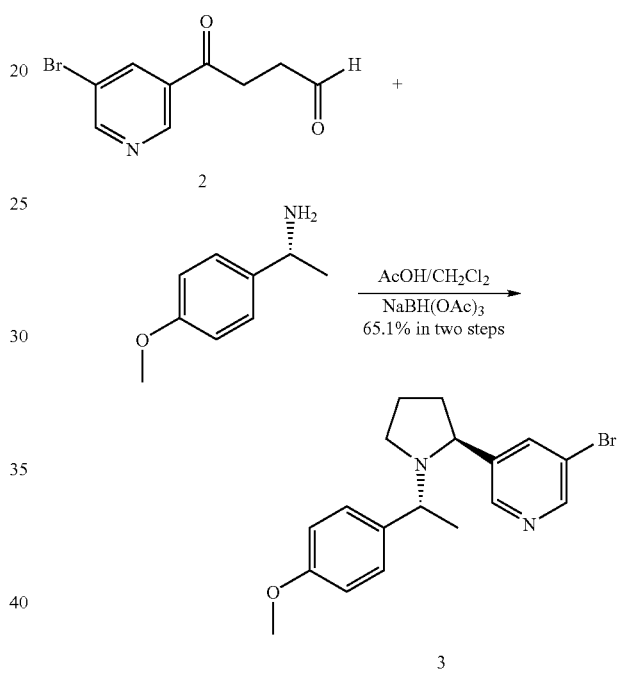

3-Bromo-5-{(S)-1-[(R)-1-(4-methoxy-phenyl)-ethyl]-pyrrolidin-2-yl}-pyridine (3)

To a solution of 4-(5-Bromo-pyridin-3-yl)-4-oxo-butyraldehyde 2 (crude from step 2, 20.5 mmole) in 150 mL of $CH_2Cl_2$ at −70° C., was added 3.5 mL of acetic acid and triacetoxyl sodium borohydride (10.2 g, 48.0 mmole) and then R-(+)-1-(4-methoxyphenyl)ethylamine (3.9 g, 26.0 mmole) slowly with stirring. After stirring at −70° C. for 1 hour, the reaction mixture was warmed to room temperature. After stirring at room temperature for 2 hours, the reaction mixture was diluted with 200 ml of $CH_2Cl_2$, and washed with a solution of 50 mL of water and 20 mL of saturated sodium bicarbonate, and 2×100 mL of water. After concentration, the crude product (dr=86:14 by HPLC analysis) was purified by flash column chromatography ($CH_2Cl_2$ 95%, EtOAc 5%) to give 3-Bromo-5-{(S)-1-[(R)-1-(4-methoxy-phenyl)-ethyl]-pyrrolidin-2-yl}-pyridine 3 (3.2 g, yield 44% in two steps) as a light brown viscose liquid.

Step 4

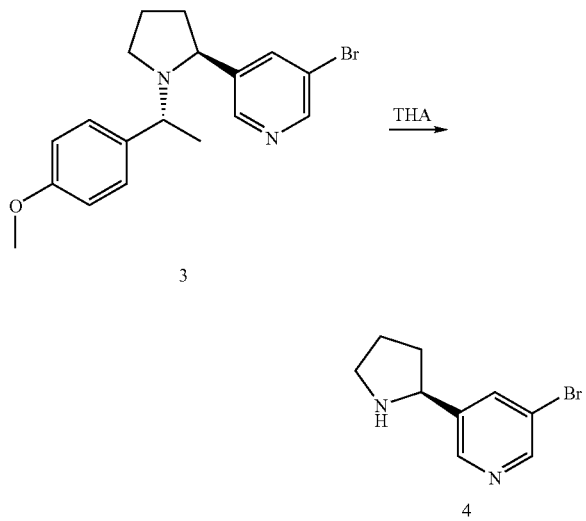

3-((S)-5-Pyrrolidin-2-yl-pyridin-3-yl)-1H-indole (4)

A solution of 3-Bromo-5-{(S)-1-[(R)-1-(4-methoxy-phenyl)-ethyl]-pyrrolidin-2-yl}-pyridine 3 (3.64 g, 10.0 mmole) in 5 mL of TFA was heated at 120° C. in a microwave reactor for 30 minutes. The resulting solution was concentrated to remove TFA. The residue was dissolved in 150 mL of CH$_2$Cl$_2$ and basicfied by 5 mL of saturated NaHCO$_3$. The solution was washed by 2×10 mL of water, dried over Na$_2$SO$_4$ and concentrated to give 3-((S)-5-Pyrrolidin-2-yl-pyridin-3-yl)-1H-indole 4 (2.4 g, crude) as deep brown gum without further purification for the next step reaction.

Step 5

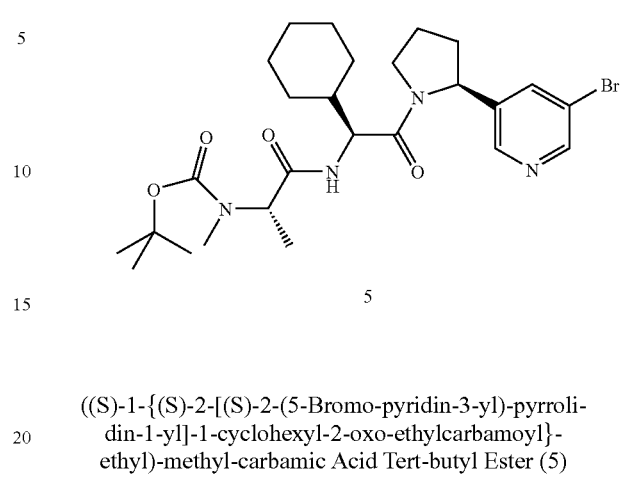

((S)-1-{(S)-2-[(S)-2-(5-Bromo-pyridin-3-yl)-pyrrolidin-1-yl]-1-cyclohexyl-2-oxo-ethylcarbamoyl}-ethyl)-methyl-carbamic Acid Tert-butyl Ester (5)

To a solution of 3-((S)-5-Pyrrolidin-2-yl-pyridin-3-yl)-1H-indole 4 (2.4 g, crude) and (S)-[(S)-2-(tert-Butoxycarbonyl-methyl-amino)-propionylamino]-cyclohexyl-acetic acid (3.42 g, 10.0 mmole) in 100 ml of THF at 0° C., was added 4-(4,6-Dimethoxy-[1,3,5]triazin-2-yl)-4-methyl-morpholinium chloride hydrate (3.04 g, 11.0 mmole) in one portion. After stirring at 20° C. for 2 hours, the reaction mixture was diluted with 100 mL of EtOAc, and washed with 3×50 mL of water. After concentration, the crude product was purified by flash column chromatography (CH$_2$Cl$_2$ 95%, MeOH 5%) to give ((S)-1-{(S)-2-[(S)-2-(5-Bromo-pyridin-3-yl)-pyrrolidin-1-yl]-1-cyclohexyl-2-oxo-ethylcarbamoyl}-ethyl)-methyl-carbamic acid tert-butyl ester 5 (2.47 g, yield 45% in two steps) as a yellow solid.

Step 6

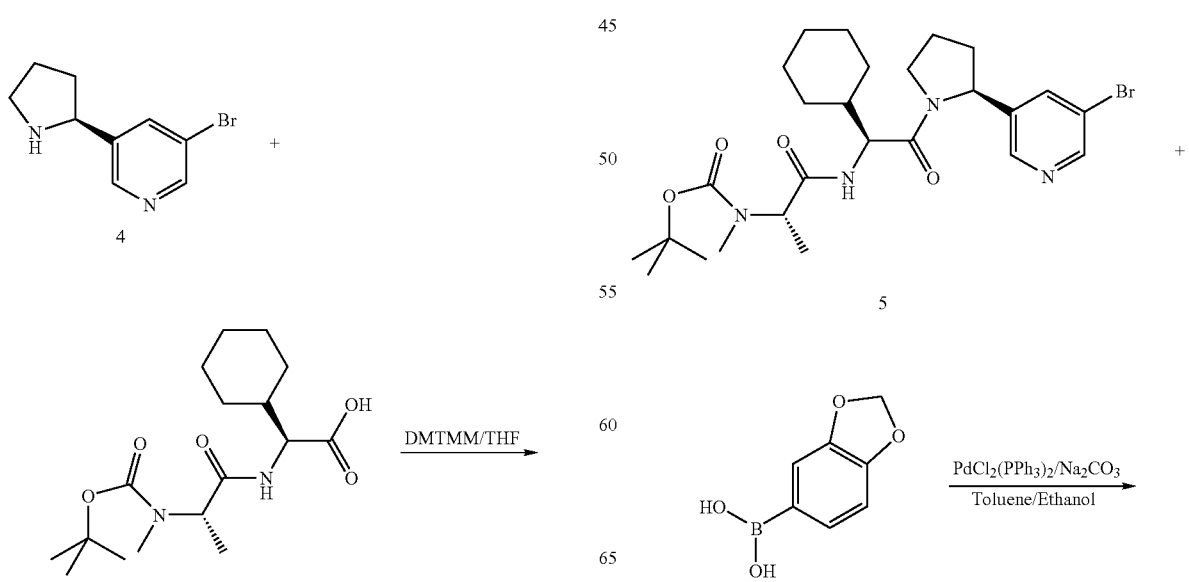

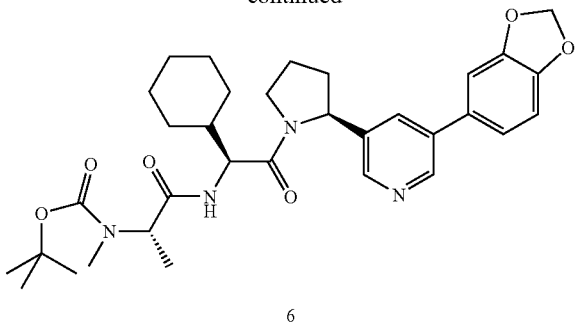

6

((S)-1-{(S)-2-[(S)-2-(5-Benzo[1,3]dioxol-5-yl-pyridin-3-yl)-pyrrolidin-1-yl]-1-cyclohexyl-2-oxo-ethyl-carbamoyl}-ethyl)-methyl-carbamic Acid Tert-butyl Ester (6)

The mixture of ((S)-1-{(S)-2-[(S)-2-(5-Bromo-pyridin-3-yl)-pyrrolidin-1-yl]-1-cyclohexyl-2-oxo-ethylcarbamoyl}-ethyl)-methyl-carbamic acid tert-butyl ester 5 (168 mg, 0.31 mmole), 3,4-(methylene dioxy)pheny boronic acid (60.7 mg, 0.37 mmole), $Na_2CO_3$ (1.8 mL, 1.8 momle, 1 M aqueous) in a mixed solution of 8 mL of toluene and 3 mL of ethanol was degaseq under vacuum. After heat at 80° C. for 1.5 hours, the reaction mixture was cooled to room temperature and diluted with 30 mL of EtOAc, and washed by 3×15 mL of water. The organic layer was filtered and concentrated to give 3-(5-{(S)-1-[1-(4-Methoxy-phenyl)-ethyl]-pyrrolidin-2-yl}-pyridin-3-yl)-indole-1-carboxylic acid tert-butyl ester 6 as crude producte without further purification for next step reaction.
Step 7

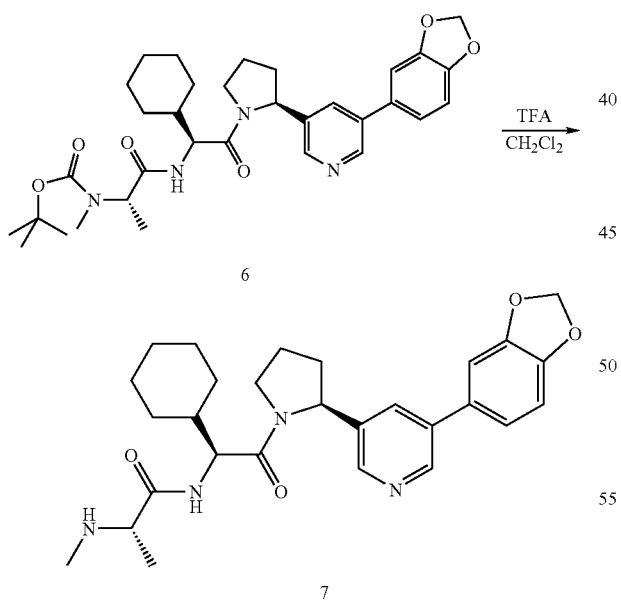

(S)—N-{(S)-2-[(S)-2-(5-Benzo[1,3]dioxol-5-yl-pyridin-3-yl)-pyrrolidin-1-yl]-1-cyclohexyl-2-oxo-ethyl}-2-methylamino-propionamide (Example 54)

To a solution of [(S)-1-(S)-1-Cyclohexyl-2-{(S)-2-[5-(1H-indol-3-yl)-pyridin-3-yl]-pyrrolidin-1-yl}-2-oxo-ethylcarbamoyl)-ethyl]-methyl-carbamic acid tert-butyl ester 6 (crude) in 2 mL of $CH_2Cl_2$ at −20° C., was slowly added 5 mL of TFA (pre-cooled to −20° C.). After stirring at 0° C. for 20 minutes, the reaction mixture was concentrated to remove TFA as much as possible at room temperature under high vacuum. The crude product was purified by reversed phase HPLC (Column: Waters Sunfire, 30×30 mm; Mobile phase: $CH_3CN$ 15%/$H_2O$ 85% with 0.1% TFA to $CH_3CN$ 60%/$H_2O$ 40% with 0.1% TFA by gradient in 11 minutes; Flow rate 40 mL/minute; Detector: 215 nm UV) and concentrated to give (S)—N—((S)-1-Cyclohexyl-2-{(S)-2-[5-(1H-indol-3-yl)-pyridin-3-yl]-pyrrolidin-1-yl}-2-oxo-ethyl)-2-methylamino-propionamide Example 54 (96.1 mg, yield 52% in two steps) as white TFA salt.

In order to measure the ability of the inventive compounds to bind the BIR3 peptide binding pocket an ELISA and a cell based assays are utilized.

Example 136

Elisa

Compounds are incubated with GST-BIR3 fusion protein and biotinylated SMAC peptide (AVPFAQK) in stretavidin-coated 96 well plates. For XIAP BIR3Smac Elisa, a GST-BIR3 fusion containing amino acids 248-358 from XIAP is used. For CIAP1 BIR3Smac Elisa, a GST-BIR3 fusion containing amino acids 259-364 from CIAP1 is used. Following a 30 minute incubation, wells are extensively washed. The remaining GST-BIR3 fusion protein is monitored by ELISA assay involving first, incubation with goat anti-GST antibodies followed by washing and incubation with alkaline phosphatase conjugated anti-goat antibodies. Signal is amplified using Attophos (Promega) and read with Cytoflour Ex 450 nm/40 and Em 580 nm. $IC_{50}$'s correspond to concentration of compound which displaces half of GST-BIR3 signal. The $IC_{50}$ for non-biotinylated Smac is 400 nM. The $IC_{50}$ values of compounds of Examples 1-103 in the described ELISA assays ranged from <0.001-10 μM.

Example 137

Cell Proliferation Assay

The ability of compounds to inhibit tumor cell growth in vitro is monitored using the CellTiter 96® $AQ_{ueous}$ Non-Radioactive Cell Proliferation Assay (Promega). This assay is composed of solutions of a novel tetrazolium compound [3-(4,5-dimethylthiazol-2-yl)-5-(3-carboxymethoxyphenyl)-2-(4-sulfophenyl)-2H-tetrazolium, inner salt; MTS] and an electron coupling reagent (phenazine methosulfate) PMS. MTS is bioreduced by cells into a formazan product, the absorbance of which is measured at 490 nm. The conversion of MTS into the aqueous soluble formazan product is accomplished by dehydrogenase enzymes found in metabolically active cells. The quantity of formazan product as measured by the amount of 490 nm absorbance is directly proportional to the number of living cells in culture. The $IC_{50}$ values of compounds described in Examples 1-103 in this cell assays ranged from <0.001-50 μM.

Example 138

Tablets 1 Comprising Compounds of the Formula (I)

Tablets, comprising, as active ingredient, 50 mg of any one of the compounds of formula (I) mentioned in the preceding Examples 1-103 of the following composition are prepared using routine method:

| Composition: | |
| --- | --- |
| Active Ingredient | 50 mg |
| Wheat starch | 60 mg |
| Lactose | 50 mg |
| Colloidal silica | 5 mg |
| Talcum | 9 mg |
| Magnesium stearate | 1 mg |
| Total | 175 mg |

Manufacture: The active ingredient is combined with part of the wheat starch, the lactose and the colloidal silica and the mixture pressed through a sieve. A further part of the wheat starch is mixed with 5-fold amount of water on a water bath to form a paste and the mixture made first is kneaded with this paste until a weakly plastic mass is formed.

The dry granules are pressed through a sieve having a mesh size of 3 mm, mixed with a pre-sieved mixture (1 mm sieve) of the remaining corn starch, magnesium stearate and talcum and compressed to form slightly biconvex tablets.

Example 139

Tablets 2 Comprising Compounds of the Formula (I)

Tablets, comprising, as active ingredient, 100 mg of any one of the compounds of formula (I) of Examples 1-103 are prepared with the following standard procedures:

| Composition: | |
| --- | --- |
| Active Ingredient | 100 mg |
| Crystalline lactose | 240 mg |
| Avicel | 80 mg |
| PVPPXL | 20 mg |
| Aerosil | 2 mg |
| Magnesium stearate | 5 mg |
| Total | 447 mg |

Manufacture: The active ingredient is mixed with the carrier materials and compressed by means of a tabletting machine (Korsch EKO, Stempeldurchmesser 10 mm).

Example 140

Capsules, comprising as active ingredient, 100 mg of any one of the compounds of formula (I) given in Examples 1-103, of the following composition are prepared according to standard procedures

| Composition: | |
| --- | --- |
| Active Ingredient | 100 mg |
| Avicel | 200 mg |
| PVPPXL | 15 mg |
| Aerosil | 2 mg |
| Magnesium stearate | 1.5 mg |
| Total | 318.5 mg |

Manufacturing is done by mixing the components and filling them into hard gelatine capsules, size 1.

The term "active ingredient" as used herein refers to a compound of Formula I-VII or a pharmaceutically acceptable salt thereof, as defined herein.

The above preferred embodiments are given to illustrate the scope and spirit of the present invention. The descriptions provided herein will make apparent to those skilled in the art other embodiments and examples. These other embodiments and examples are within the contemplation of the present invention. Therefore, the present invention should be limited only by the appended claims.

What is claimed is:

1. A compound of formula I:

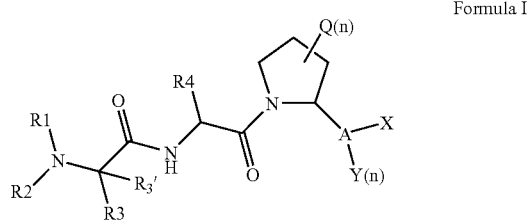

Formula I or a pharmaceutically acceptable salt thereof, wherein
$R_1$ is H, $C_1$-$C_4$ alkyl, $C_2$-$C_4$ alkenyl, $C_2$-$C_4$ alkynyl or $C_3$-$C_{10}$ cycloalkyl, where said $R_1$ is unsubstituted or substituted;
$R_2$ is H, $C_1$-$C_4$ alkyl, $C_2$-$C_4$ alkenyl, $C_2$-$C_4$ alkynyl, $C_3$-$C_{10}$ cycloalkyl, where said $R_2$ is unsubstituted or substituted; or
$R_1$ and $R_2$ may be taken together to form a ring or het;
$R_3$ and $R_3'$ are each independently H, $CF_3$, $C_2F_5$, $C_1$-$C_4$ alkyl, $C_2$-$C_4$ alkenyl, $C_2$-$C_4$ alkynyl, $CH_2$—Z or $R_2$ and $R_3$ taken together with the nitrogen atom to which they are attached form het, wherein said alkyl, said alkenyl, said alkynyl and said het ring are unsubstituted or substituted;
Z is H, OH, F, Cl, $CH_3$, $CH_2Cl$, $CH_2F$ or $CH_2OH$;
$R_4$ is $C_{0-10}$ alkyl, $C_{0-10}$ alkyl-$C_{3-10}$ cycloalkyl, $C_{0-10}$alkyl-$C_{6-10}$aryl, $C_{0-10}$alkyl-het, wherein any carbon may be replaced with a heteroatom or group from the list N, O, $S(O)_r$ and any atom may be unsubstituted or substituted;
A is a 6 membered heteroaryl ring;
r is 0, 1, or 2;
Q and Y are each independently H, F, Cl, Br, I, $C_1$-$C_{10}$ alkyl, $C_1$-$C_{10}$ alkoxy, aryl $C_1$-$C_{10}$ alkoxy, OH, O—$C_1$-$C_{10}$-alkyl, $(CH_2)_{0-6}$—$C_3$-$C_7$ cycloalkyl, aryl, aryl $C_1$-$C_{10}$ alkyl, O—$(CH_2)_{0-6}$ aryl, $(CH_2)_{1-6}$het, het, O—$(CH_2)_{1-6}$het, —$OR_{11}$, $C(O)R_{11}$, —$C(O)N(R_{11})(R_{12})$, $N(R_{11})(R_{12})$, $SR_{11}$, $S(O)R_{11}$, $S(O)_2R_{11}$, $S(O)_2$—$N(R_{11})(R_{12})$, or $NR_{11}$—$S(O)_2$—$(R_{12})$, wherein said alkyl, said cycloalkyl and said aryl are unsubstituted or substituted, independent Q's may be joined to form a 5-10 membered ring;
X is a substituted or unsubstituted aryl, $C_3$-$C_{10}$ cycloalkyl, or het, where the substituents on said aryl, said $C_3$-$C_{10}$ cycloalkyl and said het are alkyl, halo, lower alkoxy, $NR_5R_6$, CN, $NO_2$ or $SR_5$;
$R_5$ and $R_6$ are each independently H, F, Cl, Br, I, $C_1$-$C_{10}$ alkyl, $C_1$-$C_{10}$ alkoxy, aryl $C_1$-$C_{10}$ alkoxy, OH, O—$C_1$-$C_{10}$-alkyl, $(CH_2)_{0-6}$—$C_3$-$C_7$ cycloalkyl, aryl, aryl $C_1$-$C_{10}$ alkyl, O—$(CH_2)_{0-6}$ aryl, $(CH_2)_{1-6}$het, het, O—$(CH_2)_{1-6}$het, —$OR_{11}$, $C(O)R_{11}$, —$C(O)N(R_{11})(R_{12})$, $N(R_{11})(R_{12})$, $SR_{11}$, $S(O)R_{11}$, $S(O)_2R_{11}$, $S(O)_2$—$N(R_{11})(R_{12})$, or $NR_{11}$—$S(O)_2$—$(R_{12})$,
each n is independently 0, 1, 2, 3, 4, 5, 6 or 7;
het is a 5-7 membered monocyclic heterocyclic ring containing 1-4 heteroring atoms selected from N, O and S or an 8-12 membered fused ring system that includes one 5-7 membered heterocyclic ring containing 1, 2, or 3 heteroring atoms selected from N, O and S, where said het is unsubstituted or substituted;

$R_{11}$ and $R_{12}$ are each independently H, $C_1$-$C_{10}$ alkyl, $(CH_2)_{0-6}$—$C_3$-$C_7$cycloalkyl, $(CH_2)_{0-6}$—$(CH)_{0-1}$(aryl)$_{1-2}$, C(O)—$C_1$-$C_{10}$alkyl, —C(O)—$(CH_2)_{0-6}$—$C_3$-$C_7$cycloalkyl, —C(O)—O—$(CH_2)_{0-6}$-aryl, —C(O)—$(CH_2)_{0-6}$-O-fluorenyl, C(O)—NH—$(CH_2)_{0-6}$-aryl, C(O)—$(CH_2)_{0-6}$-aryl, C(O)—$(CH_2)_{0-6}$-het, —C(S)—$C_1$-$C_{10}$alkyl, —C(S)—$(CH_2)_{0-6}$—$C_3$-$C_7$cycloalkyl, —C(S)—O—$(CH_2)_{0-6}$-aryl, —C(S)—$(CH_2)_{0-6}$—O-fluorenyl, C(S)—NH—$(CH_2)_{0-6}$-aryl, —C(S)—$(CH_2)_{0-6}$-aryl or C(S)—$(CH_2)_{0-6}$-het, C(O)$R_{11}$, C(O)$NR_{11}R_{12}$, C(O)O$R_{11}$, S(O)n$R_{11}$, S(O)$_m NR_{11}R_{12}$, m=1 or 2, C(S)$R_{11}$, C(S)$NR_{11}R_{12}$, C(S)O$R_{11}$, wherein said alkyl, said cycloalkyl and said aryl are unsubstituted or substituted; or $R_{11}$ and $R_{12}$ together with the nitrogen atom form het;

wherein the alkyl substituents of $R_{11}$ and $R_{12}$ may be unsubstituted or substituted by one or more substituents selected from $C_1$-$C_{10}$alkyl, halogen, OH, O—$C_1$-$C_6$alkyl, $CF_3$ or $NR_{11}R_{12}$;

substituted cycloalkyl substituents of $R_{11}$ and $R_{12}$ are substituted by one or more substituents selected from a $C_2$-$C_{10}$ alkene, $C_1$-$C_6$alkyl, halogen, OH, O—$C_1$-$C_6$alkyl, S—$C_1$-$C_6$alkyl, $CF_3$, or $NR_{11}R_{12}$ and substituted het or substituted aryl of $R_{11}$ and $R_{12}$ are substituted by one or more substituents selected from halogen, hydroxy, $C_1$-$C_4$ alkyl, $C_1$-$C_4$ alkoxy, nitro, CN, O—C(O)—$C_1$-$C_4$alkyl and C(O)—O—$C_1$-$C_4$-alkyl;

wherein the substituents on $R_1$, $R_2$, $R_3$, $R_4$, Q, and A and X groups are each independently halo, hydroxy, lower alkyl, lower alkenyl, lower alkynyl, lower alkanoyl, lower alkoxy, aryl, aryl lower alkyl, amino, amino lower alkyl, diloweralkylamino, lower alkanoyl, amino lower alkoxy, nitro, cyano, cyano lower alkyl, carboxy, lower carbalkoxy, lower alkanoyl, aryloyl, lower arylalkanoyl, carbamoyl, N-mono- or N,N-dilower alkyl carbamoyl, lower alkyl carbamic acid ester, amidino, guanidine, ureido, mercapto, sulfo, lower alkylthio, sulfoamino, sulfonamide, benzosulfonamide, sulfonate, sulfanyl lower alkyl, aryl sulfonamide, halogen substituted aryl sulfonate, lower alkylsulfinyl, arylsulfinyl; aryl-lower alkylsulfinyl, lower alkylarylsulfinyl, lower alkylsulfonyl, arylsulfonyl, aryl-lower alkylsulfonyl, lower aryl alkyl lower alkylarylsulfonyl, halogen-lower alkylmercapto, halogen-lower alkylsulfonyl, phosphono (—P(=O)(OH)$_2$), hydroxy-lower alkoxy phosphoryl or di-lower alkoxyphosphoryl, ($R_9$)NC(O)—$NR_{10}R_{13}$, lower alkyl carbamic acid ester or carbamates or —$NR_8R_{14}$, wherein $R_8$ and $R_{14}$ can be the same or different and are independently H or lower alkyl, or $R_8$ and $R_{14}$ together with the N atom form a 3- to 8-membered heterocyclic ring containing a nitrogen heteroring atoms and may optionally contain one or two additional heteroring atoms selected from nitrogen, oxygen and sulfur, which heterocyclic ring may be unsubstituted or substituted with lower alkyl, halo, lower alkenyl, lower alkynyl, hydroxy, lower alkoxy, nitro, amino, lower alkyl, amino, diloweralkyl amino, cyano, carboxy, lower carbalkoxy, formyl, lower alkanoyl, oxo, carbarmoyl, N-lower or N,N-dilower alkyl carbamoyl, mercapto, or lower alkylthio, and $R_9$, $R_{10}$, and $R_{13}$ are independently hydrogen, lower alkyl, halogen substituted lower alkyl, aryl, aryl lower alkyl, halogen substituted aryl, halogen substituted aryl lower alkyl.

2. A compound according to claim 1 wherein:
$R_1$ is H, $C_1$-$C_4$ alkyl, where said $C_1$-$C_4$ alkyl is unsubstituted or substituted;
$R_2$ is H, $C_1$-$C_4$ alkyl, where said $C_1$-$C_4$ alkyl is unsubstituted or substituted;
$R_3$ and $R_3'$ are each independently H, or $C_1$-$C_4$ alkyl;
$R_4$ is $C_5$-$C_7$ cycloalkyl or $C_1$-$C_4$ alkyl;
A is a 6 membered heteroaryl ring;
Q and Y are independently H, F, Cl, Br, I, $C_1$-$C_{10}$ alkyl, or $C_1$-$C_{10}$ alkoxy;
X is a substituted or unsubstituted aryl, $C_3$-$C_{10}$ cycloalkyl, or het;
or a pharmaceutically acceptable salt thereof.

3. A compound according to claim 1 wherein:
$R_1$ is H, or methyl;
$R_2$ is H, or methyl;
one of $R_3$ and $R_3'$ is H and the other is methyl;
$R_4$ is cyclohexyl, or isopropyl;
A is pyridyl, or pyrimidinyl where A is unsubstituted or substituted with lower alkyl or halo;
Q and Y are each independently H, F or Cl, lower alkyl, where said lower alkyl is optionally substituted with trifluoromethyl, lower alkoxy, or lower alkyl amino; and
X is quinolinyl, isoquinolyl, benzothiazolyl, pyridinyl, indolyl, benzoimidazolyl, naphthyl, benzo[1,3]dioxolyl, benzofurnayl, naphthyridine, pyrrolo[2,3-b]pyridinyl, indanzolyl, benzotriazolyl, indazolyl, 2-oxobenzooxazolyl, or phenyl, where X is substituted or unsubstituted;
or a pharmaceutically acceptable salt thereof.

4. A pharmaceutical composition comprising a therapeutically effective amount of a compound according to claim 1.

5. The compound of claim 1, where Formula I has the following stereochemistry

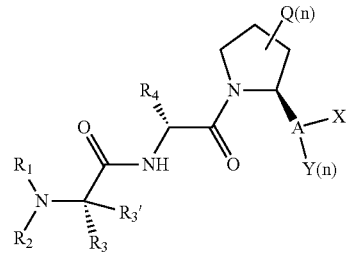

or a pharmaceutically acceptable salt thereof.

6. The compound of claim 1, where Formula I has the following stereochemistry

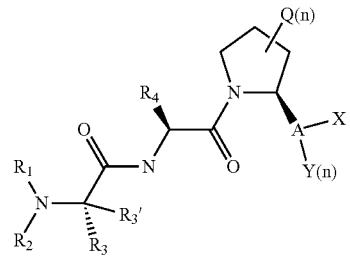

or a pharmaceutically acceptable salt thereof.

7. The compound of claim 5 wherein
$R_1$ is H, $C_1$-$C_4$ alkyl, where said $C_1$-$C_4$ alkyl is unsubstituted or substituted;

$R_2$ is H, $C_1$-$C_4$ alkyl, where said $C_1$-$C_4$ alkyl is unsubstituted or substituted;
$R_3$ is H, or $C_1$-$C_4$ alkyl;
$R_3'$ is H;
$R_4$ is $C_5$-$C_7$ cycloalkyl or $C_1$-$C_4$ alkyl;
A is a 6 membered heteroaryl ring;
Q and Y are independently H, F, Cl, Br, I, $C_1$-$C_{10}$ alkyl, or $C_1$-$C_{10}$ alkoxy;
X is a substituted or unsubstituted aryl, $C_3$-$C_{10}$ cycloalkyl, or het;
or a pharmaceutically acceptable salt thereof.

8. The compound of claim 6 wherein
$R_1$ is H or methyl;
$R_2$ is H or methyl;
$R_3$ is methyl;
$R_3'$ is H;
$R_4$ is cyclohexyl or isopropyl;
A is pyridyl, or pyrimidinyl where A is unsubstituted or substituted with lower alkyl or halo;
Q and Y are each independently H, F or Cl, lower alkyl, where said lower alkyl is optionally substituted with trifluoromethyl, lower alkoxy or lower alkyl amino; and
X is quinolinyl, isoquinolyl, benzothiazolyl, pyridinyl, indolyl, benzoimidazolyl, naphthyl, benzo[1,3]dioxolyl, benzofurnayl, naphthyridine, pyrrolo[2,3-b]pyridinyl, indanzolyl, benzotriazolyl, indazolyl, 2-oxobenzooxazolyl, or phenyl, where X is substituted or unsubstituted;
or a pharmaceutically acceptable salt thereof.

9. A compound selected from the group consisting of
(S)—N—((S)-1-Cyclohexyl-2-{(S)-2-[2-(2,3-dihydro-indol-1-yl)-pyridin-4-yl]-pyrrolidin-1-yl}-2-oxo-ethyl)-2-methylamino-propionamide;
(S)—N—((S)-1-Cyclohexyl-2-{(S)-2-[5-(2,3-dihydro-indol-1-yl)-pyridin-3-yl]-pyrrolidin-1-yl}-2-oxo-ethyl)-2-methylamino-propionamide;
(S)—N—((R)-1-Cyclohexyl-2-{(S)-2-[5-(2,3-dihydro-indol-1-yl)-pyridin-3-yl]-pyrrolidin-1-yl}-2-oxo-ethyl)-2-methylamino-propionamide;
(S)—N—((S)-1-Cyclohexyl-2-{(S)-2-[2-(3,4-dihydro-2H-quinolin-1-yl)-pyridin-4-yl]-pyrrolidin-1-yl}-2-oxo-ethyl)-2-methylamino-propionamide;
(S)—N—((S)-1-Cyclohexyl-2-{(S)-2-[2-(2,3-dihydro-pyrrolo[2,3-b]pyridin-1-yl)-pyridin-4-yl]-pyrrolidin-1-yl}-2-oxo-ethyl)-2-methylamino-propionamide;
(S)-N-{(S)-1-Cyclohexyl-2-[(S)-2-(5-indol-1-yl-pyridin-3-yl)-pyrrolidin-1-yl]-2-oxo-ethyl}-2-methylamino-propionamide;
(S)—N—((S)-1-Cyclohexyl-2-{(S)-2-[5-(3,4-dihydro-2H-quinolin-1-yl)-pyridin-3-yl]-pyrrolidin-1-yl}-2-oxo-ethyl)-2-methylamino-propionamide;
(S)—N—((S)-1-Cyclohexyl-2-oxo-2-{(S)-2-[2-(2-oxo-3,4-dihydro-2H-quinolin-1-yl)-pyridin-4-yl]-pyrrolidin-1-yl}-ethyl)-2-methylamino-propionamide;
(S)—N—((S)-1-Cyclohexyl-2-{(S)-2-[2-(6-fluoro-2,3-dihydro-indol-1-yl)-pyridin-4-yl]-pyrrolidin-1-yl}-2-oxo-ethyl)-2-methylamino-propionamide;
(S)—N—((S)-1-{(S)-2-[2-(6-Fluoro-2,3-dihydro-indol-1-yl)-pyridin-4-yl]-pyrrolidine-1-carbonyl}-2-methyl-propyl)-2-methylamino-propionamide;
(S)—N-{(S)-1-Cyclohexyl-2-[(S)-2-(2-isoquinolin-4-yl-pyridin-4-yl)-pyrrolidin-1-yl]-2-oxo-ethyl}-2-methylamino-propionamide;
(S)—N-{(S)-1-Cyclohexyl-2-[(R)-2-(2-isoquinolin-4-yl-pyridin-4-yl)-pyrrolidin-1-yl]-2-oxo-ethyl}-2-methylamino-propionamide;
(S)—N—((S)-1-Cyclohexyl-2-{(S)-2-[2-(5-fluoro-2,3-dihydro-indol-1-yl)-pyridin-4-yl]-pyrrolidin-1-yl}-2-oxo-ethyl)-2-methylamino-propionamide;
(S)—N-{(S)-1-Cyclohexyl-2-[(S)-2-(2-indazol-1-yl-pyridin-4-yl)-pyrrolidin-1-yl]-2-oxo-ethyl}-2-methylamino-propionamide;
(S)—N-{(S)-2-[(S)-2-(5-Benzofuran-3-yl-pyridin-3-yl)-pyrrolidin-1-yl]-1-cyclohexyl-2-oxo-ethyl}-2-methylamino-propionamide;
(S)—N-{(S)-2-[(S)-2-(2-Benzoimidazol-1-yl-pyridin-4-yl)-pyrrolidin-1-yl]-1-cyclohexyl-2-oxo-ethyl}-2-methylamino-propionamide;
(S)—N—((S)-1-Cyclohexyl-2-{(S)-2-[2-(3-methyl-indol-1-yl)-pyridin-4-yl]-pyrrolidin-1-yl}-2-oxo-ethyl)-2-methylamino-propionamide;
(S)-2-Methylamino-N—((S)-2-methyl-1-{(S)-2-[2-(3-methyl-indol-1-yl)-pyridin-4-yl]-pyrrolidine-1-carbonyl}-propyl)-propionamide;
(S)—N—((S)-1-Cyclohexyl-2-{(S)-2-[5-(1H-indol-3-yl)-pyridin-3-yl]-pyrrolidin-1-yl}-2-oxo-ethyl)-2-methylamino-propionamide;
(S)—N-{(S)-2-[(S)-2-(2-Benzotriazol-1-yl-pyridin-4-yl)-pyrrolidin-1-yl]-1-cyclohexyl-2-oxo-ethyl}-2-methylamino-propionamide;
(S)—N—((S)-1-Cyclohexyl-2-{(S)-2-[2-(5-fluoro-indol-1-yl)-pyridin-4-yl]-pyrrolidin-1-yl}-2-oxo-ethyl)-2-methylamino-propionamide;
(S)—N—((S)-1-Cyclohexyl-2-{(S)-2-[2-(6-fluoro-3,4-dihydro-2H-quinolin-1-yl)-pyridin-4-yl]-pyrrolidin-1-yl}-2-oxo-ethyl)-2-methylamino-propionamide;
(S)—N—((S)-1-Cyclohexyl-2-{(S)-2-[2-(1H-indol-2-yl)-pyridin-4-yl]-pyrrolidin-1-yl}-2-oxo-ethyl)-2-methylamino-propionamide;
(S)—N—((S)-1-Cyclohexyl-2-{(S)-2-[5-(5-fluoro-2,3-dihydro-indol-1-yl)-pyridin-3-yl]-pyrrolidin-1-yl}-2-oxo-ethyl)-2-methylamino-propionamide;
(S)—N—((S)-1-Cyclohexyl-2-{(S)-2-[2-(1H-indol-3-yl)-pyridin-4-yl]-pyrrolidin-1-yl}-2-oxo-ethyl)-2-methylamino-propionamide;
(S)—N—((S)-1-{(S)-2-[2-(6-Fluoro-indol-1-yl)-pyridin-4-yl]-pyrrolidine-1-carbonyl}-2-methyl-propyl)-2-methylamino-propionamide;
(S)—N—((S)-1-Cyclohexyl-2-{(R)-2-[2-(6-fluoro-indol-1-yl)-pyridin-4-yl]-pyrrolidin-1-yl}-2-oxo-ethyl)-2-methylamino-propionamide;
(S)—N—((S)-1-Cyclohexyl-2-{(S)-2-[2-(6-fluoro-indol-1-yl)-pyridin-4-yl]-pyrrolidin-1-yl}-2-oxo-ethyl)-2-methylamino-propionamide;
(S)—N—((S)-1-Cyclohexyl-2-oxo-2-{(S)-2-[5-(2-oxo-benzooxazol-3-yl)-pyridin-3-yl]-pyrrolidin-1-yl}-ethyl)-2-methylamino-propionamide;
(S)—N—((S)-1-Cyclohexyl-2-{(S)-2-[2-(1,3-dihydro-isoindol-2-yl)-pyridin-4-yl]-pyrrolidin-1-yl}-2-oxo-ethyl)-2-methylamino-propionamide;
(S)—N—((S)-1-Cyclohexyl-2-{(S)-2-[2-(3,4-dihydro-1H-isoquinolin-2-yl)-pyridin-4-yl]-pyrrolidin-1-yl}-2-oxo-ethyl)-2-methylamino-propionamide;
(S)—N-{(S)-2-[(S)-2-(5-Benzoimidazol-1-yl-pyridin-3-yl)-pyrrolidin-1-yl]-1-cyclohexyl-2-oxo-ethyl}-2-methylamino-propionamide;
(S)—N-{(S)-2-[(S)-2-(5-Benzotriazol-1-yl-pyridin-3-yl)-pyrrolidin-1-yl]-1-cyclohexyl-2-oxo-ethyl}-2-methylamino-propionamide;
(S)—N-{(S)-1-Cyclohexyl-2-[(S)-2-(5-indazol-1-yl-pyridin-3-yl)-pyrrolidin-1-yl]-2-oxo-ethyl}-2-methylamino-propionamide;

(S)—N—((S)-1-Cyclohexyl-2-{(S)-2-[2-(5-fluoro-3-methyl-indol-1-yl)-pyridin-4-yl]-pyrrolidin-1-yl}-2-oxo-ethyl)-2-methylamino-propionamide;

(S)—N—((S)-1-{(S)-2-[2-(5-Fluoro-3-methyl-indol-1-yl)-pyridin-4-yl]-pyrrolidine-1-carbonyl}-2-methyl-propyl)-2-methylamino-propionamide;

(S)—N—((S)-1-Cyclohexyl-2-{(S)-2-[5-(3-methyl-indol-1-yl)-pyridin-3-yl]-pyrrolidin-1-yl}-2-oxo-ethyl)-2-methylamino-propionamide;

(S)—N—((S)-1-Cyclohexyl-2-{(S)-2-[5-(5-fluoro-3-methyl-indol-1-yl)-pyridin-3-yl]-pyrrolidin-1-yl}-2-oxo-ethyl)-2-methylamino-propionamide;

(S)—N—((S)-1-Cyclohexyl-2-{(S)-2-[5-(5-fluoro-indol-1-yl)-pyridin-3-yl]-pyrrolidin-1-yl}-2-oxo-ethyl)-2-methylamino-propionamide;

(S)—N-{(S)-1-Cyclohexyl-2-oxo-2-[(S)-2-(5-pyrrolo[2,3-b]pyridin-1-yl-pyridin-3-yl)-pyrrolidin-1-yl]-ethyl}-2-methylamino-propionamide;

(S)—N-{(S)-2-[(S)-2-(2-Benzoimidazol-1-yl-3-fluoro-pyridin-4-yl)-pyrrolidin-1-yl]-1-cyclohexyl-2-oxo-ethyl}-2-methylamino-propionamide;

(S)—N-{(S)-1-[(S)-2-(2-Benzoimidazol-1-yl-pyridin-4-yl)-pyrrolidine-1-carbonyl]-2-methyl-propyl}-2-methylamino-propionamide;

3-(5-{(S)-1-[(S)-2-Cyclohexyl-2-((S)-2-methylamino-propionylamino)-acetyl]-pyrrolidin-2-yl}-pyridin-3-yl)-indole-1-carboxylic acid dimethylamide;

(S)—N—((S)-1-Cyclohexyl-2-{(S)-2-[5-(1-ethyl-1H-indol-3-yl)-pyridin-3-yl]-pyrrolidin-1-yl}-2-oxo-ethyl)-2-methylamino-propionamide;

(S)—N-{(S)-1-Cyclohexyl-2-[(S)-2-(5-naphthalen-1-yl-pyridin-3-yl)-pyrrolidin-1-yl]-2-oxo-ethyl}-2-methylamino-propionamide;

(S)—N—((S)-1-Cyclohexyl-2-{(S)-2-[4-(6-fluoro-2,3-dihydro-indol-1-yl)-pyridin-2-yl]-pyrrolidin-1-yl}-2-oxo-ethyl)-2-methylamino-propionamide;

(S)—N—((S)-1-Cyclohexyl-2-{(S)-2-[4-(5-fluoro-2,3-dihydro-indol-1-yl)-pyridin-2-yl]-pyrrolidin-1-yl}-2-oxo-ethyl)-2-methylamino-propionamide;

(S)—N—((S)-2-{(S)-2-[5-(5-Chloro-2-methoxy-phenyl)-pyridin-3-yl]-pyrrolidin-1-yl}-1-cyclohexyl-2-oxo-ethyl)-2-methylamino-propionamide;

(S)—N-{(S)-1-Cyclohexyl-2-oxo-2-[(S)-2-(5-o-tolyl-pyridin-3-yl)-pyrrolidin-1-yl]-ethyl}-2-methylamino-propionamide;

(S)—N-{(S)-2-[(S)-2-(5-Benzo[1,3]dioxol-5-yl-pyridin-3-yl)-pyrrolidin-1-yl]-1-cyclohexyl-2-oxo-ethyl}-2-methylamino-propionamide;

(S)—N—((S)-1-Cyclohexyl-2-oxo-2-{(S)-2-[5-(3-trifluoromethyl-phenyl)-pyridin-3-yl]-pyrrolidin-1-yl}-ethyl)-2-methylamino-propionamide;

(S)—N—((S)-1-Cyclohexyl-2-{(S)-2-[5-(3-isopropyl-phenyl)-pyridin-3-yl]-pyrrolidin-1-yl}-2-oxo-ethyl)-2-methylamino-propionamide;

(S)—N-{(S)-1-Cyclohexyl-2-[(S)-2-(5-naphthalen-2-yl-pyridin-3-yl)-pyrrolidin-1-yl]-2-oxo-ethyl}-2-methylamino-propionamide;

(S)—N—((S)-2-{(S)-2-[2-Chloro-5-(3-trifluoromethyl-phenyl)-pyridin-3-yl]-pyrrolidin-1-yl}-1-cyclohexyl-2-oxo-ethyl)-2-methylamino-propionamide;

(S)—N—((S)-2-{(S)-2-[5-(3,5-Bis-trifluoromethyl-phenyl)-pyridin-3-yl]-pyrrolidin-1-yl}-1-cyclohexyl-2-oxo-ethyl)-2-methylamino-propionamide;

(S)—N—((S)-1-Cyclohexyl-2-oxo-2-{(S)-2-[5-(2-trifluoromethyl-phenyl)-pyridin-3-yl]-pyrrolidin-1-yl}-ethyl)-2-methylamino-propionamide;

(S)—N—((S)-1-Cyclohexyl-2-{(S)-2-[5-(3,5-dimethyl-phenyl)-pyridin-3-yl]-pyrrolidin-1-yl}-2-oxo-ethyl)-2-methylamino-propionamide;

(S)—N—((S)-2-{(S)-2-[5-(4-tert-Butyl-phenyl)-pyridin-3-yl]-pyrrolidin-1-yl}-1-cyclohexyl-2-oxo-ethyl)-2-methylamino-propionamide;

(S)—N—((S)-1-Cyclohexyl-2-{(S)-2-[5-(4-fluoro-phenyl)-pyridin-3-yl]-pyrrolidin-1-yl}-2-oxo-ethyl)-2-methylamino-propionamide;

(S)—N-{(S)-1-Cyclohexyl-2-oxo-2-[(S)-2-(5-p-tolyl-pyridin-3-yl)-pyrrolidin-1-yl]-ethyl}-2-methylamino-propionamide;

(S)—N-{(S)-1-Cyclohexyl-2-oxo-2-[(S)-2-(5-m-tolyl-pyridin-3-yl)-pyrrolidin-1-yl]-ethyl}-2-methylamino-propionamide;

(S)—N—((S)-2-{(S)-2-[2,3']Bipyridinyl-6-yl-pyrrolidin-1-yl}-1-cyclohexyl-2-oxo-ethyl}-2-methylamino-propionamide;

(S)—N—[(S)-2-((S)-2-[3,3']Bipyridinyl-5-yl-pyrrolidin-1-yl)-1-cyclohexyl-2-oxo-ethyl]-2-methylamino-propionamide;

(S)—N—[(S)-2-((S)-2-[3,4']Bipyridinyl-5-yl-pyrrolidin-1-yl)-1-cyclohexyl-2-oxo-ethyl]-2-methylamino-propionamide;

(S)—N—((S)-1-Cyclohexyl-2-{(S)-2-[6-(6-fluoro-2,3-dihydro-indol-1-yl)-2-methyl-pyrimidin-4-yl]-pyrrolidin-1-yl}-2-oxo-ethyl)-2-methylamino-propionamide;

(S)—N—((S)-1-Cyclohexyl-2-{(S)-2-[6-(5-fluoro-2,3-dihydro-indol-1-yl)-2-methyl-pyrimidin-4-yl]-pyrrolidin-1-yl}-2-oxo-ethyl)-2-methylamino-propionamide;

(S)—N-{(S)-1-Cyclohexyl-2-[(S)-2-(6-indol-1-yl-2-methyl-pyrimidin-4-yl)-pyrrolidin-1-yl]-2-oxo-ethyl}-2-methylamino-propionamide;

(S)—N-{(S)-1-Cyclohexyl-2-[(S)-2-(6-indol-1-yl-pyrimidin-4-yl)-pyrrolidin-1-yl]-2-oxo-ethyl}-2-methylamino-propionamide;

(S)—N-{(S)-1-Cyclohexyl-2-[(S)-2-(2-methyl-6-o-tolyl-pyrimidin-4-yl)-pyrrolidin-1-yl]-2-oxo-ethyl}-2-methylamino-propionamide;

(S)—N-{(S)-1-Cyclohexyl-2-oxo-2-[(S)-2-(6-o-tolyl-pyrimidin-4-yl)-pyrrolidin-1-yl]-ethyl}-2-methylamino-propionamide;

(S)—N—((S)-1-Cyclohexyl-2-{(S)-2-[2-methyl-6-(3-methyl-indol-1-yl)-pyrimidin-4-yl]-pyrrolidin-1-yl}-2-oxo-ethyl)-2-methylamino-propionamide;

(S)—N—((S)-1-Cyclohexyl-2-{(S)-2-[2-methyl-6-(3-trifluoromethyl-phenyl)-pyrimidin-4-yl]-pyrrolidin-1-yl}-2-oxo-ethyl)-2-methylamino-propionamide;

(S)—N-{(S)-2-[(S)-2-(6-Benzoimidazol-1-yl-2-methyl-pyrimidin-4-yl)-pyrrolidin-1-yl]-1-cyclohexyl-2-oxo-ethyl}-2-methylamino-propionamide;

(S)—N-{(S)-1-Cyclohexyl-2-[(S)-2-(2-methyl-6-naphthalen-1-yl-pyrimidin-4-yl)-pyrrolidin-1-yl]-2-oxo-ethyl}-2-methylamino-propionamide;

(S)—N-{(S)-2-[(S)-2-(6-Benzo[1,3]dioxol-5-yl-2-methyl-pyrimidin-4-yl)-pyrrolidin-1-yl]-1-cyclohexyl-2-oxo-ethyl}-2-methylamino-propionamide;

(S)—N—((S)-1-Cyclohexyl-2-{(S)-2-[6-(3-isopropyl-phenyl)-2-methyl-pyrimidin-4-yl]-pyrrolidin-1-yl}-2-oxo-ethyl)-2-methylamino-propionamide;

(S)—N—((S)-1-Cyclohexyl-2-{(S)-2-[6-(2,3-dihydro-indol-1-yl)-2-methyl-pyrimidin-4-yl]-pyrrolidin-1-yl}-2-oxo-ethyl)-2-methylamino-propionamide;

(S)—N-{(S)-1-Cyclohexyl-2-[(S)-2-(2-methyl-6-naphthalen-2-yl-pyrimidin-4-yl)-pyrrolidin-1-yl]-2-oxo-ethyl}-2-methylamino-propionamide;

(S)—N—((S)-1-Cyclohexyl-2-{(S)-2-[6-(5-fluoro-2,3-dihydro-indol-1-yl)-pyrimidin-4-yl]-pyrrolidin-1-yl}-2-oxo-ethyl)-2-methylamino-propionamide;

(S)—N—((S)-1-{(S)-2-[6-(5-Fluoro-2,3-dihydro-indol-1-yl)-2-methyl-pyrimidin-4-yl]-pyrrolidine-1-carbonyl}-2-methyl-propyl)-2-methylamino-propionamide;

(S)—N-{(S)-2-[(S)-2-(6-Benzofuran-3-yl-2-methyl-pyrimidin-4-yl)-pyrrolidin-1-yl]-1-cyclohexyl-2-oxo-ethyl}-2-methylamino-propionamide;

(S)—N—((S)-1-Cyclohexyl-2-{(S)-2-[6-(1H-indol-3-yl)-2-methyl-pyrimidin-4-yl]-pyrrolidin-1-yl}-2-oxo-ethyl)-2-methylamino-propionamide;

(S)—N—((S)-1-Cyclohexyl-2-{(S)-2-[6-(1H-indol-3-yl)-pyrimidin-4-yl]-pyrrolidin-1-yl}-2-oxo-ethyl)-2-methylamino-propionamide;

(S)—N—((S)-1-{(S)-2-[6-(1H-Indol-3-yl)-2-methyl-pyrimidin-4-yl]-pyrrolidine-1-carbonyl}-2-methyl-propyl)-2-methylamino-propionamide;

(S)—N—((S)-1-Cyclohexyl-2-{(S)-2-[6-(5-fluoro-3-methyl-indol-1-yl)-2-methyl-pyrimidin-4-yl]-pyrrolidin-1-yl}-2-oxo-ethyl)-2-methylamino-propionamide;

(S)—N—((S)-1-{(S)-2-[6-(5-Fluoro-3-methyl-indol-1-yl)-2-methyl-pyrimidin-4-yl]-pyrrolidine-1-carbonyl}-2-methyl-propyl)-2-methylamino-propionamide;

(S)—N—((S)-1-Cyclohexyl-2-{(S)-2-[6-(5-fluoro-3-methyl-indol-1-yl)-pyrimidin-4-yl]-pyrrolidin-1-yl}-2-oxo-ethyl)-2-methylamino-propionamide;

(S)—N—((S)-1-Cyclohexyl-2-{(S)-2-[6-(5-fluoro-indol-1-yl)-2-methyl-pyrimidin-4-yl]-pyrrolidin-1-yl}-2-oxo-ethyl)-2-methylamino-propionamide;

(S)—N—((S)-1-{(S)-2-[6-(5-Fluoro-indol-1-yl)-2-methyl-pyrimidin-4-yl]-pyrrolidine-1-carbonyl}-2-methyl-propyl)-2-methylamino-propionamide;

(S)—N—((S)-1-Cyclohexyl-2-{(S)-2-[6-(5-fluoro-indol-1-yl)-pyrimidin-4-yl]-pyrrolidin-1-yl}-2-oxo-ethyl)-2-methylamino-propionamide;

3-(6-{(S)-1-[(S)-2-Cyclohexyl-2-((S)-2-methylamino-propionylamino)-acetyl]-pyrrolidin-2-yl}-2-methyl-pyrimidin-4-yl)-indole-1-carboxylic acid dimethylamide;

3-(2-Methyl-6-{(S)-1-[(S)-3-methyl-2-((S)-2-methylamino-propionylamino)-butyryl]-pyrrolidin-2-yl}-pyrimidin-4-yl)-indole-1-carboxylic acid dimethylamide;

3-(6-{(S)-1-[(S)-2-Cyclohexyl-2-((S)-2-methylamino-propionylamino)-acetyl]-pyrrolidin-2-yl}-pyrimidin-4-yl)-indole-1-carboxylic acid dimethylamide; and (S)—N—((S)-1-{(S)-2-[6-(6-Fluoro-2,3-dihydro-indol-1-yl)-2-methyl-pyrimidin-4-yl]-pyrrolidine-1-carbonyl}-2-methyl-propyl)-2-methylamino-propionamide;

or a pharmaceutically acceptable salt thereof.

10. A compound of claim 9 selected from the group consisting of (S)—N—((S)-1-Cyclohexyl-2-{(S)-2-[2-(5-fluoro-indol-1-yl)-pyridin-4-yl]-pyrrolidin-1-yl}-2-oxo-ethyl)-2-methylamino-propionamide;

(S)—N-{(S)-1-Cyclohexyl-2-[(S)-2-(5-indazol-1-yl-pyridin-3-yl)-pyrrolidin-1-yl]-2-oxo-ethyl}-2-methylamino-propionamide;

(S)—N-{(S)-2-[(S)-2-(2-Benzoimidazol-1-yl-3-fluoro-pyridin-4-yl)-pyrrolidin-1-yl]-1-cyclohexyl-2-oxo-ethyl}-2-methylamino-propionamide;

(S)—N-{(S)-1-[(S)-2-(2-Benzoimidazol-1-yl-pyridin-4-yl)-pyrrolidine-1-carbonyl]-2-methyl-propyl}-2-methylamino-propionamide;

(S)—N-{(S)-1-Cyclohexyl-2-[(S)-2-(5-naphthalen-2-yl-pyridin-3-yl)-pyrrolidin-1-yl]-2-oxo-ethyl}-2-methylamino-propionamide;

(S)—N-{(S)-2-[(S)-2-(5-Benzo[1,3]dioxol-5-yl-pyridin-3-yl)-pyrrolidin-1-yl]-1-cyclohexyl-2-oxo-ethyl}-2-methylamino-propionamide;

(S)—N-{(S)-1-Cyclohexyl-2-oxo-2-[(S)-2-(5-p-tolyl-pyridin-3-yl)-pyrrolidin-1-yl]-ethyl}-2-methylamino-propionamide; and (S)—N—((S)-1-Cyclohexyl-2-{(S)-2-[5-(3,5-dimethyl-phenyl)-pyridin-3-yl]-pyrrolidin-1-yl}-2-oxo-ethyl)-2-methylamino-propionamide;

or a pharmaceutically acceptable salt thereof.

\* \* \* \* \*